United States Patent
Buchwald et al.

(10) Patent No.: US 6,867,310 B1
(45) Date of Patent: Mar. 15, 2005

(54) ARYLATION AND VINYLATION OF ACTIVATED CARBONS

(75) Inventors: Stephen L. Buchwald, Newton, MA (US); John P. Wolfe, Brighton, MA (US); Jens Ahman, Sandwich (GB); Malisa Troutman, Irvington, NY (US); Michael Palucki, Belle Meade, NJ (US); Ken Kamikawa, Brookline, MA (US); Andre Chieffi, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/239,024

(22) Filed: Jan. 27, 1999

Related U.S. Application Data

(63) Continuation-in-part of application No. 09/196,855, filed on Nov. 20, 1998, now abandoned.
(60) Provisional application No. 60/065,970, filed on Nov. 20, 1997.

(51) Int. Cl.$^7$ ............................................. C07D 317/44
(52) U.S. Cl. ...................... 549/453; 549/446; 568/316; 568/312; 564/169; 564/275; 556/143; 556/144; 548/540; 560/82
(58) Field of Search ................................. 549/446, 453; 568/312, 316; 564/275, 169; 556/143, 144; 560/82; 548/540

(56) References Cited

U.S. PATENT DOCUMENTS

| | | | |
|---|---|---|---|
| 4,992,591 A | 2/1991 | Hou et al. .................... | 568/315 |
| 5,248,815 A | 9/1993 | Paradies ...................... | 562/496 |
| 5,530,125 A | 6/1996 | Berger et al. ................ | 540/594 |
| 5,880,301 A | 3/1999 | Shibasaki et al. ............. | 556/21 |
| 6,057,456 A | 5/2000 | Hartwig et al. .............. | 548/540 |
| 6,072,073 A | 6/2000 | Kawatsura et al. ........... | 560/82 |

FOREIGN PATENT DOCUMENTS

| | | |
|---|---|---|
| WO | WO 98/22429 | 5/1998 |
| WO | WO 98/49128 | 11/1998 |

OTHER PUBLICATIONS

Åhman, J. et al., "Asymmetric Arylation of Ketone Enolates", *J. Am. Chem. Soc.*, 120:1918–1919 (1998).

Benhaddou, R. et al., "Palladium–Mediated Arylation of Acetylated Enenes Derived from Glycals. 4. Synthesis of Aryl 2–Deoxy–β–D–C–glycopyranosides", *J. Org. Chem.*, 57:4612–4616 (1992).

Cho, C. et al., "Palladium(III)–Catalyzed Hydroarylation of α,β–Unsaturated Aldehydes and Ketones wtih Triarylstibines in the Presence of Silver Acetate", *Tetrahedron Letters*, 8:1275–1278 (1994).

Ciufolini, M. et al., "Intramolecular Arylations of Soft Enolates Catalyzed by Zerovalent Palladium", *J. Org. Chem.*, 53:4149–4151 (1988).

(List continued on next page.)

*Primary Examiner*—Samuel Barts
(74) *Attorney, Agent, or Firm*—Dana M. Gordon; Foley Hoag LLP

(57) ABSTRACT

The present invention provides transition-metal-catalyst-based methods for the arylation and vinylation of activated methyl, methylene, and methine carbons with aryl halides, vinyl halides, and the like. The methods of the invention provide several improvements over existing methods, including the ability to synthesize efficiently and under mild conditions α-aryl and α-vinyl products from a wide range of starting materials, including ketones, esters, hydrazones, and imines. Furthermore, the methods of the invention may be used in an asymmetric sense, i.e. to produce enantiomerically-enriched chiral α-aryl and α-vinyl products.

30 Claims, 5 Drawing Sheets

Examples of the Asymmetric Arylation of 2-Methylcyclopentanone Bearing a Blocking Group at the 5-Position

| R | Ligand | %Pd | %L | Base | T C° | Y% | ee % |
|---|---|---|---|---|---|---|---|
| 4-$^t$Bu | (S)-BINAP | 10 | 15 | NaHMDS | 100 | 67 | 90 |
| 4-$^t$Bu | (S)-BINAP | 10 | 15 | NaO$^t$Bu | 100 | 70 | 89 |
| 4-$^t$Bu | (R)-QUINAP | 5 | 7.5 | NaO$^t$Bu | 90 | 67 | 23 |
| 4-$^t$Bu | (R)-MOP | 10 | 15 | KO$^t$Bu | 100 | 68 | 34 |
| 4-$^t$Bu | (S)-BINAP | 10 | 15 | KO$^t$Bu | 100 | 54 | 84 |
| 4-$^t$Bu | (R)-QUINAP | 10 | 15 | KO$^t$Bu | 100 | 23 | 15 |
| 4-$^t$Bu | (S)-BINAP | 10 | 15 | KO$^t$Bu | 100 | 63 | 85 |
| 4-$^t$Bu | (S)-BINAP | 10 | 15 | KHMDS | 100 | 51 | 86 |
| 4-$^t$Bu | (-)-1 | 5 | 7.5 | NaO$^t$Bu | rt | 93 | 68 |
| 4-$^t$Bu | (-)-1 | 5 | 7.5 | NaO$^t$Bu | rt | 99 | 67 |
| 3-OMe | (S)-BINAP | 10 | 15 | NaO$^t$Bu | 100 | 91 | 85 |
| 4-OMe | (S)-BINAP | 5 | 10 | NaO$^t$Bu | 100 | 55 | 62 |
| 4-OMe | (S)-BINAP | 10 | 15 | NaO$^t$Bu | 100 | 65 | 57 |
| 3-(2-dioxolane) | (S)-BINAP | 10 | 15 | NaO$^t$Bu | 100 | 96 | 86 |

[1 = 2-(dicyclohexylphosphino)-2'-(dimethylamino)-1,1'-binaphthyl]

OTHER PUBLICATIONS

Galarini, R. et al., "Asymmetric synthesis of alkyl 2-arylalkanoates by cross-coupling reactions catalyzed by PD complexes", *J. Molecular Catalysts*, 72:L11–L13 (1992).

Hamann, B and Hartwig, J., "Palladium–Catalyzed Direct α–Arylation of Ketones. Rate Acceleration by Sterically Hindered Chelating Ligands and Reductive Elimination from a Transition Metal Enolate Complex", *J. Am. Chem. Soc.*, 119:12382–12383 (1997).

Itaya, T. and Hozumi, Y., "Synthesis of Optically Active (2–Arylvinyl)glycine Derivatives by Palladium–Catalyzed Arylation of (S)–N–(Benzyloxycarbonyl)vinylglycine", *Chem. Pharm. Bull.*, 46:1094–1101 (1998).

Jeffery, T., "Palladium–catalysed Arylation of Allylic Alcohols: Highly Selective Synthesis of β–Aromatic Carbonyl Compounds of β–Aromatic α,β–Unsaturated Alcohols", *Tetrahedron Letters*, 32:2121–2124 (1991).

Kosugi, M. et al., "Arylation and 1–Alkenylation on β–Position of Ketones via Tributyltin Enolates catalyzed by Palladium Complex", *Bull. Chem. Soc. Japan*, 57:242–246 (1984).

Kosugi, M. et al. "α–Phenylation of Ketones via Tin Enolates Catalysed by a Palladium Complex", *J. Chem. Soc., Chem Commun.*, 344–345 (1983).

Masuyama, Y.et al., Palladium–Catalyzed Intramolecular Carbonyl Allylation via Claisen Rearrangement, *Tetrahedron Letters*, 33:6477–6478 (1992).

Muratake, H. et al., "A Novel Phenol–Forming Reaction for Preperation of Benezene, Furan, and Thiophene Analogs of CC–1065/Duocarmycin Pharmacophores", *Tetrahedron Letters*, 38:7577–7580 (1997).

Muratake, H. and Natsume, M., "Palladium–Catalyzed Intramolecular α–Arylation of Aliphatic Ketones", *Tetrahedron Letters*, 43:7581–7582 (1997).

Negishi, E. et al., "Highly Selective Methods for α–Alkenylation and α–Arylation of Ketones via Palladium– or Nickle–Catalyzed Cross Coupling", *Chemistry Letters*, 1007–1010 (1987).

Palucki, M. and Buchwald, S., "Palladium–Catalyzed α–Arylation of Ketones", *J. Am. Chem. Soc.*, 119:11108–11109 (1997).

Tamao, K. et al., "α–Alkylation and α–Arylation of Carbonyl Groups: Nickel–Phosphine Complex–Catalyzed Grignard Coupling of vic–Bromotrimethylsiloxtalkenes", *Chemistry Letters*, 1239–1242 (1976).

Terao, Y. et al., "Regioselective Arylation on the γ–Position of α,β–Unsaturated Carbonyl Compounds with Aryl Bromides by Palladium Catalysis", *Tetrahedron Letters*, 39:6203–6206 (1998).

Figure 1

Examples of the Asymmetric Arylation of 2-Methylcyclopentanone Bearing a Blocking Group at the 5-Position

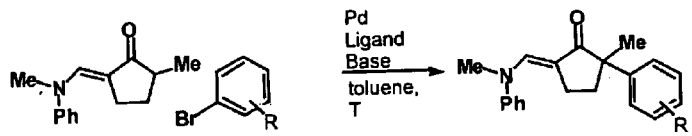

| R | Ligand | %Pd | %L | Base | T C° | Y% | ee % |
|---|---|---|---|---|---|---|---|
| 4-$^t$Bu | (S)-BINAP | 10 | 15 | NaHMDS | 100 | 67 | 90 |
| 4-$^t$Bu | (S)-BINAP | 10 | 15 | NaO$^t$Bu | 100 | 70 | 89 |
| 4-$^t$Bu | (R)-QUINAP | 5 | 7.5 | NaO$^t$Bu | 90 | 67 | 23 |
| 4-$^t$Bu | (R)-MOP | 10 | 15 | KO$^t$Bu | 100 | 68 | 34 |
| 4-$^t$Bu | (S)-BINAP | 10 | 15 | KO$^t$Bu | 100 | 54 | 84 |
| 4-$^t$Bu | (R)-QUINAP | 10 | 15 | KO$^t$Bu | 100 | 23 | 15 |
| 4-$^t$Bu | (S)-BINAP | 10 | 15 | KO$^t$Bu | 100 | 63 | 85 |
| 4-$^t$Bu | (S)-BINAP | 10 | 15 | KHMDS | 100 | 51 | 86 |
| 4-$^t$Bu | (-)-1 | 5 | 7.5 | NaO$^t$Bu | rt | 93 | 68 |
| 4-$^t$Bu | (-)-1 | 5 | 7.5 | NaO$^t$Bu | rt | 99 | 67 |
| 3-OMe | (S)-BINAP | 10 | 15 | NaO$^t$Bu | 100 | 91 | 85 |
| 4-OMe | (S)-BINAP | 5 | 10 | NaO$^t$Bu | 100 | 55 | 62 |
| 4-OMe | (S)-BINAP | 10 | 15 | NaO$^t$Bu | 100 | 65 | 57 |
| 3-(2-dioxolane) | (S)-BINAP | 10 | 15 | NaO$^t$Bu | 100 | 96 | 86 |

[1 = 2-(dicyclohexylphosphino)-2'-(dimethylamino)-1,1'-binaphthyl]

Figure 2

Additional Examples of the Asymmetric Arylation of 2-Methylcyclopentanone Bearing a Blocking Group at the 5-Position

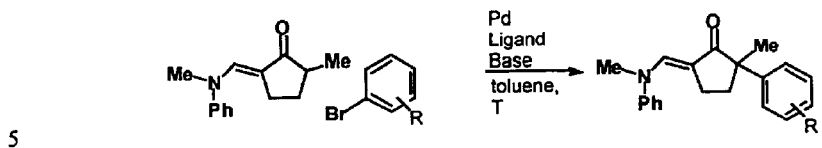

| R | Ligand | %Pd | %L | Base | T C° | Y% | ee % |
|---|---|---|---|---|---|---|---|
| 4-Me | (S)-BINAP | 10 | 15 | NaO$^t$Bu | 100 | 65 | 63 |
| 4-Me | (R)-QUINAP | 10 | 15 | NaO$^t$Bu | 100 | 82 | 25 |
| 4-Me | (-)-1 | 5 | 7.5 | NaO$^t$Bu | rt | 88 | 75 |
| 2-Me | (S)-BINAP | 5 | 10 | NaO$^t$Bu | 100 | 52 | 10 |
| 2-Me | (S)-BINAP | 5 | 10 | NaO$^t$Bu | 100 | 48 | 8 |
| 3-Me | (S)-BINAP | 5 | 10 | NaO$^t$Bu | 100 | 70 | 80 |
| 3-Me | (S)-BINAP | 5 | 10 | NaO$^t$Bu | 100 | 72 | 80 |
| 4-CF$_3$ | (S)-BINAP | 10 | 15 | NaO$^t$Bu | 100 | 93 | 53 |
| 4-CF$_3$ | (S)-BINAP | 10 | 15 | NaO$^t$Bu | 80 | 80 | 44 |
| 4-CF$_3$ | (R)-QUINAP | 5 | 7.5 | NaO$^t$Bu | 90 | 54 | 43 |
| 3-CF$_3$ | (S)-BINAP | 5 | 7.5 | NaO$^t$Bu | 100 | 60 | 75 |
| 4-CN | (-)-1 | 5 | 7.5 | NaO$^t$Bu | rt | 51 | 80 |

[1 = 2-(dicyclohexylphosphino)-2'-(dimethylamino)-1,1'-binaphthyl]

Asymmetric Arylation of 2-pentylcyclopentanone Bearing a Blocking Group at the 5-Position

| R | "Pd" | Ligand | %Pd | %L | T C° | Y% | ee % |
|---|------|--------|-----|-----|------|-----|------|
| H | Pd2(dba)3 | (S)-BINAP | 10 | 15 | 93 | 84 | 93 |
| H | Pd(OAc)2 | (-)-1 | 10 | 15 | 72 | 78 | 72 |
| 3-Me | Pd(OAc)2 | (S)-BINAP | 10 | 15 | 100 | 70 | 99 |
| 4-CF3 | Pd2(dba)3 | (S)-BINAP | 10 | 15 | 100 | 71 | 90 |

[1 = 2-(dicyclohexylphosphino)-2'-(dimethylamino)-1,1'-binaphthyl]

Figure 4 α-Arylation of 2-Methyl-1-Tetralone—Ligand Effects
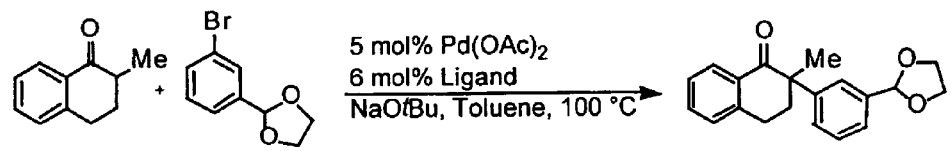
| Ligand | Yield | ee |
|---|---|---|
| (S)-BINAP | 69 | 84 |
| (R)-QUINAP | 43 | 84 |
| (R)-MeO-BIPHEP | 59 | 85 |
| (S)-BIPHEMP | 39 | 82 |
| (R,R)-NORPHOS | 38 | 40 |
| (R)-MOP | 19 | 8 |
| (R)-PPF-OMe | 38 | 1 |
| (R)-(S)-JOSIPHOS | 38 | 2 |
| (S)-Et-DUPHOS [a] | 8 | 12 |
| (S)-Tol-BINAP [b] | 26 | 30 |
(a) Reaction run with 10 mol% Pd(dba)$_3$, 24 mol% (S)-Tol-BINAP, NaHMDS as base. (b) Reaction run with 2.5 mol% Pd(dba)$_3$, 6 mol% (S)-Et-DUPHOS, NaHMDS as base.
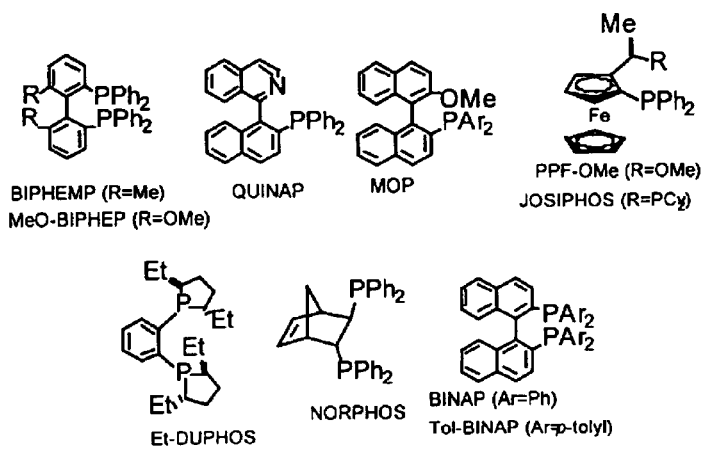

Figur 5. α-Arylations of Ketones in the Absence of a Phosphine Ligand.

$$\underset{R}{\overset{O}{\|}}\!\!\!\!\!\!\diagdown\!\!R' + ArBr \xrightarrow[\substack{\text{toluene}\\ 80\,°C}]{\substack{Pd(OAc)_2 \\ \text{or } Pd_2(DBA)_3 \\ NaO^tBu}} \underset{R}{\overset{O}{\|}}\!\!\!\!\!\!\underset{Ar}{\diagdown\!\!R'}$$

| entry | Ketone | Aryl Bromide | Pd Source (mol %) | (% yield) |
|---|---|---|---|---|
| 1 | Ph−C(O)−Me | $^t$Bu−C$_6$H$_4$−Br | Pd$_2$(DBA)$_3$ (1.5 mol %) | 55% |
| 2 | Ph−C(O)−Me | 3-MeO−C$_6$H$_4$−Br | Pd$_2$(DBA)$_3$ (1.5 mol %) | 54% |
| 3 | Ph−C(O)−Me | 3-MeO−C$_6$H$_4$−Br | Pd(OAc)$_2$ (1 mol %) | 79% |
| 4 | Ph−C(O)−Me | 2-MeO−C$_6$H$_4$−Br | Pd$_2$(DBA)$_3$ (1.5 mol %) | 46% |
| 5 | $^t$Bu−C(O)−Me | 3-MeO−C$_6$H$_4$−Br | Pd$_2$(DBA)$_3$ (1.5 mol %) | 48% |
| 6 | $^t$Bu−C(O)−Me | 3-MeO−C$_6$H$_4$−Br | Pd(OAc)$_2$ (1 mol %) | 71% |
| 7 | Ph−C(O)−Me | 4-MeO−C$_6$H$_4$−Br | Pd(OAc)$_2$ (1 mol %) | 79% |
| 8 | Ph−C(O)−Me | 3,5-Me$_2$−C$_6$H$_3$−Br | Pd(OAc)$_2$ (1 mol %) | 83% |
| 9 | Ph−C(O)−Me | 3,5-Me$_2$−C$_6$H$_3$−Br | Pd$_2$(DBA)$_3$ (0.5 mol %) | 79% |
| 10 | 4-Me−C$_6$H$_4$−C(O)−Me | 2,4-Me$_2$−C$_6$H$_3$−Br | Pd(OAc)$_2$ (1.0 mol %) | 64% |

US 6,867,310 B1

ARYLATION AND VINYLATION OF ACTIVATED CARBONS

RELATED APPLICATIONS

This application is a continuation-in-part of U.S. application Ser. No. 09/196,855, filed Nov. 20, 1998 now abandoned, which claimed the benefit of the filing date of U.S. Provisional Application No. 60/065,970, filed Nov. 20, 1997.

GOVERNMENT SUPPORT

The present invention was made in part with support provided by the National Science Foundation and the National Institutes of Health; the government, therefore, has certain rights in the invention.

BACKGROUND OF THE INVENTION

Formation of a new carbon—carbon bond at a position α to an electron withdrawing group, i.e. at an activated methyl, methylene or methine carbon, is typically achieved by nucleophilic attack of the conjugate base of the activated carbon, e.g., an enolate or ketene acetal, at an electrophilic carbon, e.g., a carbonyl carbon or a carbon bearing a good leaving group. While this paradigm is effective in a range of contexts, e.g., the aldol condensation and enolate alkylation, its scope, in fact, is limited. For example, existing methods for the formation of a carbon—carbon bond between an sp$^2$-hybridized carbon of an aromatic nucleus and an activated carbon require that the aromatic nucleus be susceptible to nucleophilic aromatic substitution, e.g., that it bear a number of electron withdrawing groups in appropriate positions. Furthermore, corresponding limitations exist in the art vis-a-vis the ability to install a vinyl group at an activated carbon, i.e. the requirement that the vinylating group be predisposed to an addition-elimination mechanism. A general method for the arylation and/or vinylation of activated methyl, methylene, and methine carbons, that utilizes readily available starting materials and affords products in high regioselectivity, is not known in the art.

The synthesis of α-aryl ketones has received much attention over the past two decades. A number of stoichiometric arylating reagents have been successfully developed for this purpose, however, their utility is decreased because each synthesis of an α-aryl ketone requires the synthesis of a different arylating reagent. In contrast, the direct coupling of aryl halides with ketones would provide a convenient method for the synthesis of α-aryl ketones. Semmelhack et al. have demonstrated that Ni(COD)$_2$ catalyzes the intramolecular coupling of an aryl iodide with a ketone enolate. While there are reports of Pd or Ni-catalyzed intermolecular coupling reactions that afford α-aryl ketones, these methods require the use of stoichiometric amounts of tin reagents, and/or the use of enol ether, enamine or α-chloroketone derivatives instead of the ketone. Thus, a general method which utilizes readily available starting materials and affords products in high regioselectivity has not been realized.

SUMMARY OF THE INVENTION

The present invention provides transiton-metal-catalyst-based methods for the arylation and vinylation of activated methyl, methylene, and methine carbons with aryl halides, vinyl halides, and the like. The methods of the invention provide several improvements over existing methods, including the ability to synthesize efficiently and under mild conditions α-aryl and α-vinyl products from a wide range of starting materials, including ketones, esters, hydrazones, and imines. Furthermore, the methods of the invention may be used in an asymmetric sense, i.e. to produce enantiomerically-enriched chiral α-aryl and α-vinyl products.

BRIEF DESCRIPTION OF THE FIGURES

FIG. 1 presents tabulated data from fourteen examples of the asymmetric arylation of 2-methylcyclopentanone bearing a blocking group at the 5-position.

FIG. 2 presents tabulated data from twelve additional examples of the asymmetric arylation of 2-methylcyclopentanone bearing a blocking group at the 5-position.

FIG. 4 presents tabulated data on ligand effects in the asymmetric arylation of 2-methyl-1-tetralone.

FIG. 5 presents tabulated data on α-arylations of ketones in the absence of a phosphine ligand.

DETAILED DESCRIPTION OF THE INVENTION

Figure 3:
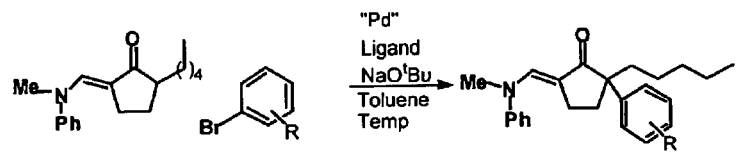
FIG. 3 presents tabulated data from four examples of the asymmetric arylation of 2-pentylcyclopentanone bearing a blocking group at the 5-position.

In one aspect of the invention, an activated methyl, methylene or methine carbon is arylated by reacting an activated aryl group (ArX) with a compound comprising said activated methyl, methylene or methine carbon, e.g., compound 1 in scheme 1, in the presence of a transition metal catalyst. The transition metal catalyst preferably comprises a metal atom taken from the Group VIIIA transition metals, i.e. iron, cobalt, nickel, ruthenium, rhodium, palladium, osmium, iridium and platinum; platinum, palladium and nickel (group 10) are the most preferred transition metals. The aryl group comprises an activated substituent, X, which typically is a moiety whose conjugate acid, HX, has a pKa of less than 5. In certain embodiments, the reaction mixture will also include a base, e.g., NaOtBu or Cs$_2$CO$_3$, which may deprotonate the activated methyl, methylene or methine carbon.

In certain embodiments, the method of the present invention is represented by the generalized reaction depicted in Scheme 1:

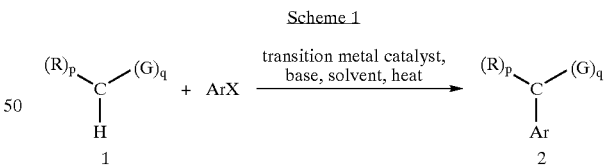

Scheme 1 wherein
  G represents, independently for each occurrence, an electron withdrawing group selected from the group consisting of formyl, acyl, —C(O)OR, —C(O)NR$_2$, nitro, nitroso, —S(O)$_2$R, —SO$_3$R, —S(O)$_2$NR$_2$, —C(NR)—R, —C(NOR)R, and —C(NNR$_2$)—R;
  R represents, independently for each occurrence, hydrogen, alkyl, aryl, heteroalkyl, heteroaryl, halogen, alkylamino, arylamino, alkylthio, arylthio, alkoxy, aryloxy, or —(CH$_2$)$_m$—R$_8$;
  Ar represents an aromatic or heteroaromatic moiety;
  X represents halogen, —OTf, —ONf, —OTs, —OMs, (alkyl)S(O)$_2$O—, or (aryl)S(O)$_2$O—;

the transition metal catalyst comprises a Group VIIIA metal;

base represents a Bronsted base;

$R_8$ represents independently for each occurrence a substituted or unsubstituted aryl, cycloalkyl, cycloalkenyl, heterocycle or polycycle;

m, independently for each occurrence, is an integer selected from the range 0 to 8 inclusive;

q is an integer selected from the range 1 to 3 inclusive; and p is an integer equal to (3-q).

In certain embodiments, the method of the present invention is represented by Scheme 1 and the attendant definitions, wherein the transition metal catalyst comprises a bidentate ligand.

In certain embodiments, the method of the present invention is represented by Scheme 1 and the attendant definitions, wherein the transition metal catalyst comprises an asymmetric ligand; and the reaction produces a non-racemic mixture of a chiral compound.

In certain embodiments, the method of the present invention is represented by Scheme 1 and the attendant definitions, wherein the transition metal catalyst comprises palladium, platinum, or nickel.

In certain embodiments, the method of the present invention is represented by Scheme 1 and the attendant definitions, wherein the transition metal catalyst comprises palladium.

In certain embodiments, the method of the present invention is represented by Scheme 1 and the attendant definitions, wherein the transition metal catalyst comprises palladium and a bidentate ligarid.

In certain embodiments, the method of the present invention is represented by Scheme 1 and the attendant definitions, wherein the transition metal catalyst comprises palladium and an asymmetric bidentate ligand.

In certain embodiments, the method of the present invention is represented by Scheme 1 and the attendant definitions, wherein R represents, independently for each occurrence, hydrogen, alkyl, aryl, heteroalkyl, heteroaryl, or —(CH$_2$)$_m$—R$_8$.

In certain embodiments, the method of the present invention is represented by Scheme 1 and the attendant definitions, wherein X represents Br, I, —OTf, —ONf, —OTs, or —OMs.

In certain embodiments, the method of the present invention is represented by Scheme 1 and the attendant definitions, wherein X represents Br, I, —OTf, or —ONf.

In certain embodiments, the method of the present invention is represented by Scheme 1 and the attendant definitions, wherein the base is an alkoxide, carbonate, or an amide.

In certain embodiments, the method of the present invention is represented by Scheme 1 and the, attendant definitions, wherein the base is a salt of tert-butoxide, dialkylamide, or bis(trialkylsilyl)amide.

In certain embodiments, the method of the present invention is represented by Scheme 1 and the attendant definitions, wherein the base is lithium, sodium, or potassiun tert-butoxide.

In certain embodiments, the method of the present invention is represented by Scheme 1 and the attendant definitions, wherein the base is sodium tert-butoxide.

In certain embodiments, the method of the present invention is represented by Scheme 1 and the attendant definitions, wherein the solvent is a non-polar, aprotic solvent.

In certain embodiments, the method of the present invention is represented by Scheme 1 and the attendant definitions, wherein the solvent is a hydrocarbon.

In certain embodiments, the method of the present invention is represented by Scheme 1 and the attendant definitions, wherein the solvent is an aromatic hydrocarbon.

In certain embodiments, the method of the present invention is represented by Scheme 1 and the attendant definitions, wherein the solvent is toluene.

In certain embodiments, the method of the present invention is represented by Scheme 1 and the attendant definitions, wherein q equals 1.

In certain embodiments, the method of the present invention is represented by Scheme 1 and the attendant definitions, wherein G represents, independently for each occurrence, acyl, formyl, —C(O)OR, —C(O)NR$_2$, —S(O)$_2$R, —SO$_3$R, —S(O)$_2$NR$_2$, —C(NR)—R, —C(NOR)R, or —C(NNR$_2$)—R.

In certain embodiments, the method of the present invention is represented by Scheme 1 and the attendant definitions, wherein G represents, independently for each occurrence, acyl, —C(O)OR, —C(NR)—R, —C(NOR)—R, or —C(NNR$_2$)—R.

In certain embodiments, the method of the present invention is represented by Scheme 1 and the attendant definitions, wherein G represents acyl.

In certain embodiments, the method of the present invention is represented by Scheme 1 and the attendant definitions, wherein the method is practiced between about 70 and 110° C.

In certain embodiments, the method of the present invention is represented by Scheme 1 and the attendant definitions, wherein the method is practiced at about 100° C.

In certain embodiments, the method of the present invention is represented by Scheme 1 and the attendant definitions, wherein the method is practiced at about 70° C.

In certain embodiments, the method of the present invention is represented by Scheme 1 and the attendant definitions, wherein the method is practiced at about 25° C.

In certain embodiments, the method of the present invention is represented by Scheme 1 and the attendant definitions, wherein the product has an ee of greater than or equal to 501/o.

In certain embodiments, the method of the present invention is represented by Scheme 1 and the attendant definitions, wherein the product has an ee of greater than or equal to 70%.

In certain embodiments, the method of the present invention is represented by Scheme 1 and the attendant definitions, wherein the product has an ee of greater than or equal to 80%.

In certain embodiments, the method of the present invention is represented by Scheme 1 and the attendant definitions, wherein the product has an ee of greater than or equal to 90%.

The enantioselective formation of quaternary carbon centers remains a great challenge in organic synthesis. The desirability of such a transformation is evidenced by the number of natural products that contains stereogenic quaternary carbon centers. A number of interesting methods including asymmetric allyl chemistry, phase-transfer catalyzed alkylations and Michael additions to accomplish this task have been reported. Still, new, more general methods, particularly those which complement existing ones, are of great interest. In addition to the generalized arylation reactions described above, we have discovered a means to enantioselectively form a stereogenic quaternary carbon center, e.g., via transition metal-catalyzed ketone arylation. The generalization and optimization of our initial results would provide an efficient and straightforward route to classes of enantiomerically enriched compounds previously not readily available. Moreover, the extension of this methodology to asymmetric vinylation provides a means to accomplish the synthetic equivalent of a catalytic asymmetric alkylation reaction.

In embodiments, where the subject reaction yields a product with a newly formed stereogenic carbon, the reaction preferably has an ee of at least 65%, more preferably 70%, 75%, 80%, 85% and even 90%, though an ee of at least 95% is also contemplated.

The subject reactions may be either intermolecular or intramolecular. In the latter instance, it will be realized that, in terms of Scheme 1, the aryl group of ArX is tethered to an instance of G, or R, or both in 1; two embodiments of the intramolecular transformation may be represented by either of the following transformations:

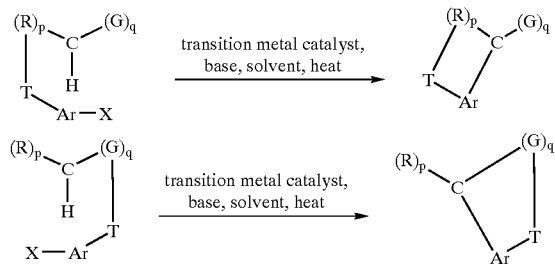

wherein the definitions associated with Scheme 1 apply; and

Y represents a covalent tether connecting an instance of R and Ar, or an instance of G and Ar; said tether may be a single bond or it may comprise atoms; the backbone of said tether may comprise a π-bond, provided that the configuration of said π-bond is such that the described intramolecular reaction is geometrically feasible, or that said π-bond can adopt a configuration under the reaction conditions that renders the intramolecular reaction geometrically feasible; said tether additionally may itself be either unsubstituted or bear any number of substituents of any type permitted by stability and the rules of valence.

Merely for the purpose of illustration, such intramolecular reactions can be used to synthesize, e.g., napthalenones or indenyl ketones.

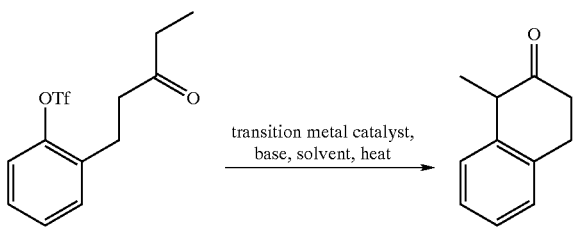

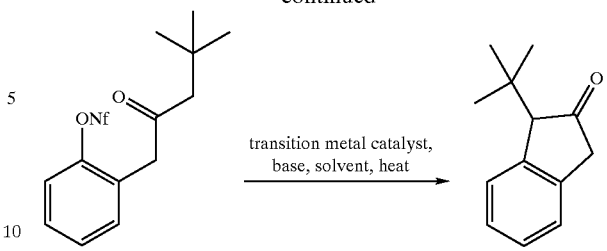

Oxidative addition of the a zero-valent catalyst metal center, e.g., $Pd(0)L_n$, with the aryl group affords the organometallic intermediate A of Scheme 2. In the illustrated example, ligand substitution of the bromide by the sodium enolate of a ketone provides the Pd(II) organometallic intermediate B or C. Given the high degree of regioselectivity of arylation, it is believed that deprotonation of the ketone occurs prior to coordination to the Pd center. Finally, reductive elimination from intermediate B or C provides an α-aryl ketone and regenerates the $Pd(0)L_n$ catalyst. That C doesn't decompose via a β-hydride elimination pathway (in cases where both α-carbons are substituted) further attests to the ability of BINAP and Tol-BINAP to render such complexes four-coordinate.

Scheme 2

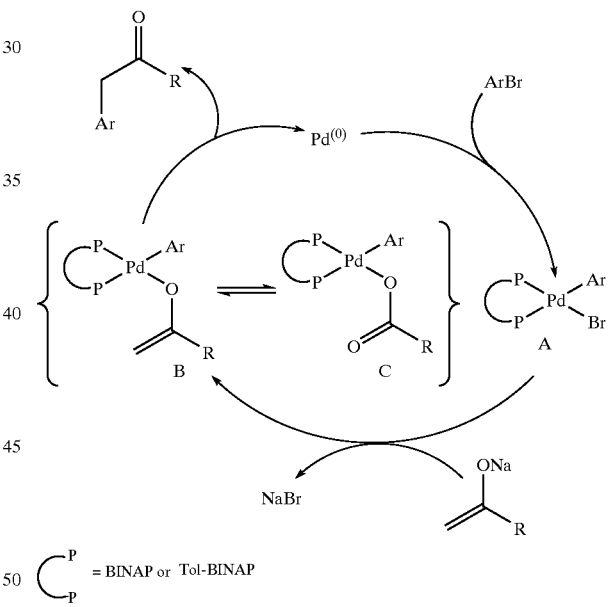

In preferred embodiments of the invention, there is no need to use large excesses of either reactant—activated methyl, methylene, or methine compound or aryl compound. The reaction proceeds quickly and in high yield to the product using substantially stoichiometric amount of reagents. Thus, the activated methyl, methylene, or methine compound may be present in as little as a two-fold excess and preferably in no greater than a 20% excess relative to the aryl compound. Alternatively, the aryl compound may be present in as little as a two-fold excess and preferably in no greater than a 20% excess relative to the activated methyl, methylene, or methine compound.

The extension of the activated methyl, methylene, or methine compound arylation methodology of the subject method to other electrophilic agents such as vinyl, alkynyl and cyclopropyl halides is of considerable interest. Of these, the most important is the vinylation of activated methyl, methylene, or methine compounds. Vinylation, followed by reduction of the double bond is the synthetic equivalent of a catalytic alkylation. This transformation is of particular interest in two situations: 1) those in which the direct alkylation would entail using a secondary alkyl halide substrate (a process that is typically inefficient due to competing elimination), and 2) for construction of asymmetric quaternary carbon centers. Thus, in similar fashion to the reaction depicted in Scheme 1 above, the subject reaction can be carried out using a vinyl-activated hydrocarbon according to generalized reaction Scheme 3.

In certain embodiments, the method of the present invention is represented by the generalized reaction depicted in Scheme 3:

Scheme 3

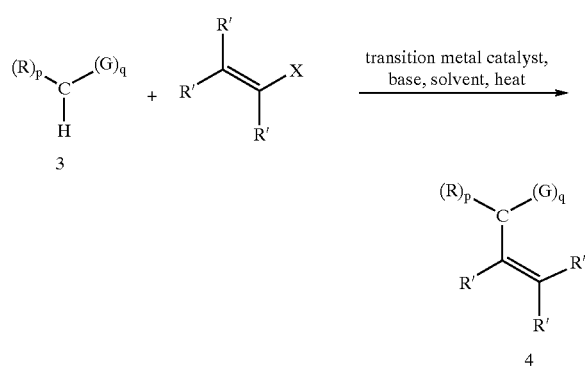

wherein
G represents, independently for each occurrence, an electron withdrawing group selected from the group consisting of formyl, acyl, —C(O)OR, —C(O)NR$_2$, nitro, nitroso, —S(O)$_2$R, —SO$_3$R, —S(O)$_2$NR$_2$, —C(NR)—R, —C(NOR)R, and —C(NNR$_2$)—R;

R represents, independently for each occurrence, hydrogen, alkyl, aryl, heteroalkyl, heteroaryl, halogen, alkylamino, arylamino, alkylthio, arylthio, alkoxy, aryloxy, or CH$_2$)$_m$—R$_8$;

R' represents, independently for each occurrence, hydrogen, alkyl, aryl, heteroalkyl, heteroaryl, alkylamino, arylamino, alkylthio, arylthio, alkoxy, aryloxy, or —(CH$_2$)$_m$—R$_8$;

X represents halogen, —OTf, —ONf, —OTs, —OMs, (alkyl)S(O)O—, or (aryl)S(O)$_2$O—;

the transition metal catalyst comprises a Group VIIIA metal;

base represents a Bronsted base;

R$_8$ represents independently for each occurrence a substituted or unsubstituted aryl, cycloalkyl, cycloalkenyl, heterocycle or polycycle;

m, independently for each occurrence, is an integer selected from the range 0 to 8 inclusive;

q is an integer selected from the range 1 to 3 inclusive; and p is an integer equal to (3-q).

In certain embodiments, the method of the present invention is represented by Scheme 3 and the attendant definitions, wherein the transition metal catalyst comprises a bidentate ligand.

In certain embodiments, the method of the present invention is represented by Scheme 3 and the attendant definitions, wherein the transition metal catalyst comprises an asymmetric ligand; and the reaction produces a non-racemic mixture of a chiral compound.

In certain embodiments, the method of the present invention is represented by Scheme 3 and the attendant definitions, wherein the transition metal catalyst comprises palladium, platinum, or nickel.

In certain embodiments, the method of the present invention is represented by Scheme 3 and the attendant definitions, wherein the transition metal catalyst comprises palladium.

In certain embodiments, the method of the present invention is represented by Scheme 3 and the attendant definitions, wherein the transition metal catalyst comprises palladium and a bidentate ligand.

In certain embodiments, the method of the present invention is represented by Scheme 3 and the attendant definitions, wherein the transition metal catalyst comprises palladium and an asymmetric bidentate ligand.

In certain embodiments, the method of the present invention is represented by Scheme 3 and the attendant definitions, wherein R represents, independently for each occurrence, hydrogen, alkyl, aryl, heteroalkyl, heteroaryl, or —(CH$_2$)$_m$—R$_8$.

In certain embodiments, the method of the present invention is represented by Scheme 3 and the attendant definitions, wherein X represents Br, I, —OTf, —ONf, —OTs, or —OMs.

In certain embodiments, the method of the present invention is represented by Scheme 3 and the attendant definitions, wherein X represents Br, I, —OTf, or —ONf.

In certain embodiments, the method of the present invention is represented by Scheme 3 and the attendant definitions, wherein the base is an alkoxide, carbonate, or an amide.

In certain embodiments, the method of the present invention is represented by Scheme 3 and the attendant definitions, wherein the base is a salt of tert-butoxide, dialkylamide, or bis(trialkylsilyl)amide.

In certain embodiments, the method of the present invention is represented by Scheme 3 and the attendant definitions, wherein the base is lithium, sodium, or potassium tert-butoxide.

In certain embodiments, the method of the present invention is represented by Scheme 3 and the attendant definitions, wherein the base is sodium tert-butoxide.

In certain embodiments, the method of the present invention is represented by Scheme 3 and the attendant definitions, wherein the solvent is a non-polar, aprotic solvent.

In certain embodiments, the method of the present invention is represented by Scheme 3 and the attendant definitions, wherein the solvent is a hydrocarbon.

In certain embodiments, the method of the present invention is represented by Scheme 3 and the attendant definitions, wherein the solvent is an aromatic hydrocarbon.

In certain embodiments, the method of the present invention is represented by Scheme 3 and the attendant definitions, wherein the solvent is toluene.

In certain embodiments, the method of the present invention is represented by Scheme 3 and the attendant definitions, wherein q equals 1.

In certain embodiments, the method of the present invention is represented by Scheme 3 and the attendant definitions, wherein G represents, independently for each occurrence, acyl, formyl, —C(O)OR, —C(O)NR$_2$, —S(O)$_2$R, —SO$_3$R, —S(O)$_2$NR$_2$, —C(NR)—R, —C(NOR)—R, or —C(NNR$_2$)—R.

In certain embodiments, the method of the present invention is represented by Scheme 3 and the attendant definitions, wherein G represents, independently for each occurrence, acyl, —C(O)OR, —C(NR)R, —C(NOR)—R, or —C(NNR$_2$)R.

In certain embodiments, the method of the present invention is represented by Scheme 3 and the attendant definitions, wherein G represents acyl.

In certain embodiments, the method of the present invention is represented by Scheme 3 and the attendant definitions, wherein the method is practiced between about 70 and 110° C.

In certain embodiments, the method of the present invention is represented by Scheme 3 and the attendant definitions, wherein the method is practiced at about 100° C.

In certain embodiments, the method of the present invention is represented by Scheme 3 and the attendant definitions, wherein the method is practiced at about 70° C.

In certain embodiments, the method of the present invention is represented by Scheme 3 and the attendant definitions, wherein the method is practiced at about 25° C.

In certain embodiments, the method of the present invention is represented by Scheme 3 and the attendant definitions, wherein the product has an ee of greater than or equal to 50%.

In certain embodiments, the method of the present invention is represented by Scheme 3 and the attendant definitions, wherein the product has an ee of greater than or equal to 70%.

In certain embodiments, the method of the present invention is represented by Scheme 3 and the attendant definitions, wherein the product has an ee of greater than or equal to 80%.

In certain embodiments, the method of the present invention is represented by Scheme 3 and the attendant definitions, wherein the product has an ee of greater than or equal to 90%.

The subject reactions may be either intermolecular or intramolecular. In the latter instance, it will be realized that, in terms of Scheme 3, the alkenyl group of alkenylX is tethered in 3 to an instance of G, or R, or both; two embodiments of this class of intramolecular transformation are represented by the following transformations:

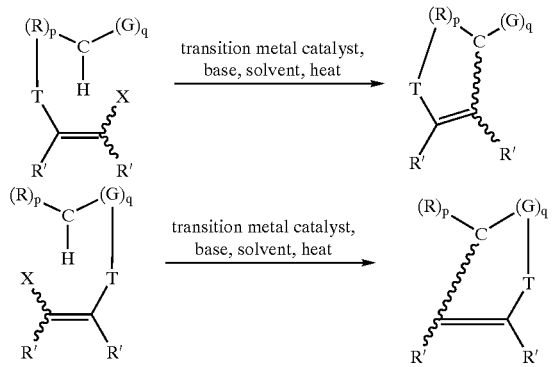

wherein
the definitions associated with Scheme 3 apply; and
T represents a covalent tether connecting an instance of R and the alkenyl moiety, or an instance of G and the alkenyl moiety; said tether may be a single bond or it may comprise atoms; the backbone of said tether may comprise a π-bond, provided that the configuration of said π-bond is such that the described intramolecular reaction is geometrically feasible, or that said π-bond can adopt a configuration under the reaction conditions that renders the intramolecular reaction geometrically feasible; said tether additionally may itself be either unsubstituted or bear any number of substituents of any type permitted by stability and the rules of valence.

The following two transformations are representative of the intramolecular embodiments of the subject vinylation reactions.

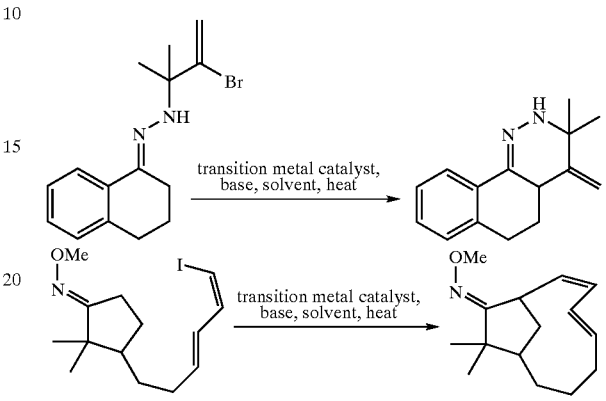

The subject reactions can proceed at mild temperatures and pressures to give high yields of the product. Thus, yields of greater than 45%, preferably greater than 75% and even more preferably greater than 80% may be obtained by reaction at mild temperatures according to the invention. The reaction may be carried out at temperature less than 120° C., and preferably in the range of 50–120° C. In one preferred embodiment, the reaction is carried out at a temperature in the range of 80–100° C.

The reaction can be run in a wide range of solvent systems, including non-polar, aprotic solvents.

The ability to provide a synthesis scheme for the α-arylation of activated methyl, methylene, and methyl compounds which can be carried out under mild conditions and/or with non-polar solvents has broad application, especially in the agricultural and pharmaceutical industries, as well as in the polymer industry. In this regard, the subject reaction is more amenable to use of reactants or products which include sensitive functionalities, e.g., which would otherwise be labile under harsh reaction conditions. In one example, the subject method is useful for the preparation of enantiomerically ketones or their derivatives, e.g., where the creation of quaternary centers of a single absolute configuration, spirocyclic or otherwise, is of considerable interest.

The subject reactions can be used as part of a combinatorial synthesis protocol to yield α-arylated products. Another aspect of the present invention relates to use of the subject method to generate variegated libraries of α-arylated products, and to the libraries themselves. The libraries can be soluble or linked to insoluble supports, e.g., through a substituent on the aryl group.

Definitions

For convenience, before further description of the present invention, certain terms employed in the specification, examples, and appended claims are collected here.

The term "substrate aryl group" refers to an aryl group containing an electrophilic atom which is susceptible to the subject cross-coupling reaction, e.g., the electrophilic atom bears a leaving group. In reaction Scheme 1, the substrate aryl is represented by ArX, and X is the leaving group. The aryl group, Ar, is said to be substituted if, in addition to X it is substituted at yet other positions. The substrate aryl group can be a single ring molecule, or can be a substituent of a larger molecule.

The terms "methyl, methylene, and methine carbons" are recognized in the art and refer to $CH_3$, $CH_2$, and CH groups, respectively.

The terms "activated methyl, methylene, and methine carbons" are recognized in the art and refer to methyl, methylene, and methine carbons, respectively, bearing at least one electron withdrawing group, e.g., a carbonyl, sulfonyl, or nitro group.

The term "nucleophile" is recognized in the art, and as used herein means a chemical moiety having a reactive pair of electrons.

The term "electrophile" is art-recognized and refers to chemical moieties which can accept a pair of electrons from a nucleophile as defined above. Electrophilic moieties useful in the method of the present invention include halides and sulfonates.

The terms "electrophilic atom", "electrophilic center" and "reactive center" as used herein refer to the atom of the substrate aryl moiety which is attacked by, and forms a new bond to, the aryl or vinyl carbon center. In most (but not all) cases, this will also be the aryl ring atom from which the leaving group departs.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (a) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, —CN, chloride, and the like. Exemplary electron-donating groups include amino, methoxy, and the like.

The term "reaction product" means a compound which results from the reaction of the ketone and the substrate aryl group. In general, the term "reaction product" will be used herein to refer to a stable, isolable adduct, and not to unstable intermediates or transition states.

The term "catalytic amount" is recognized in the art and means a substoichiometric amount of a reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

The term "meso compound" is recognized in the art and means a chemical compound which has at least two chiral centers but is achiral due to the presence of an internal plane or point of symmetry.

The term "chiral" refers to molecules which have the property of non-superimposability of their mirror image partner, while the term "achiral" refers to molecules which are superimposable on their mirror image partner. A "prochiral molecule" is a molecule which has the potential to be converted to a chiral molecule in a particular process.

The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoisomerically-enriched" product (e.g., enantiomerically-enriched or diastereomerically-enriched) when the yield of a particular stereoisomer of the product is greater by a statistically significant amount relative to the yield of that stereoisomer resulting from the same reaction run in the absence of a chiral catalyst. For example, a reaction which routinely produces a racemic mixture will, when catalyzed by one of the subject chiral catalysts, yield an e.e. for a particular enantiomer of the product.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant majority of a certain regioisomer.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

$$\% \text{ enantiomeric excess } A(ee) = (\% \text{ enantiomer } A) - (\% \text{ enantiomer } B)$$

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a reactant or reactants (which may be achiral, racemic, non-racemic or enantiomerically pure) to a product enriched in one diastereomer. If the chiral reactant is racemic, in the presence of a chiral, non-racemic reagent or catalyst, one reactant enantiomer may react more slowly than the other. This effect is termed a kinetic resolution, wherein the reactant enantiomers are resolved by differential reaction rate to yield an enantiomerically enriched product. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another reactive center. For example, a regioselective cycloaddition reaction of an unsymmetrical 1,3,5-triene substrate would preferentially occur at one of the two 1,3-dienes contained therein.

The term "non-racemic" means a preparation having greater than 50% of a desired stereoisomer, more preferably at least 75%. "Substantially non-racemic" refers to preparations which have greater than 90% ee for a desired stereoisomer, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), $CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art recognized and refer to both unsubstituted and substituted amines, e.g., a moiety that can be represented by the general formula:

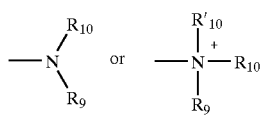

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

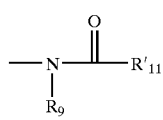

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

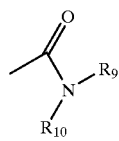

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

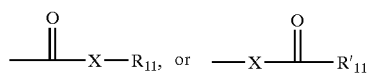

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula: represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

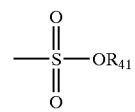

in which $R_{41}$ is an electron pair, hydrogen, alkyl, cycloalkyl, or aryl.

The term "sulfate" is art recognized and includes a moiety that can be represented by the general formula:

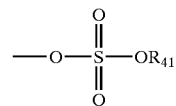

in which $R_{41}$ is as defined above.

The term "sulfonamido" is art recognized and includes a moiety that can be represented by the general formula:

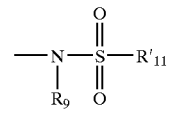

in which $R_9$ and $R'_{11}$ are as defined above.

The term "sulfamoyl" is art-recognized and includes a moiety that can be represented by the general formula:

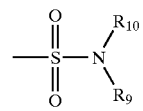

in which $R_9$ and $R_{10}$ are as defined above.

The terms "sulfoxido" or "sulfinyl", as used herein, refers to a moiety that can be represented by the general formula:

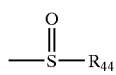

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

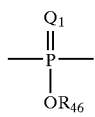

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

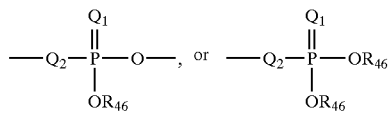

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

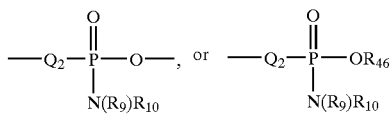

wherein $R_9$ and $R_{10}$ are as defined above, and $Q_2$ represents O, S or N.

A "phosphonamidite" can be represented in the general formula:

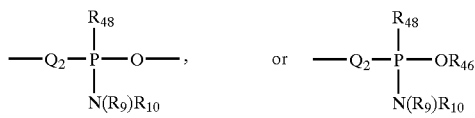

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. A more comprehensive list of the abbreviations utilized by organic chemists of ordinary skill in the art appears in the first issue of each volume of the *Journal of Organic Chemistry*, this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

A "polar solvent" means a solvent which has a dipole moment (E) of 2.9 or greater, such as DMF, THF, ethylene gylcol dimethyl ether, DMSO, acetone, acetonitrile, methanol, ethanol, isopropanol, n-propanol, t-butanol or 2-methoxyethyl ether. Preferred solvents are DMF, diglyme, and acetonitrile.

A "polar, aprotic solvent" means a polar solvent as defined above which has no available hydrogens to exchange with the compounds of this invention during reaction, for example DMF, acetonitrile, diglyme, DMSO, or THF.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Exemplary Catalyzed Reactions

As described above, one invention of the Applicants' features a general cross-coupling reaction which comprises combining an ketone with a aryl or vinyl group (or the like) having an electrophilic center susceptible to attack by the α-carbon of the ketone. In preferred embodiments where the cross-coupling is catalyzed by a transition metal, the reaction will also include at least a catalytic amount of a transition metal catalyst and the combination is maintained under conditions appropriate for the metal catalyst to catalyze the cross-coupling of the electrophilic atom of the substrate aryl group.

In one embodiment, the subect method can be used to bring about formation of an intramolecular linkages, e.g., as shown in reaction scheme 2 above.

The subject method can also be used for the intermolecular formation of carbon-nitrogen bonds. See, scheme 1, and, for example, Table 1 below. As exemplary embodiments, the subject method can be used to catalyze such reactions as:

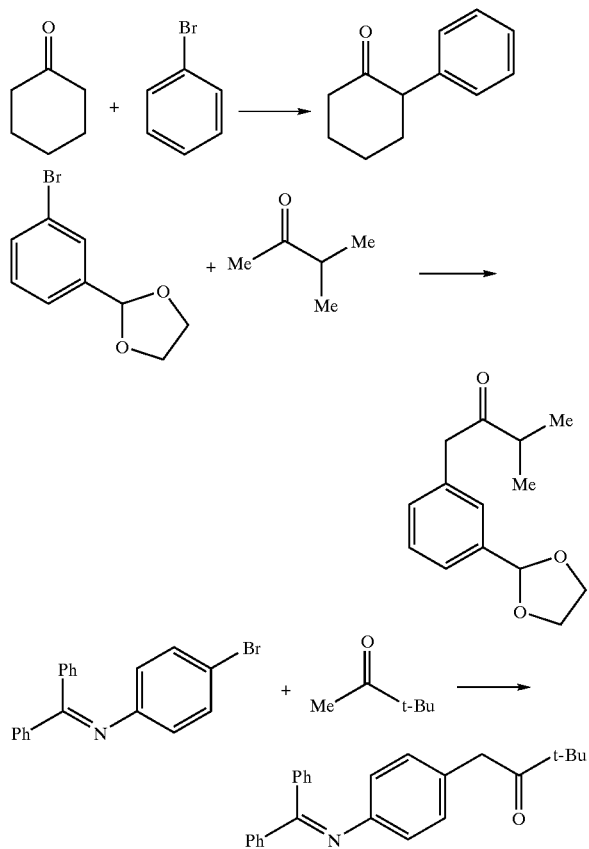

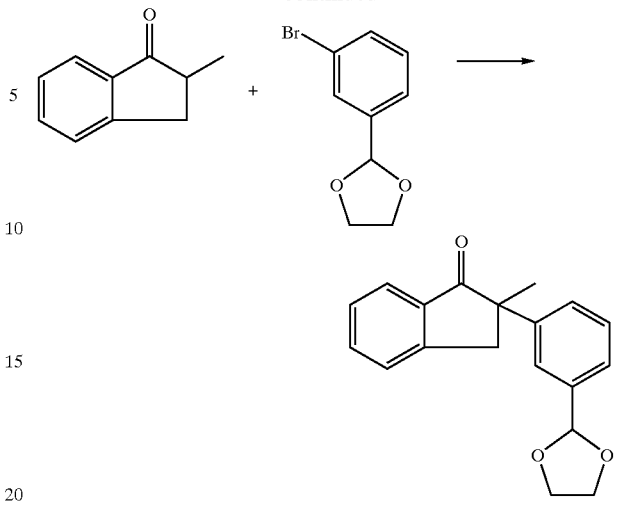

The substrate aryl compounds include compounds derived from simple aromatic rings (single or polycylic) such as benzene, naphthalene, anthracene and phenanthrene; or heteroaromatic rings (single or polycylic), such as pyrrole, thiophene, thianthrene, furan, pyran, isobenzofuran, chromene, xanthene, phenoxathiin, pyrrole, imidazole, pyrazole, thiazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine and the like. In preferred embodiment, the reactive group, X, is substituted on a five, six or seven membered ring (though it can be part of a larger polycyle).

In preferred embodiments, aryl substrate may be selected from the group consisting of phenyl and phenyl derivatives, heteroaromatic compounds, polycyclic aromatic and heteroaromatic compounds, and functionalized derivatives thereof. Suitable aromatic compounds derived from simple aromatic rings and heteroaromatic rings, include but are not limited to, pyridine, imidizole, quinoline, furan, pyrrole, thiophene, and the like. Suitable aromatic compounds derived from fused ring systems, include but are not limited to naphthalene, anthracene, tetralin, indole and the like.

Suitable aryl compounds may have the formula $Z_pArX$, where X is an activated substituent. An activated substituent, X, is characterized as being a good leaving group. In general, the leaving group is a group such as a halide or sulfonate. For the purposes of the present invention, an activated substituent is that moiety whose conjugate acid, HX, has a pKa of less than 5.0. Suitable activated substituents include, by way of example only, halides such as chloride, bromide and iodide, triflate, mesylate and tosylate. In certain embodiments, the leaving group is a halide selected from iodine and bromine. Chlorine and fluorine can also be used as leaving groups, though other electronegative substitution on the aryl group may be required to activate those halogens as leaving groups in the subject metal cross-coupling reactions.

Z represents one or more optional substituents on the aromatic ring, though each occurence of Z (p>1) is independently selected. By way of example only, each incidence of substitution independently can be, as valence and stability permit, a halogen, a lower alkyl, a lower alkenyl, a lower alkynyl, a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, $CH_2)_m-R_8$, $-(CH_2)_m-OH$, $-(CH_2)_m-O-$lower alkyl, $-(CH_2)_m-O$-lower alkenyl, $-(CH_2)_m-O-(CH_2)_n-R_8$, $-(CH_2)_m-SH$, $-(CH_2)_m-S$-lower alkyl, $-(CH_2)_m-S$-lower alkenyl, $(CH_2)_m-S-(CH_2)_n-R_8$, or protecting groups of the above or a solid or polymeric support; $R_8$ represents a substituted or unsubstituted aryl, aralkyl, cycloalkyl, cycloalkenyl, or heterocycle; and n and m are independently for each occurrence zero or an integer in the range of 1 to 6. P is preferably in the range of 0 to 5. For fused rings, where the number of substitution sites on the aryl group increases, p may be adjusted appropriately.

In certain embodiments, suitable substitients Z include alkyl, aryl, acyl, heteroaryl, amino, carboxylic ester, carboxylic acid, hydrogen group, ether, thioether, amide, carboxamide, nitro, phosphonic acid, hydroxyl, sulfonic acid, halide, pseudohalide groups, and substituted derivatives thereof, and n is in the range of 0 to 5. In particular, the reaction has been: found compatible with acetals, amides and silyl ethers as functional groups. For fused rings, where the number of substitution sites on the aromatic ring increases, n may be adjusted appropriately. In addition, the above mentioned moieties may be covalently linked to a ketone moiety in intramolecular reactions.

In preferred embodiments, the resonance structure of the aryl group Ar, or at least one substituent Z, is electron-withdrawing from the substituted position of X.

A wide variety of substrate aryl groups are useful in the methods of the present invention. The choice of substrate will depend on factors such as the alcohol to be employed and the desired product, and an appropriate aryl substrate will be apparent to the skilled artisan. It will be understood that the aryl substrate preferably will not contain any interfering functionalities. It will further be understood that not all activated aryl substrates will react with every ketone.

The ketone is selected to provide the desired reaction product. In general, the ketone may be any ketone such as, but not limited to, dialkyl ketones, and cyclic ketones. The reactive ketone group can be a molecule separate from the substrate aryl group, or a substituent of the same molecule (e.g., for intramolecular condensation).

In certain embodiments, the ketone is generated in situ, e.g., by conversion of a precursor under the reaction conditions.

The active form of the transition metal catalyst is not well characterized. Therefore, it is contemplated that the "transition metal catalyst" of the present invention, as that term is used herein, shall include any transition metal catalyst and/or catalyst precursor as it is introduced into the reaction vessel and which is, if necessary, converted in situ into the active phase, as well as the active form of the catalyst which participates in the reaction.

In preferred embodiments, the transition metal catalyst complex is provided in the reaction mixture is a catalytic amount. In certain embodiments, that amount is in the range of 0.0001 to: 20 mol %, and preferably 0.05 to 5 mol %, and most preferably 1–3 mol %, with respect to the limiting reagent, which may be either the aryl compound or the ketone, or both, depending upon which reagent is in stoichiometric excess. In the instance where the molecular: formula of the catalyst complex includes more than one metal, the amount of the catalyst complex used in the reaction may be adjusted accordingly. By way of example, $Pd_2(dba)_3$ has two metal centers; and thus the molar amount of $Pd_2(dba)_3$ used in the reaction may be halved without sacrifice to catalytic activity.

Additionally, heterogeneous catalysts containing forms of these elements are also suitable catalysts for any of the transition metal catalyzed reactions of the present invention. Catalysts containing palladium and nickel are preferred. It is expected that these catalysts will perform similarly because they are known to undergo similar reactions, namely oxidative-addition reactions and reductive-elimination reactions, which are thought to be involved in the formation of the aminopyridines of the present invention. However, the different ligands are thought to modify the catalyst performance by, for example, modifying reactivity and preventing undesirable side reactions.

As suitable, the catalysts employed in the subject method involve the use of metals which can mediate cross-coupling of the aryl groups Ar—X and the ketone as defined above. In general, any transition metal (e.g., having d electrons) may be used to form the catalyst, e.g., a metal selected from one of Groups 3–12 of the periodic table or from the lanthanide series. However, in preferred embodiments, the metal will be selected from the group of late transition metals, e.g. preferably from Groups 5–12 and even more preferably Groups 7–11. For example, suitable metals include platinum, palladium, iron, nickel, ruthenium and rhodium. The particular form of the metal to be used in the reaction is selected to provide, under the reaction conditions, metal centers which are coordinately unsaturated and not in their highest oxidation state. The metal core of the catalyst should be a zero valent transition metal, such as Pd or Ni with ability to undergo oxidative addition to Ar—X bond. The zero-valent state, $M^0$, may be generated in situ from $M^{+2}$.

To further illustrate, suitable transition metal catalysts include soluble complexes of platinum, palladium and nickel. Nickel and palladium are particularly preferred and palladium is most preferred. A zero-valent metal center is presumed to participate in the catalytic carbon-oxygen bond forming sequence. Thus, the metal center is desirably in the zero-valent state or is capable of being reduced to metal(0). Suitable soluble palladium complexes include, but are not limited to, tris(dibenzylideneacetone)dipalladium $[Pd_2(dba)_3]$, bis(dibenzylideneacetone)palladium $[Pd(dba)_2]$ and palladium acetate. Alternatively, particularly for nickel catalysts, the active species for the oxidative-addition step may be in the metal (+1) oxidative-addition state.

Catalysts containing palladium and nickel are preferred. It is expected that these catalysts will perform comparably because they are known to undergo similar reactions, namely cross-coupling reactions, which may be involved in the formation of the aminopyridines of the present invention.

The coupling can be catalyzed by a palladium catalyst which may take the form of, to illustrate, $PdCl_2$, $Pd(OAc)_2$, $(CH_3CN)_2PdCl_2$, $Pd[P(C_6H_5)_3]_4$, and polymer supported Pd(0). In other embodiments, the reaction can be catalyzed by a nickel catalyst, such as $Ni(acac)_2$, $NiCl_2[P(C_6H_5)]_2$, Raney nickel and the like, wherein "acac" represents acetylacetonate.

The catalyst will preferably be provided in the reaction mixture as metal-ligand complex comprising a bound supporting ligand, that is, a metal-supporting ligand complex. The ligand effects can be key to favoring, inter alia, the reductive elimination pathway or the like which produces the amino coupling. In particular, the use of bulky and less electron-donating ligands (but probably still chelating ligands) should favor the reductive elimination process. In preferred embodiments, the subject reaction employs bulky bidentate ligands such as bisphosphines.

The ligand, as described in greater detail below, may include chelating ligands, such as by way of example only, alkyl and aryl derivatives of phosphines and bisphosphines, imines, arsines, and hybrids thereof, including hybrids of phosphines with amines. Weakly or non-nucleophilic stabilizing ions are preferred to avoid complicating side reaction of the counter ion attacking or adding to the electrophilic center of the substrate aryl. This catalyst complex may include additional ligands as is necessary to obtain a stable complex. Moreover, the ligand can be added to the reaction mixture in the form of a metal complex, or added as a separate reagent relative to the addition of the metal. By way of example, $PdCl_2(BINAP)$ may be prepared in a separate step and used as the catalyst complex set forth in scheme 1a.

The ligand, if chiral can be provided as a racemic mixture or a purified stereoisomer.

The supporting ligand may be added to the reaction solution as a separate compound or it may be complexed to the metal center to form a metal-supporting ligand complex prior to its introduction into the reaction solution. Supporting ligands are compounds added to the reaction solution which are capable of binding to the catalyst metal center, although an actual metal-supporting ligand complex has not been identified in each and every synthesis. In some preferred embodiments, the supporting ligand is a chelating ligand. Although not bound by any theory of operation, it is hypothesized that the supporting ligands prevent unwanted side reactions as well as enhancing the rate and efficiency of the desired process. Additionally, they often aid in keeping the metal catalyst soluble. Although the present invention does not require the formation of a metal-supporting ligand complex, such complexes have been shown to be consistent with the postulate that they are intermediates in these reactions and it has been observed the selection of the supporting ligand has an affect on the course of the reaction.

The supporting ligand is present in the range of 0.0001 to 40 mol % relative to the limiting reagent, i.e., the reactive ketone or aryl compounds. The ratio of the supporting ligand to catalyst complex is typically in the range of about 1 to 20, and preferably in the range of about 1 to 4 and most preferably about 2.4. These ratios are based upon a single metal complex and a single binding site ligand. In instances where the ligand contains additional binding sites (i.e., a chelating ligand) or the catalyst contains more than one metal, the ratio is adjusted accordingly. By way of example, the supporting ligand BINAP contains two coordinating phosphorus atoms and thus the ratio of BINAP to catalyst is adjusted downward to about 1 to 10, preferably about 1 to 2 and most preferably about 1.2. Conversely, $Pd_2(dba)_3$ contains two palladium metal centers and the ratio of ligand to $Pd_2(dba)_3$ is adjusted upward to 1 to 40, preferably 1 to 8 and most preferably about 4.8.

In certain embodiments of the subject method, the transition metal catalyst includes one or more phosphine ligands, e.g., as a Lewis basic co-catalyst that controls the stability and electron transfer properties of the transition metal catalyst, and/or stabilizes the metal intermediates. Preferably the ligand is a stronger Lewis basic group than the heteroatom(s) of the aryl substrate. Phosphine ligands are commercially available or can be prepared by methods similar to processes known per se. The phosphines can be monodentate phosphine ligands, such as trimethylphosphine, triethylphosphine, tripropylphosphine, triisopropylphosphine, tributylphosphine, tricyclohexylphosphine, trimethyl phosphite, triethyl phosphite, tripropyl phosphite, triisopropyl phosphite, tributyl phosphite and tricyclohexyl phosphite, in particular triphenylphosphine, tri(o-tolyl)phosphine, triisopropylphosphine or tricyclohexylphosphine; or a bidentate phosphine ligand such as 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino) ethane, 1,2-bis(diisopropylphosphino)ethane, 1,2-bis(dibutyl-phosphino)ethane, 1,2-bis(dicyclohexylphosphino) ethane, 1,3-bis(dicyclohexylphosphino)propane, 1,3-bis(diisopropylphosphino)propane, 1,4-bis(diisopropyl-phosphino)-butane and 2,4-bis(dicyclohexylphosphino) pentane.

In preferred embodiments, the phosphine ligand is one (or a mix of) of $P(o-tolyl)_3$. Bis(phosphine) ligands are particularly preferred chelating supporting ligands. Suitable bis (phosphine) compounds include but are in no way limited to (±)-2,2'-4, bis(diphenylphosphino)-1,1'-binaphthyl (and separate enantiomers), (±)-2,2'-bis(di-p-tolylphosphino)-1, 1'-binaphthyl (and separate enantiomers), 1-1'-bis (diphenylphosphino)ferrocene, 1,3-bis(diphenylphosphino) propane; 1,2-bis(diphenylphosphino)benzene, and 1,2-bis (diphenylphosphino)ethane. Hybrid chelating ligands such as (±)-N,N-dimethyl-1-[2-(diphenylphosphino)ferrocenyl] ethylamine (and separate enantiomers), and (±)-(R)-1-[(S)-2-(diphenylphosphino)ferrocenyl]ethyl methyl ether (and separate enantiomers) are also within the scope of the invention.

In some instances, it may be necessary to include additional reagents in the reaction to promote reactivity of either the transition metal catalyst or activated aryl nucleus. In particular, it may be advantageous to include a suitable base. In general, a variety of bases may be used in practice of the present invention. The base is desirably capable of extraction of a proton to promote metal-amide formation. It has not been determined if deprotonation occurs prior to or after nitrogen coordination. The base may optionally be sterically hindered to discourage metal coordination of the base in those circumstances where such coordination is possible, i.e., alkali metal alkoxides. Exemplary bases include such as, for example: an alkoxides such as sodium tert-butoxide, an alkali metal amide such as sodium amide, lithium diisopropylamide or an alkali metal bis(trialkyl-silyl)amides, e.g., such as lithium bis-(trimethyl-silyl)amide or sodium bis-(trimethyl-silyl)amide, a tertiary amine (e.g. triethylamine, trimethylamine, N,N-dimethylamino-pyridine, 1,5-diazabicycl[4.3.0]nonene-5 (DBN), 1,5-diazabicycl[5.4.0]undecene-5 (DBU), alkali, alkaline earth carbonate, bicarbonate or hydroxide (e.g. sodium, magnesium, calcium, barium, potassium carbonate, hydroxide and bicarbonate). By way of example only, suitable bases include NaH, LiH, KH, $K_2CO_3$, $Na_2CO_3$, $Tl_2CO_3$, $Cs_2CO_3$, K(OtBu), Li(OtBu), Na(OtBu) K(OPh), Na(OPh), triethylamine or mixtures thereof. NaH, Na(OtBu) and $K_2CO_3$ have been found useful in a wide variety of aminopyridine bond forming reactions. Preferred bases include $Cs_2CO_3$, DBU, NaH, KOt-Bu, $KN(SiMe_3)_2$, $NaN(SiMe_3)_2$, and LiN $(SiMe_3)_2$.

Base is used in approximately stoichiometric proportions in reactions using the free amine. The present invention has demonstrated that there is no need for large excesses of base in order to obtain good yields under mild reaction conditions. No more than four equivalents and preferably no more than two equivalents are needed. Further, in reactions using the corresponding amide salt as the reagent, there may be no need for additional base.

As is clear from the above discussion, the products which may be produced by the cross-coupling reaction of this invention can undergo further reaction(s) to afford desired derivatives thereof. Such permissible derivatization reactions can be carried out in accordance with conventional procedures known in the art. For example, potential derivatization reactions include esterification, oxidation of alcohols to aldehydes and acids, N-alkylation of amides, nitrile reduction, acylation of ketones by esters, acylation of amines and the like.

Reaction Conditions

The reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants and catalyst. The reactions will usually be run at temperatures in the range of 25° C. to 300° C., more preferably in the range 25° C. to 150° C.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, derivativation with one or more of substituents of the aryl group.

Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116:2661: Kerr et al. (1993) JACS 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) PNAS 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) Tetrahedron Lett 31:5811–5814; Valerio et al. (1991) Anal Biochem 197:168–177; Bray et al. (1991) Tetrahedron Lett 32:6163–6166).

C) Divide-Couple-Recombine

In yet another embodiment, a variegated library of compounds can be provided on a set of beads utilizing the strategy of divide-couple-recombine (see, e.g., Houghten (1985) PNAS 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) PNAS 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271–280; Fodor, S. P. A. (1991) Science 251:767; Pirrung et al. (1992) U.S. Pat. No. 5,143,854; Jacobs et al. (1994) Trends Biotechnol 12:19–26). The spatial resolution of photolithography affords miniaturization. This technique can be carried out through the use protection/deprotection reactions with photolabile protecting groups.

The key points of this technology are illustrated in Gallop et al. (1994) J Med Chem 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The al reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-Oligomers

The principle of using oligonucleotides to encode combinatorial synthetic libraries was described in 1992 (Brenner et al. (1992) PNAS 89:5381–5383), and an example of such a library appeared the following year (Needles et al. (1993) PNAS 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115:2529–2531), orthogonality in synthesis is achieved by employing acid-labile protection for the coding strand and base-labile protection for the compound strand.

In an alternative approach (Nikolaiev et al. (1993) Pept Res 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) Tetrahedron Lett 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) PNAS 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) J Org Chem 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) PNAS 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention may be understood with reference to the following examples, which are presented for illustrative purposes only and which are non-limiting.

Example 1

Palladium-Catalyzed α-Arylation of Ketones

The combination of $Pd_2(dba)_3$ and Tol-BINAP or BINAP in the presence of t-BuONa catalyzes the reaction of aryl bromides with ketones to give α-aryl ketones in moderate to high yields. The regioselectivity of arylation of ketones containing α,α'-hydrogens is high: methyl>methylene >>methine. The degree of regioselectivity was found to be independent of the acidity of the α-hydrogen.

The synthesis of α-aryl ketones has received much attention over the past two decades.[1] A number of stoichiometric arylating reagents have been successfully developed for this purpose, however, their utility is decreased because each synthesis of an α-aryl ketone requires the synthesis of a different arylating reagent.[2,3] In contrast, the direct coupling of aryl halides with ketones would provide a convenient method for the synthesis of α-aryl ketones. Semmelhack, et al. have demonstrated that $Ni(COD)_2$ catalyzes the intramolecular coupling of an aryl iodide with a ketone enolate.[4] While there are reports of Pd or Ni-catalyzed intermolecular coupling reactions that afford α-aryl ketones, these methods require the use of stoichiometric amounts of tin reagents, and/or the use of enol ether, enamine or α-chloroketone derivatives instead of the ketone.[5] Thus, a general method which utilizes readily available starting materials and affords products in high regioselectivity has not been realized. Herein we describe a novel Pd-catalyzed method for the direct cross coupling of aryl halides with ketones.

We have previously shown that a mixtures of Pd$_2$(dba)$_3$ and Tol-BINAP catalyzes the coupling of sodium alkoxides (generated in situ by reaction of the alcohol with NaH) with electron-deficient aryl bromides to form aryl ethers.[7] In addition, we found that reaction of electron neutral or electron-rich aryl bromides with sodium alkoxides (generated from primary or secondary alcohols) provides the reduced arene as the major product with concomitant oxidation of the alcohol to the corresponding ketone. It was during this latter study that we unexpectedly observed small amounts of α-aryl ketone products. For example, GC analysis of the crude reaction mixture of the attempted Pd-catalyzed coupling of 1-bromo-4-t-butylbenzene with cyclohexanol showed that 1-butylbenzene was the major product along with small amounts of 2-(4-t-butylphenyl) cyclohexanone (2%), Scheme 1.8

Scheme 1

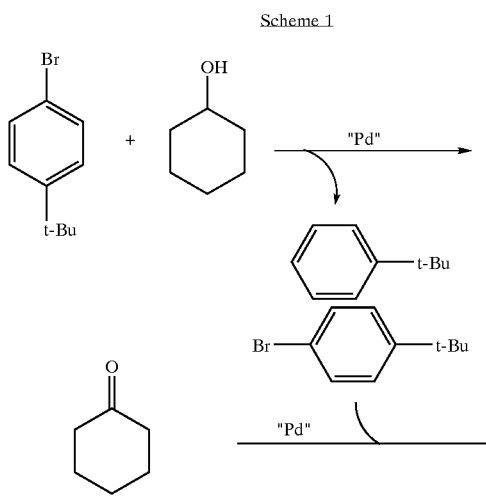

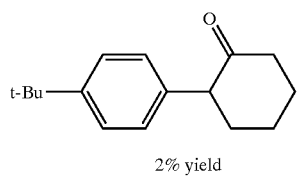

2% yield

Realizing the need for a general method for the synthesis of α-aryl ketones, we began to focus on optimizing the formation of this product. After some experimentation, we found that the combination of Pd$_2$(dba)$_3$ and Tol-BINAP or BINAP in the presence of NaOt-Bu effectively catalyzes the desired coupling reaction, eq 1.[9] We found that 3 mol % Pd and 3.6 mol % ligand was sufficient to obtain complete conversion of starting aryl bromide. Under the conditions employed, α-aryl ketones were not formed in the absence of catalyst. A broad study on; the generality of this reaction was undertaken and the results are shown in Table 1.[10,11]

(1)

TABLE 1

Palladium-catalyzed coupling of aryl bromides with ketones.

| entry | aryl bromide | ketone |
|---|---|---|
| 1 | 3-bromo-benzaldehyde 1,3-dioxolane | 2-methyl-3-pentanone (Me-CO-CH(Me)-Me) |
| 2 | | 1-phenyl-2-phenyl-propan-1-one-like (Me-CO-CH(Ph)-Ph) |
| 3 | 4-bromobiphenyl | 2-methyl-3-pentanone (Me-CH2-CO-CH(Me)-Me) |

TABLE 1-continued

Palladium-catalyzed coupling of aryl bromides with ketones.

| entry | | | | |
|---|---|---|---|---|
| 4 | 3-bromoanisole | | propiophenone | |
| 5 | 4-bromo-N-(diphenylmethylene)aniline | | pinacolone (Me-CO-t-Bu) | |
| 6 | | | 2-hexanone (Me-CO-n-Bu) | |
| 7 | 4-bromobenzonitrile | | acetylferrocene | |
| 8 | 4-tert-butylbromobenzene | | cyclohexanone | |
| 9 | 4-bromo-N,N-diethylbenzamide | | 1,1-diphenylacetone (Me-CO-CHPh₂) | |
| 10 | 1-bromo-3,5-dimethylbenzene | | pinacolone | |
| 11 | 1-bromo-4-chlorobenzene | | pinacolone | |
| 12 | 2-bromo-p-xylene | | 1-(1,3-benzodioxol-5-yl)ethanone | |

| entry | ketone:ArBr | ligand | product | monoarylation diarylation | yield (%)[b] |
|---|---|---|---|---|---|
| 1 | 1.2 | Tol-BINAP | [product: 1-(3-(1,3-dioxolan-2-yl)phenyl)-3-methyl-2-butanone] | 13:1 | 76 |

TABLE 1-continued
Palladium-catalyzed coupling of aryl bromides with ketones.
| | | | | | |
|---|---|---|---|---|---|
| 2 | 1.2 | Tol-BINAP | 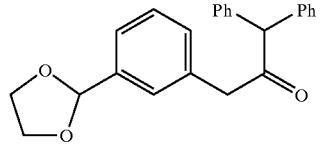 | — | 72 |
| 3 | 1.2 | Tol-BINAP | 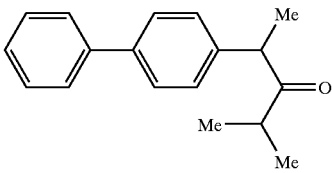 | — | 93 |
| 4 | 1.2 | BINAP | 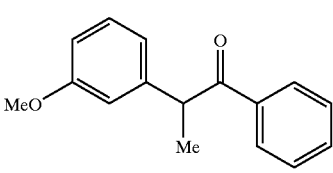 | — | 91 |
| 5 | 1.2 | Tol-BINAP | 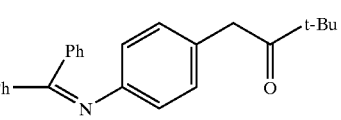 | — | 78 |
| 6 | 1.2<br>2.0 | BINAP<br>BINAP | 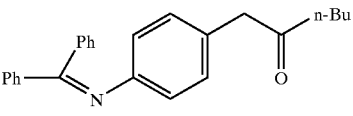 | 10:1<br>28:1 | 64[c]<br>63[d] |
| 7 | 1.2<br>2.0 | BINAP<br>BINAP | 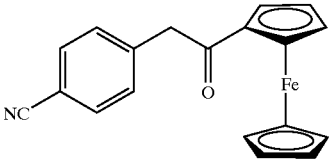 | 20:1<br>27:1 | 64<br>75 |
| 8 | 1.2<br>2.0 | Tol-BINAP<br>Tol-BINAP | 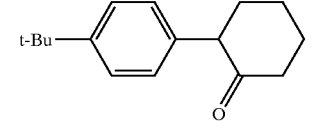 | 30:1<br>33:1 | 67<br>83 |
| 9 | 1.2 | Tol-BINAP | 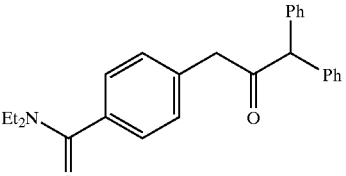 | — | 69 |
| 10 | 1.2 | Tol-BINAP | 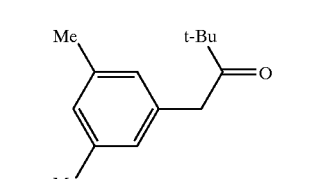 | — | 93 |

TABLE 1-continued

Palladium-catalyzed coupling of aryl bromides with ketones.

| | | | | | |
|---|---|---|---|---|---|
| 11 | 1.2 | Tol-BINAP |  | 7:1 | 71 |
| | 2.0 | Tol-BINAP | | 16:1 | 88 |
| 12 | 1.2 | BINAP |  | — | 84[e] |

[a]Reactions conditions are as follow: 1.0 equiv of ArBr, 1.2 or 2.0 equiv of ketone, 1.3 equiv of NaCl—Bu, 1.5 mol % of $Pd_2(dba)_3$, 3.6 mol % of ligand in THF (ArBr = 0.17 M), 70° C.
[b]Yields refer to the average of isolated yield for two runs.
[c]Isolated as a 20:1 mixture of regioisomers.
[d]Isolated as a 16:1 mixture of regioisomers.
[e]Reaction performed using 5 mol % Pd and 6 mol % BINAP.

As illustrated in Table 1, the Pd-catalyzed arylation of ketones provides a general method for obtaining a wide variety of α-aryl ketones. The mild reaction conditions are compatible with a wide variety of functional groups including nitrites, ethers, imines, amides, aryl chlorides and acetals. Reaction times are typically 4–12 h using 3 mol % palladium and 3.6 mol % ligand. Reaction of 2-bromo-pxylene with 3',4'-(methylenedioxy)-acetophenone required 5 mol % Pd and 18 h for complete conversion of the starting aryl halide (entry 12).[12]

The regioselectivity of the Pd-catalyzed arylation of ketones is quite remarkable. Ketones containing α,α'-hydrogens are preferentially arylated at the least hindered side (methyl>methylene>>methine). For example, NMR analysis of the crude reaction mixture of the coupling of 2-(3-bromophenyl)-1,3-dioxolane with 3-methyl-2-butanone showed no evidence of arylation at the methine carbon and a 13:1 mixture of mono-arylation:diarylation of the methyl ketone (entry 1). Likewise, NMR analysis of the crude reaction mixture of the coupling of 4-bromobiphenyl with 2-methyl-3-pentanone revealed that coupling occurred exclusively at the methylene carbon (entry 3). Coupling of 1,1-diphenylacetone to 2-(3-bromophenyl)-1,3-dioxolane (entry 2) or N,N-diethyl-p-bromobenzamide (entry 9) occured exclusively at the methyl group despite the significantly greater acidity of the methine proton.

Further examples illustrating the high degree of regioselectivity can be seen in the reaction of N-diphenylmethylene-4-bromoaniline with 2-hexanone (entry 6). Although the degree of regioselectivity (arylation of methyl vs methylene) decreased slightly upon increasing the relative concentration of ketone, the amount of diarylation of the methyl ketone decreased from 9% to 3%, as determined by NMR analysis of the crude reaction mixture. Diarylation was observed only for methyl ketones which are relatively unhindered at the α'-position. Thus, no diarylation was observed for 1,1-diphenyl acetone (entries 2 and 9), 3-methyl-2-butanone (entry 1) and pinacolone (entries 5 and 10). In addition, no diarylation was observed in the coupling of 2-bromo-pxylene with 3',4'-(methylenedioxy)-acetophenone, presumably because of the steric hindrance provided by the ortho-methyl group (entry 12). Arylation of methine carbons was not observed under these conditions. Attempts at coupling 1-bromo-4-t-butylbenzene with 2,6-dimethylcyclohexanone gave, after 14 h, <2% of the desired 2,6-dimethyl-2-(4-t-butylphenyl)cyclohexanone.[13]

Although little mechanistic information has been obtained about the Pd-catalyzed arylation of ketones, we believe that the reaction proceeds via the mechanism shown in Scheme 2. Oxidative addition of the $Pd(0)L_n$ with the aryl bromide affords the Pd(II) organometallic intermediate A. Ligand substitution of the bromide by the sodium enolate provides the Pd(II) organometallic intermediate B or C. Given the high degree of regioselectivity of arylation, we believe that deprotonation of the ketone occurs prior to coordination to the Pd center. Finally, reductive elimination from intermediate B or C provides the α-aryl ketone and regenerates the $Pd(0)L_n$ catalyst. That C doesn't decompose via a β-hydride elimination pathway (in cases where both α-carbons are substituted) further attests to the ability of BINAP and Tol-BINAP to render such complexes four-coordinate.

Scheme 2

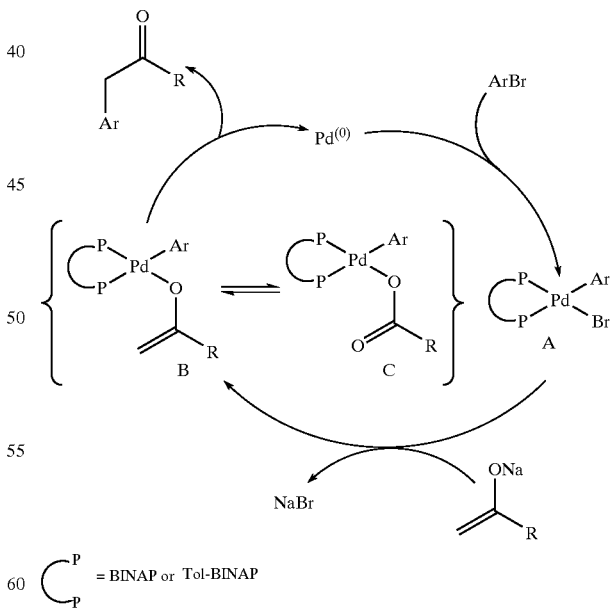

In summary, we have developed a general method for the direct synthesis of α-aryl ketones from ketones and aryl bromides. This process displays good functional group tolerance and high regioselectivity. Efforts to extend the substrate scope to other classes of substrates such as esters and amides, and to develop an asymmetric variant are currently under progress.

REFERENCES AND NOTES FOR EXAMPLE 1

1. Abramovitch, R. A.; Barton, D. H. R.; Finet, J.-P. *Tetrahedron* 1988, 44, 3039–3071.
2. (a) Morgan, J.; Pinhey, J. T.; Rowe, B. A. *J. Chem. Soc. Perkin Trans. I* 1993, 1677–1681. (b) Ryan, J. H.; Stang, P. J. *Tetrahedron Lett.* 1997, 38, 5061–5064. (c) Barton, D. H. R.; Finet, J.-P., Giannoti, C.; Halley, F. *J. Chem. Soc., Perkin Trans. I* 1987, 1005–1007. (d) Mino, T.; Matsuda, T.; Maruhashi, K.; Yamashita, M. *Organometallics* 1987, 16, 3241–3242. (e) Dell'erba, C.; Novi. M.; Petrillo, G.; Tavani, C. *Tetrahedron* 1993, 49, 235–242. (f) Rathke, M. W.; Vogiazoglou, D. *J. Org. Chem.* 1987, 52, 3697–3698.
3. Arylation of ketones via $S_{RN}1$ aromatic substitution has been succussfully employed; see Norris, R. K. In *Comprehensive Organic Synthesis*; Trost, B. M.; Fleming, I.; Semmelhack, M. F., Ed; Pergamon Press: New York, 1991; Vol 4, Ch 2.2 and references cited therein.
4. Semmelhack, M. F.; Chong. B. P.; Stauffer, R. D.; Rogerson, T. D.; Chong, A.; Jones, L., D. *J. Am. Chem. Soc.* 1975, 97, 2507–2516.
5. (a) Durandetti, M.; Sibille, S.; Nédélee J.-Y.; Périchon, J. *Synthetic Commun.* 1994, 24, 145–151. (b) Sakakura, R.; Hara, M.; Tanaka, M. *J. Chem. Soc., Perkin Trans. I* 1994, 283–288. (c) Negishi, E.-i.; Akiyoshi, K. *Chem. Lett.* 1987, 1007. (d) Kosugi, M.; Hagiwara, I.; Sumiya, T.; Migita, T. *Bull. Chem. Soc. Jpn.* 1984, 57, 242–246. (e) Kuwajima, I.; Urabe. H. *J. Am. Chem. Soc.* 1982, 104, 6831–6833. (f) Heck, R. F. *J. Am. Chem. Soc.* 1968, 90, 5535–5538.
6. For examples of Pd or Ni-catalyzed coupling of aryl halides with esters or ester equivalents see: (a) Galarini, R.; Musco, A.; Pontellini, R. *J. Mol. Cat.* 1992, 72, L11–L13. (b) Carfagna, C.; Musco, A.; Sallese, G. *J. Org. Chem.* 1991, 56, 261–263. (c) Orsin, R.; Pelizzoni, F.; Vallarino, L. M. *J. Organomet. Chem.* 1989, 367, 375–382. (d) Fauvarque, J. F.; Jutand, A. *J. Organomet. Chem.* 1979, 177, 273–281. (e) Millard, A. A.; Rathke, M. W. *J. Am. Chem. Soc.* 1977, 99, 4833–4835. For examples of Pd-catalyzed intramolecular coupling of aryl halides with β-dicarbonyl compounds see: Ciufolini; M. A.; Browne, M. E. *Tetrahedron Left.,* 1987, 28, 171–174; Ciufolini; M. A.; Qi, H.-B.; Browne, M. E. *J. Org. Chem.* 1988, 53, 4151–4153.
7. (a) Palucki, M.; Wolfe. J. P.; Buchwaid, S. L. *J. Am. Chem. Soc.* 1996, 118, 10333–10334. (b) Palucki. M.; Wolfe. J. P.; Buchwald. S. L. *J. Am. Chem. Soc.* 1997, 119, 3395–3396.
8. Palucki. M.; Buchwald. S. L. Unpublished results.
9. Tol-BINAP=2,2'-bis(di-p-tolylphosphino)-1,1'-binaphthyl, BINAP=2,2'-bis(diphenylphosphino)-1,1'-binaphthyl.
10. Representative procedure In a fume hood, an oven-dried Schlenk tube containing a stir bar was charged with $Pd_2dba_3$ (6.9 mg, 0.0075 mmol), Tol-BINAP (0.018 mmol, 0.018 mmol), and NaOt-Bu (65 mg, 0.65 mmol). The Schlenk tube was evacuated and back filled with argon. THF (2 mL) was added followed by 2-(3-bromophenyl)-1,3-dioxolane (76 μL, 0.5 mmol), 3-methyl-2-butanone (64 μL, 0.60 mmol), and additional THF (1 mL). The resulting red mixture was heated under argon in a 70° C. oil bath until the starting halide had been consumed as judged by GC analysis. The Schlenk tube was cooled to room temperature, and diethyl ether (25 mL) and $H_2O$ (25 mL) were added. The aqueous layer was separated and extracted with diethyl ether (25 mL). The organic layers were combined, washed with brine (40' mL), dried over $MgSO_4$, filtered, and concentrated. The crude product was purified by flash chromatography on silica gel to give 90 mg (76% yield) of a colorless oil.
11. Other ligands examined in the Pd-catalyzed coupling of cyclohexanone with 1-bromo-4-t-butylbenzene include tri-o-tolylphosphine, 1,2-bis(diphenylphosphino)ethane (DPPE), 1,2-bis(diphenylphosphino)propane (DPPP), and 1,1'-bis(diphenylphosphino)ferrocene (DPPF). The use of DPPF provided the desired product in 50% yield (GC), however, t-butylbenzene was formed in 25% yield (GC). Use of Tol-BINAP afforded >90% yield (GC, uncorrected for response factors) of the desired product and <1% yield (GC) of t-butylbenzene.
12. The reaction of 4-chloroacetophenone and of 4-methoxyacetophenoe with 2-bromo-p xylene prodeeced to only ca. 90% conversion of the starting aryl halide using 5 mol % Pd and 6 mol % ligand. The reaction of 2-bromo-p-xylene with 3-methyl-2-butanone using 7 mol % Pd and 8.4 mol % ligand gave complete conversion of the starting aryl halide, but the isolated product was <95% pure.
13. Determined by GC and GC/MS analysis of the crude reaction mixture.
14. Wolfe, J. P.; Wagaw, S.; Buchwald, S. L. *J. Am. Chem. Soc.* 1996, 118, 7215–7216.

General Considerations. THF was distilled under argon from the sodium ketyl of benzophenone. 3-Methyl-2-butanone, 2-propiophenone, 2-hexanone, acetylferrecone, 1,1-diphenylacetone, 4,4-dimethyl-2-pentanone, 3',4'-(methylenedioxy)-acetophenone, 2-(3-bromophenyl)-1,3-dioxolane, 4-bromobiphenhyl, 4-bromobenzonitrile, 5-bromo-m-xylene and 2-bromo-pxylene were purchased from Aldrich chemical company and used without further purification. 3-bromoanisole, 1-bromo-4-t-butylbenzene, 4-bromochlorobenzene were purchased from Lancaster Synthesis Inc., and used without further purification. Pinacolone was purchased from Aldrich chemical company and filtered through a plug of alumina prior to use. Cyclohexanone was purchased from Mallinckrodt Inc. and distilled over 4 Å molecular sieves. Sodium-tert-butoxide was purchased from Aldrich chemical company and stored in a Vacuum Atmospheres glovebox. For purposes of convenience, small amounts of sodium-tert-butoxide were stored in a dessicator for up to 1 week and weighed in air. (S)-(−)2,2'-bis(di-p-tolylphosphino)-1,1'-binaphthyl) (Tol-BINAP), (R)-(+)-2,2'-bis(di-p-tolylphosphino)-1,1'-binaphthyl) (Tol-BINAP), rac-2,2,'-bis(diphenylphosphino)-1,1'-binaphthyl (BINAP), and $Pd_2(dba)_3$ were purchased from Strem chemical company and used without further purification. Silica gel chromatographic purifications were performed by flash chromatography using E. M. Science Kieselgel 60 (230400 mesh) silica packed in columns. Yields refer to isolated yields of compounds of greater than 95% purity as determined by capillary gas chromatography (GC), and proton Nuclear Magnetic Resonance spectroscopy ($^1H$ NMR) analysis. New compounds were also characterized by elemental analysis (E & R Analytical Laboratory, Inc). Yields reported in this section refer to a single experiment whereas those reported in Table 1 are an average of two or more runs. $^1H$ NMR spectra were recorded on a Varian XL-300 or a Bruker AC-250 Fourier Transform spectrometer with chemical; shifts reported in parts per million (ppm) relative to tetramethylsilane. $^{13}C$ NMR were recorded on a Bruker AC-250 Fourier Transform spectrometer with complete proton decoupling with chemical shifts reported in ppm relative to chloroform-d. Gas chromatography analyses were performed on a Hewlett Packard 5890 Series II instrument and a Hewlett Packard 3392A integrator with a FID detector and a Hewlett Packard 25 m×0.2 mm i.d. HP-1 capillary column.

Example 2

Synthesis of 1-(3-benzaldehyde ethylene acetal)-3-methyl-2-butanone

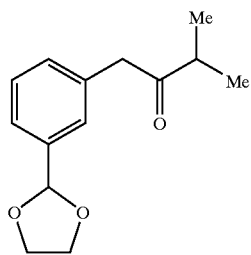

An oven-dried Schlenk tube containing a stir bar was charged with $Pd_2(dba)_3$ (6.9 mg, 0.0075 mmol, 1.5 mol %), ligand (0.018 mmol, 3.6 mol %), and NaOt-Bu (65 mg, 0.65 mmol). The Schlenk tube was evacuated and back filled with argon. THF (2 mL) was added followed by aryl halide (0.5 mmol), ketone (0.6 mmol or 1.0 mmol), and additional THF (1 mL). The resulting red mixture was heated under argon at 70° C. until the starting halide had been consumed as judged by GC analysis. The Schlenk tube was cooled to room temperature, and diethyl ether (25 mL) and $H_2O$ (25 mL) were added. The aqueous layer was separated and extracted with diethyl ether (25 mL). The organic layers were combined, washed with brine (40 mL), dried over $MgSO_4$, filtered, and concentrated. The crude product was then purified by flash chromatography on silica gel. Using 0.6 mmol of ketone and Tol-BINAP gave 90 mg (76% yield) of a colorless oil. $^1$H NMR (CDCl$_3$, 250 MHz) δ 7.31–7.36 (m, 3H), 7.19–7.23 (m, 1H), 5.80 (s, 1H), 4.08–4.15 (m, 2H), 3.99–4.06 (m, 2H), 3.76 (s, 2H), 2.72 (hp, J=6.9 Hz, 1H), 1.09 (d, J=6.9 Hz, 6H); $^{13}$C NMR (CDCl$_3$, 250 MHz) 8211.4, 138.3, 134.6, 130.2, 128.5, 127.4, 124.9, 103.5, 65.2, 47.5, 40.1, 18.2; IR (neat, cm$^{-1}$) 2958, 1711, 1611. Anal Calcd for $C_{14}H_{22}O_3$: C, 71.77; H, 7.74. Found: C, 71.52; H, 7.54.

Example 3

Synthesis of 1-(3-benzaldehyde ethylene acetal)-3,3-diphenylacetone

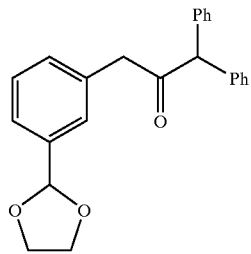

An oven-dried Schlenk tube containing a stir bar was charged with $Pd_2(dba)_3$ (6.9 mg, 0.0075 mmol, 1.5 mol %), ligand (0.018 mmol, 3.6 mol %), and NaOt-Bu (65 mg, 0.65 mmol). The Schlenk tube was evacuated and back filled with argon. THF (2 mL) was added followed by aryl halide (0.5 mmol), ketone (0.6 mmol or 1.0 mmol), and additional THF (1 mL). The resulting red mixture was heated under argon at 70° C. until the starting halide had been consumed as judged by GC analysis. The Schlenk tube was cooled to room temperature, and diethyl ether (25 mL) and $H_2O$ (25 mL) were added. The aqueous layer was separated and extracted with diethyl ether (25 mL). The organic layers were combined, washed with brine (40 in L), dried over $MgSO_4$, filtered, and concentrated. The crude product was then purified by flash chromatography on silica gel. Using 0.6 mmol of ketone and Tol-BINAP gave 139 mg, (77% yield) of a yellow solid. mp 99.1–100° C.; $^1$H NMR (CDCl$_3$, 250 MHz) δ 7.27–7.39 (m, 9H), 7.15–7.18 (m, 5H), 5.79 (s, 1H), 5.21 (s, 1H), 4.08–4.11 (m, 2H), 4.02–4.06 (m, 2H), 3.81 (s, 2H); $^{13}$C NMR (CDCl$_3$, 250 MHz) δ 205.2, 138.4, 137.9, 134.1, 130.2, 129.0, 128.5, 127.5, 127.1, 125.1, 103.4, 65.1, 62.9, 49.3; IR (KBr, cm$^{-1}$) 2892, 1717, 1492, 1454. Anal Calcd for $C_{24}H_{22}O_3$: C, 80.42; H, 6.19. Found: C, 80.36; H, 6.06.

Example 4

Syntheisi of 2-(4-biphenyl)-4-methyl-3-pentanone

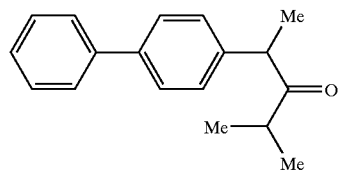

An oven-dried Schlenk tube containing a stir bar was charged with $Pd_2(dba)_3$ (6.9 mg, 0.0075 mmol, 1.5 mol %), ligand (0.018 mmol, 3.6 mol %), and NaOt-Bu (65 mg, 0.65 mmol). The Schlenk tube was evacuated and back filled with argon. THF (2 mL) was added followed by aryl halide (0.5 mmol), ketone (0.6 mmol or 1.0 mmol), and additional THF (1 mL). The resulting red mixture was heated under argon at 70° C. until the starting halide had been consumed as judged by GC analysis. The Schlenk tube was cooled to room temperature, and diethyl ether (25 mL) and $H_2O$ (25 mL) were added. The aqueous layer was separated and extracted with diethyl ether (25 mL). The organic layers were combined, washed with brine (40 mL), dried over $MgSO_4$, filtered, and concentrated. The crude product was then purified by flash chromatography on silica gel. Using 0.6 mmol of ketone and Tol-BINAP gave 117 mg (93% yield) of a white solid. mp 48–49° C.; $^1$H NMR (CDCl$_3$, 250 MHz) δ 7.52–7.58 (m, 4H), 7.41 (t, J=7.0 Hz, 2H), 7.29–7.34 (m, 3H), 3.96 (q, J=6.9 Hz, 1H), 2.72 (hp, J=6.9 Hz: 1H), 1.40 (d, J=6.9 Hz, 3H), 1.09 (d, J=6.9 Hz, 3H), 0.94 (d, J=6.9 Hz, 3H); $^{13}$C NMR (CDCl$_3$, 250 MHz) δ 214.4, 140.7, 140.0, 128.7, 128.3, 127.5, 127.3, 126.9, 50.7, 39.3, 19.1, 18.3, 18.2; IR (KBr, cm$^{-1}$) 1708, 1488, 1453, 1380. Anal Calcd for $C_{18}H_{20}O$: C, 85.67; H, 7.99. Found: C, 85.95; H, 8.00.

Example 5

Synthesis of 2-(3-methoxyphenyl)-propiophenone

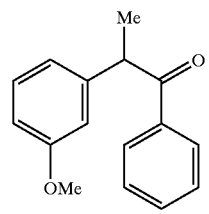

An oven-dried Schlenk tube containing a stir bar was charged with $Pd_2(dba)_3$ (6.9 mg, 0.0075 mmol, 1.5 mol %), ligand (0.018 mmol, 3.6 mol %), and NaOt-Bu (65 mg, 0.65 mmol). The Schlenk tube was evacuated and back filled with argon. THF (2 mL) was added followed by aryl halide (0.5 mmol), ketone (0.6 mmol or 1.0 mmol), and additional THF (1 !mL). The resulting red mixture was heated under argon at 70° C. until the starting halide had been consumed as judged by GC analysis. The Schlenk tube was cooled to room temperature, and diethyl ether (25 mL) and $H_2O$ (25 mL) were added. The aqueous layer was separated and extracted with diethyl ether (25 mL). The organic layers were combined, washed with brine (40 mL), dried over $MgSO_4$, filtered, and concentrated. The crude product was then purified by flash chromatography on silica gel. Using 0.6 mmol of ketone and BINAP gave 107 mg (89% yield) of a colorless oil. $^1$H NMR ($CDCl_3$, 250 MHz) δ 7.92–7.96 (m, 2H), 7.31–7.44 (m, 3H), 7.19 (t, J=7.0 Hz, 1H), 6.82–6.88 (m 2H), 6.72 (dd, J=8.3, 2.3 Hz, H), 4.64 (q, J=6.8 Hz, 1H), 3.73 (s, 3H), 1.52 (d, J=6.8 Hz, 3H); $^{13}$C NMR ($CDCl_3$, 250 MHz) 5200.1, 150.0, 143.0, 136.6, 132.7, 129.9, 128.7, 128.4, 120.2, 113.5, 112.2, 55.1, 47.9, 19.3; IR (neat, $cm^{-1}$) 2975, 2932, 1682, 1597, 1583. Anal Calcd for $C_{16}H_{602}$: C, 79.97; H, 6.71. Found: C, 79.89; H, 6.62.

Example 6

Syntheis of 1-(4-N-diphenylmethyleneaniline)-3,3-dimethyl-2-butanone

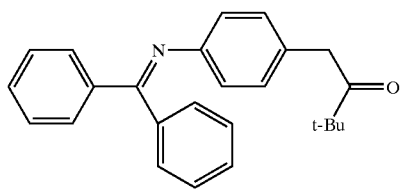

An oven-dried Schlenk tube containing a stir bar was charged with $Pd_2(dba)_3$ (6.9 mg, 0.0075 mmol, 1.5 mol %), ligand (0.018 mmol, 3.6 mol %), and NaOt-Bu (65 mg, 0.65 mmol). The Schlenk tube was evacuated and back filled with argon. THF (2 mL) was added followed by aryl halide (0.5 mmol), ketone (0.6 mmol or 1.0 mmol), and additional THF (1 mL). The resulting red mixture was heated under argon at 70° C. until the starting halide had been consumed as judged by GC analysis. The Schlenk tube was cooled to room temperature, and diethyl ether (25 mL) and $H_2O$ (25 mL) were added. The aqueous layer was separated and extracted with diethyl ether (25 mL). The organic layers were combined, washed with brine (40 mL), dried over $MgSO_4$, filtered, and concentrated. The crude product was then purified by flash chromatography on silica gel. Using 0.6 mmol of ketone and Tol-BINAP gave 134 mg (76% yield) of a yellow solid. mp 71.2–72° C.; $^1$H NMR ($CDCl_3$, 250 MHz) δ 7.72 (d, J=6.9 Hz, 2H), 7.36–7.46 (m, 2H), 7.214–7.26 (m, 4H), 7.09–7.11 (m, 2H), 6.95 (d, J=8.2 Hz, 2H), 6.65 (d, J=8.2 Hz, 2H), 3.67 (s, 2H), 1.13 (s, 9H); $^{13}$C NMR ($CDCl_3$, 250 MHz) δ 212.8, 168.1, 139.7, 136.2, 130.6, 129.6, 129.2, 128.5, 128.1, 127.8, 121.0, 44.5, 43.0, 26.5; IR (KBr, $cm^{-1}$) 2961, 1704, 1626, 1445. Anal Calcd for $C_{25}H_{25}NO$: C, 84.47; H, 7.09. Found: C, 84.28; H, 7.10.

Example 7

Synthesis of 1-(4-N-diphenylmethyleneaniline)-2-hexanone

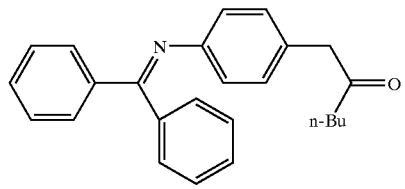

An oven-dried Schlenk tube containing a stir bar was charged with $Pd_2(dba)_3$ (6.9 mg, 0.0075 mmol, 1.5 mol %), ligand (0.018 mmol, 3.6 mol %), and NaOt-Bu (65 mg, 0.65 mmol). The Schlenk tube was evacuated and back filled with argon. THF (2 mL) was added followed by aryl halide (0.5 mmol), ketone (0.6 mmol or 1.0 mmol), and additional THF (1 mL). The resulting red mixture was heated under argon at 70° C. until the starting halide had been consumed as judged by GC analysis. The Schlenk tube was cooled to room temperature, and diethyl ether (25 mL) and $H_2O$ (25 mL) were added. The aqueous layer was separated and extracted with diethyl ether (25 mL). The organic layers were combined, washed with brine (40: mL), dried over $MgSO_4$, filtered, and concentrated. The crude product was then purified by flash chromatography on silica gel. Using 0.6 mmol of ketone and BINAP gave 113 mg (64% yield) of a yellow oil (36:1 mixture of regioisomers). $^1$H NMR ($CDCl_3$, 250 MHz)° 7.7 (d, 2H, J=8.3 Hz), 7.35–7.45 (m, 3H), 7.21–7.25 (m, 3H), 7.08–7.12 (m, 2H), 6.97 (d, 2H, J=8.3 Hz), 6.68 (d, J=8.3 Hz, 2H), 3.52 (s, 2H), 2.33 (t, J=7.3 Hz, 2H), 1.47 (quintent, J=7.3 Hz, 2H), 1.18 (quintent, J=7.2 Hz, 2H), 0.84 (t, J=7.3 Hz, 3H); $^{13}$C NMR ($CDCl_3$, 250 MHz) δ 208.7, 168.3, 150.1, 139.6, 136.2, 130.6, 129.4, 129.3, 129.1, 128.5, 128.1, 127.8, 121.2, 49.8, 41.1, 25.7, 22.1, 13.7; IR (neat, $cm^{-1}$) 2957, 1712, 1620, 1503, 1318. Anal Calcd for $C_{25}H_{25}NO$: C, 84.47; H, 7.09. Found: submitted for analysis.

Example 8

Synthesis of 1-(4-benzonitrile)acetylferrocene

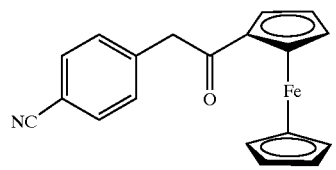

An oven-dried Schlenk tube containing a stir bar was charged with $Pd_2(dba)_3$ (6.9 mg, 0.0075 mmol, 1.5 mol %), ligand (0.018 mmol, 3.6 mol %), and NaOt-Bu (65 mg, 0.65 mmol). The Schlenk tube was evacuated and back filled with argon. THF (2 mL) was added followed by aryl halide (0.5 mmol), ketone (0.6 mmol or 1.0 mmol), and additional THF (1 mL). The resulting red mixture was heated under argon at 70° C. until the starting halide had been consumed as judged by GC analysis. The Schlenk tube was cooled to room temperature, and diethyl ether (25 mL) and $H_2O$ (25 mL) were added. The aqueous layer was separated and extracted with diethyl ether (25 mL). The organic layers were combined, washed with brine (40 mL), dried over $MgSO_4$, filtered, and concentrated. The crude product was then purified by flash chromatography on silica gel. Using 1.0 mmol of ketone and rac-BINAP gave 131 mg (80% yield) of a orange solid. mp 112.5–113.5° C.; $^1$H NMR (CDCl$_3$, 250 MHz) δ 7.62 (d, J=8.2 Hz, 2H), 7.41 (d, J=8.2 Hz, 2H), 4.82 (t, J=18 Hz, 2H), 4.56 (t, J=1.8 Hz, 2H), 4.16 (s, 4H), 4.05 (s, 3H); $^{13}$C NMR (CDCl$_3$, 250 MHz) δ 199.8, 140.3, 132.0, 130.2, 118.6, 110.6, 78.3, 72.7, 69.8, 69.5, 46.1; IR (KBr, cm$^{-1}$) 1654, 1500, 1454, 1410. Anal Calcd for C$_{19}$H$_{15}$NOFe: C, 69.33; H, 4.59. Found: submitted for analysis.

Example 9
Synthesis of 2-(4-t-btuylphenyl)-cyclohexanone

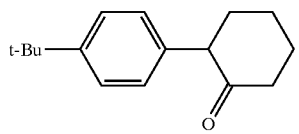

An oven-dried Schlenk tube containing a stir bar was charged with Pd$_2$(dba)$_3$ (6.9 mg, 0.0075 mmol, 1.5 mol %), ligand (0.018 mmol, 3.6 mol %), and NaOt-Bu (65 mg, 0.65 mmol). The Schlenk tube was evacuated and back filled with argon. THF (2 mL) was added followed by aryl halide (0.5 mmol), ketone (0.6 mmol or 1.0 mmol), and additional THF (1 mL). The resulting red mixture was heated under argon at 70° C. until the starting halide had been consumed as judged by GC analysis. The Schlenk tube was cooled to room temperature, and diethyl ether (25 mL) and H$_2$O (25 mL) were added. The aqueous layer was separated and extracted with diethyl ether (25 mL). The organic layers were combined, washed with brine (40 mL), dried over MgSO$_4$, filtered, and concentrated. The crude product was then purified by flash chromatography on silica gel. Using 1.0 mmol of ketone and Tol-BINAP gave 98 mg (85% yield) of a white solid. mp 80–81° C.; $^1$H NMR (CDCl$_3$, 250 MHz) δ 7.36 (d, J=8.3 Hz, 2H), 7.07 (d, J=8.3 Hz, 2H), 3.58 (dd, J=11.6, 5.3 Hz, 1H), 2.43–2.51 (m, 2H), 2.21–2.23 (m, 2H), 1.76–2.13 (m, 4H), 1.31 (s, 9H); $^{13}$C NMR (CDCl$_3$, 250 MHz) δ 210.3, 149.4, 135.6, 128.0, 125.2, 56.8, 42.1, 35.0, 34.4, 31.3, 27.8, 25.2; IR (neat, cm$^{-1}$) 2862, 2958, 1699.

Example 10
Synthesis of 3-(4-diphenylaminobenzamide)-1,1-diphenylacetone

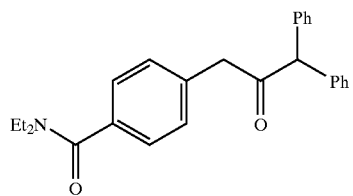

An oven-dried Schlenk tube containing a stir bar was charged with Pd$_2$(dba)$_3$ (6.9 mg, 0.0075 mmol, 1.5 mol %), ligand (0.018 mmol, 3.6 mol %), and NaOt-Bu (65 mg, 0.65 mmol). The Schlenk tube was evacuated and back filled with argon. THF (2 mL) was added followed by aryl halide (0.5 mmol), ketone (0.6 mmol or 1.0 mmol), and additional THF (1 mL). The resulting red mixture was heated under argon at 70° C. until the starting halide had been consumed as judged by GC analysis. The Schlenk tube was cooled to room temperature, and diethyl ether (25 mL) and H$_2$O (25 mL) were added. The aqueous layer was separated and extracted with diethyl ether (25 mL). The organic layers were combined, washed with brine (40 mL), dried over MgSO$_4$, filtered, and concentrated. The crude product was then purified by flash chromatography on silica gel. Using 0.6 mmol of ketone and Tol-BINAP gave 140 mg (73% yield) of a viscous yellow oil. $^1$H NMR (CDCl$_3$, 250 MHz) δ 7.27–7.34 (m, 8H), 7.12–7.22 (m, 6H), 5.20 (s, 1H), 3.81 (s, 2H), 3.51 (bs, 2H), 3.24 (bs, 2H), 1.23 (bs, 3H), 1.10 (bs, 3H); $^{13}$C NMR (CDCl$_3$, 250 MHz) δ 205.1, 170.9, 137.8, 135.9, 135.0, 129.5, 128.9, 128.6, 127.2, 126.6, 63.1, 49.1; IR (neat, cm$^{-1}$)2972, 1716, 1622, 1454, 1428. Anal Calcd for C$_{26}$H$_{27}$N$_2$O: C, 81.01; H, 7.06. Found: C, 81.28; H, 6.85.

Example 11
Synthesis of 1-(3,5-dimethylphenyl)3,3-dimethyl-2-butanone

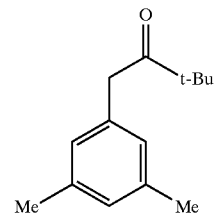

An oven-dried Schlenk tube containing a stir bar was charged with Pd$_2$(dba)$_3$ (6.9 mg, 0.0075 mmol, 1.5 mol %), ligand (0.018 mmol, 3.6 mol %), and NaOt-Bu (65 mg, 0.65 mmol).

The Schlenk tube was evacuated and back filled with argon. THF (2 mL) was added followed by aryl halide (0.5 mmol), ketone (0.6 mmol or 1.0 mmol), and additional THF (1 mL). The resulting red mixture was heated under argon at 70° C. until the starting halide had been consumed as judged by GC analysis. The Schlenk tube was cooled to room temperature, and diethyl ether (25 mL) and H$_2$O (25 mL) were added. The aqueous layer was separated and extracted with diethyl ether (25 mL). The organic layers were combined, washed with brine (40 mL), dried over MgSO$_4$, filtered, and concentrated. The crude product was then purified by flash chromatography on silica gel. Using 0.6 mmol of ketone and Tol-BINAP gave 94 mg (92% yield) of a colorless oil. $^1$H NMR (CDCl$_3$, 250 MHz) δ 7.24 (s, 2H), 6.77 (s, 2H), 3.72 (s, 2H), 2.29 (s, 6H), 1.20 (s, 9H); $^{13}$C NMR (CDCl$_3$, 250 MHz) δ 212.9, 137.7, 34.7, 128.2, 127.3, 44.6, 43.1, 26.4, 21.2; IR (neat, cm$^{-1}$) 2968, 1712, 1607, 1478. Anal Calcd for C$_{14}$H$_{20}$O: C, 82.30; H, 9.87. Found: C, 82.08; H, 9.79.

Example 12
Synthesis of 1-(4-chlorophenyl)-4,4-dimethyl-2-pentanone

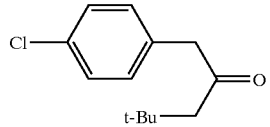

An oven-dried Schlenk tube containing a stir bar was charged with Pd$_2$(dba)$_3$ (6.9 mg, 0.0075 mmol, 1.5 mol %), ligand (0.018 mmol, 3.6 mol %), and NaOt-Bu (65 mg, 0.65 mmol). The Schlenk tube was evacuated and back filled with argon. THF (2 mL) was added followed by aryl halide (0.5 mmol), ketone (0.6 mmol or 1.0 mmol), and additional THF (1 mL). The resulting red mixture was heated under argon at 70° C. until the starting halide had been consumed as judged by GC analysis. The Schlenk tube was cooled to room temperature, and diethyl ether (25 mL) and $H_2O$ (25 mL) were added. The aqueous layer was separated and extracted with diethyl ether (25 mL). The organic layers were combined, washed with brine (40 mL), dried over $MgSO_4$, filtered, and concentrated. The crude product was then purified by flash chromatography on silica gel. Using 1.0 mmol of ketone and Tol-BINAP gave 94 mg (84% yield) of a colorless oil. $^1$H NMR (CDCl$_3$, 250 MHz) δ 7.92 (d, J=8.0 Hz, 2H), 7.10 (d, J=8.0 Hz, 2H), 3.63 (s, 2H), 2.35 (s, 2H), 1.01 (s, 9H); $^{13}$C NMR (CDCl$_3$, 250 MHz) δ 207.0, 150.0, 143.0, 136.6, 132.7, 129.9, 128.7, 128.4, 120.2, 113.5, 112.2, 55.1, 47.9, 19.3; IR (neat, cm$^{-1}$) 2975, 2932, 1682, 1597, 1583. Anal Calcd for $C_{12}H_{17}OCl$: C, 67.76; H, 8.06. Found: C, 67.99; H, 8.01.

Example 13

Synthesis of 1-(2,5-dimethylphenyl)-3',4'-methylenedioxyacetophenone

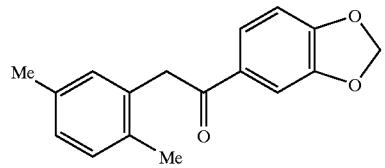

An oven-dried Schlenk tube containing a stir bar was charged with Pd$_2$(dba)$_3$ (6.9 mg, 0.0075 mmol, 1.5 mol %), ligand (0.018 mmol, 3.6 mol %), and NaOt-Bu (65 mg, 0.65 mmol). The Schlenk tube was evacuated and back filled with argon. THF (2 mL) was added followed by aryl halide (0.5 mmol), ketone (0.6 mmol or 1.0 mmol), and additional THF (1 mL). The resulting red mixture was heated under argon at 70° C. until the starting halide had been consumed as judged by GC analysis. The Schlenk tube was cooled to room temperature, and diethyl ether (25 mL) and $H_2O$ (25 mL) were added. The aqueous layer was separated and extracted with diethyl ether (25 mL). The organic layers were combined, washed with brine (40 mL), dried over $MgSO_4$, filtered, and concentrated. The crude product was then purified by flash chromatography on silica gel. Using 0.6 mmol of ketone and rac-BINAP gave 121 mg (90% yield) of a colorless oil. $^1$H NMR (CDCl$_3$, 250 MHz) δ 7.63 (dd, J=8.2, 1.7 Hz, 1H), 7.48 (s, 1H), 7.09 (d, J=7.7 Hz, 1H), 6.98 (d, J=7.7 Hz, 1H), 6.92 (s, 1H), 6.85 (d, J=8.2, 1.7 Hz, 1H), 6.03 (s, 2H), 4.18 (s, 2H), 2.27 (s, 3H), 2.20 (s, 3H); $^{13}$C NMR (CDCl$_3$, 250 MHz) δ 195.6, 151.7, 148.1, 135.3, 133.4, 133.3, 131.7, 130.8, 130.1, 127.7, 124.4, 108.0, 107.8, 43.0, 20.8, 19.1; IR (neat, cm$^{-1}$) 2914, 1681, 1603, 1504, 1486, 1442. Anal Calcd for $C_{17}H_{16}O_3$: C, 76.1; H, 6.01. Found: C, 76.10, H, 6.29.

Example 14

Asymmetric Alkylation and Vinylation of Ketone Enolates

The creation of all-carbon quaternary centers with absolute control of stereochemistry remains a great challenge in organic synthesis.[1] A number of methods have been developed to accomplish this task, including the Pd-catalyzed asymmetric allylations of soft enolates reported by Hayashi (β-diketones)[2] and Trost (β-ketoesters).[3] We now report the first examples, to our knowledge, of the catalytic asymmetric arylation of ketone enolates to produce all-carbon quaternary centers.[4]

We recently disclosed that nascent ketone enolates generated in presence of an aryl bromide and a catalytic quantity of a Pd catalyst are converted to their α-aryl

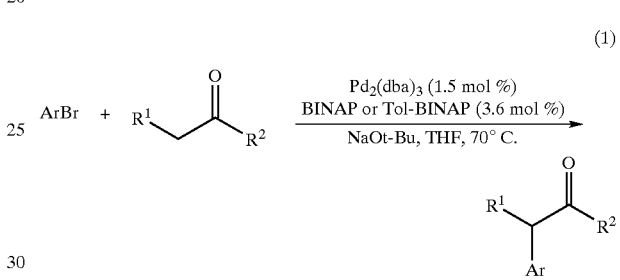

(1)

derivatives with a high degree of regioselectivity (eq 1).[5–7] As our initial protocol employed (S)-Tol-BINAP/Pd$_2$(dba)$_3$ [dba=dibenzylideneacetone] as catalyst, the application of this methodology to asymmetric arylation processes was of interest. Our initial attempts at asymmetric arylation to produce tertiary stereocenters either by direct arylation or desymmetrization of cyclic ketones gave disappointing results. Our attention then turned to the formation of quaternary centers. In our first experiments we were able to asymmetrically arylate 2-methyl-α-tetralone with 1-bromo-4-t-butylbenzene to give the desired product with an ee of 61%, albeit in low yield. Subsequent experimentation has led to an improvement upon these initial results, which we now report.

We found that both the yield and the enantioselectivity of the arylation of 2-methyl-α-tetralone could be brought to good levels by running the arylation using 10–20 mol % Pd(0)/12–24 mol % BINAP in toluene at 100° C.[8,9] It was found that an excess of aryl bromide was necessary to ensure complete conversion of the ketone; 2-methyl-1-naphthol, biaryls, and compounds resulting from aldol condensation were formed as side-products. In some reactions, the α-phenylated ketone was also observed as a side product. Subsequent experiments demonstrated that the latter side product was a result of aryl transfer from the phosphine ligand.[10] Using the conditions described above, the arylations of 2-methyl-α-tetralone proceeded with enantioselectivities up to 88% (Table 1).[11] We have also briefly examined the reactions of 2-methyl-1-indanone, 1. Using 5 mol % Pd(OAc)$_2$/12 mol % BINAP the reaction with

TABLE 1

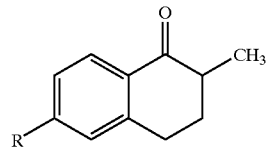

| R | ArBr (2 eq) | % ee | % yield |
|---|---|---|---|
| H | C6H5Br | 73 | 66 |
| H | 4-t-Bu-C6H4Br | 88 | 73[a] |
| MeO | 4-t-Bu-C6H4Br | 77 | 56[b] |
| H | 3-(1,3-dioxolan-2-yl)-C6H4Br (2) | 84 | 74 |
| H | 4-CN-C6H4Br | 61 | 40[c] |

[a]Product contains 4% of 2-methyl-2-phenyl-1-tetralone and 3% of a regioisomer which was present in the starting aryl bromide (percentages determined by GC analysis).
[b]Product contains 3% of a regioisomer which was present in the starting aryl bromide (percentages determined by GC analysis).
[c]The reaction was run at 70° C. using 5.0 equiv halide and 5.0 equiv NaOtBu.

bromide 2 proceeded smoothly to give 3 in 79% yield with an ee of 70% (eq 2).[12] Surprisingly, preliminary attempts to couple para-substituted aryl bromides with 1 gave products which were racemic.

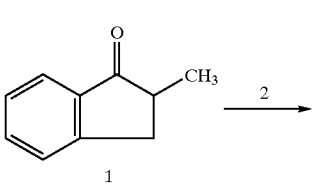

(2)

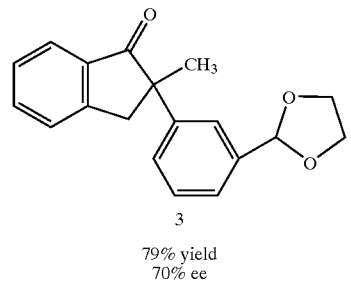

3
79% yield
70% ee

We next extended our investigation to include some α'-blocked α-methylcycloalkanones. These studies gave some enigmatic, yet intriguing results.

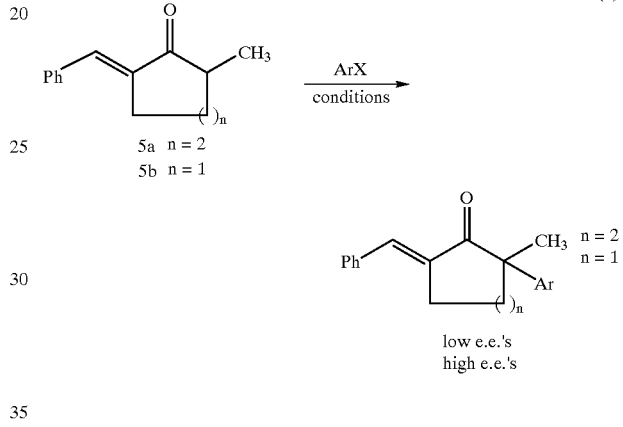

(3)

For example, treatment of 2-methylcyclohexanone derivative 5a[13] with a number of aryl bromides under conditions similar to those described above (or using NaHMDS[14] as base) yielded products with very low ee's (eq 3). However, the reactions of the analogue 5b[15] proceeded with high yields and with extremely high levels of enantioselecitivity as is shown below (FIG. 1). Meta- or para-substituted aryl bromides, coupled

FIG. 1

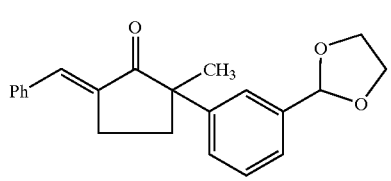

6a
86% yield, 95% ee
(NaHMDS, 10 mol %
Pd2(dba)3/BINAP)

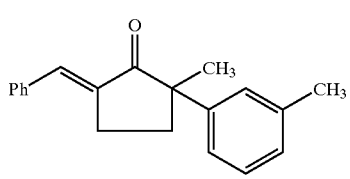

6b
80% yield, 94% ee
(NaOtBu, 20 mol %
Pd(OAc)2/BINAP)

-continued

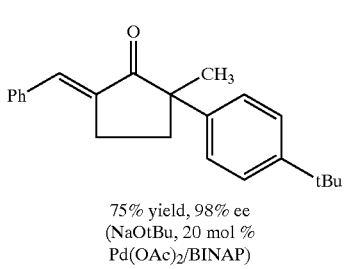

6c

75% yield, 98% ee
(NaOtBu, 20 mol %
Pd(OAc)₂/BINAP)

with 5b to give the desired products in very good yield and in a highly enantioselective fashion. If NaHMDS and Pd₂(dba)₃ was used in place of NaOt-Bu and Pd(OAc)₂, 6c[16] was formed in 91% yield and with an ee of 92%.

There are a number of mysterious features of these reactions. For example, we currently have no good explanation for the difference in levels of enantioselectivity observed for the reactions of 5a and 5b under identical reaction conditions. Moreover, while the reactions of 5b, shown above, proceed with high levels of enantioselectivity, in preliminary studies, similar reactions with 2-bromopropene, 2,4-dimethylbromobenzene or the triflate derived from 4-hydroxy(methylbenzoate) yielded racemic products. Additionally, while the coupling of 1 and 2 gives 3 with an ee of 70%, the analogous reactions of 1 with para-substituted aryl bromides yields racemic products.

The mechanism of this reaction presumably follows a similar pathway to the one postulated for the non-asymmetric Pd-catalyzed α-arylation of ketones. At this point in time it is not clear which step or steps in the catalytic cycle determine the enantioselectivity of the overall process.

REFERENCES AND FOOTNOTES FOR EXAMPLE 14

(1) Fuji, K. Chem. Rev. 1993, 93, 2037–2066.
(2) Hayashi, T.; Kanehira, K.; Hagihara, T.; Kumada, M. J. Org. Chem. 1988, 53, 113–120.
(3) Trost, B. M.; Radinov, R.; Grenzer, E. M. J. Am. Chem. Soc. 1997, 119, 7879–7880.
(4) The palladium-catalyzed asymmetric arylation of a silyl ketene acetal, [E-MeCH=C(OMe)(OSiMe₃)], using a stoichiometric amount of TlOAc to form tertiary carbon centers has been reported (ee's range from 37–54%; only 2 aryl halides were examined). The asymmetric arylation of the corresponding tin enolate was also studied, although lower ee's were obtained: Galarini, R; Musco, A.; Pontellini, R. J. Mol. Cat. 1992, 72, L11–L13.
(5) Palucki, M.; Buchwald, S. L. J. Am. Chem. Soc. 1997, In Press.
(6) (a) Similar processes (as in ref 5a) have recently been described by others: Hamann, B. C.; Hartwig, J. F. J. Am. Chem. Soc. 1997, In Press; Muratake has recently reported a related Pd-catalyzed intramolecular α-arylation of ketones: (b) Muratake, H.; Hayakawa, A.; Natsume, M. Tetrahedron Lett. 1997, 38, 7577–7580. (c) Muratake, H.; Natsume, M. Tetrahedron Lett. 1997, 38, 7581–7582. (d) Satoh has recently reported a single example of the Pd-catalyzed diarylation of 1,3-diphenylacetone with iodobenzene to form 1,1,3,3-tetraphenylacetone: Angew. Chem. Int. Ed. Engl. 1997, 36, 1740–1742.
(7) For other examples of enolate α-arylation, see references contained in 5 and 6c.
(8) Control experiments were run with no palladium catalyst in the presence of NaHMDS at 100° C. for the reaction of 2-methyl-1-tetralone with 1-bromo-4-t-butylbenzene and with 4-bromobenzonitrile. 1-bromo-4-t-butylbenzene did not react with the tetralone in the absence of palladium catalyst. The reaction involving 4-bromobenzonitrile showed ~7% conversion after 1 h, but did not proceed further after heating for another 2 h.
(9) Reactions of 2-ethyl-1-tetralone are inefficient under these conditions.
(10) Using Tol-BINAP instead of BINAP gave small amounts of the α-(p-tolyl) ketone and none of the phenylated ketone could be detected.
(11) Representative procedure: An oven-dried Schlenk tube was charged with Pd₂(dba)₃ or Pd(OAc)₂ (10–20 mol % Pd), (S)-(−)-BINAP (12–24 mol %, 1.2 L/Pd), and sodium t-butoxide (96 mg, 1.0 mmol). The tube was purged with argon and toluene (6 mL) was added. The mixture was stirred at room temperature for 1 minute. The aryl halide (1.0 mmol) and an internal standard (dodecane, 0.115 mL, 0.5 mmol) were added and the mixture was stirred at room temperature for 1 minute. 2-methyl-1-tetralone (0.075 mL, 0.5 mmol) and additional toluene (3 mL) were added and the reaction mixture was heated to 100° C. with stirring until the ketone had been consumed as judged by GC or TLC analysis. The reaction mixture was cooled to room temperature, quenched with saturated aqueous ammonium chloride (~5 mL) and diluted with ether (~10 mL). The layers were separated and the aqueous portion was extracted with ether (~20 mL), and the combined organic layers were washed with saturated brine (~10 mL), dried over anhydrous magnesium sulfate, filtered, and concentrated in vacuo. The crude product was purified by flash chromatography on silica gel. Products which were difficult to completely separate from BINAP by silica gel chromatography were purified according to an alternative workup procedure. See supporting information for full experimental details.
(12) In preliminary experiments we have shown that 1 reacts with 2-bromopropene to give product with an ee of ~60–70%. It is worth noting, that an asymmetric vinylation/ olefin hydrogenation sequence is the synthetic equivalent of a catalytic asymmetric alkylation.
(13) Johnson, W. S. J. Am. Chem. Soc. 1943, 65, 1317–1324.
(14) NaHMDS=Sodium Hexamethyldisilazide (sodium bis(trimethylsilyl)amide).
(15) Sato, T.; Hayase, K. Bull. Chem. Soc. Jpn 1991, 64, 3384–3389.
(16) This product contained 2% (as judged by GC analysis) of a regioisomer which was also present in the starting aryl halide. No regioisomers were observed with any of the other compounds reported in this paper which were made from halides other than 1-bromo-4-t-butylbenzene.

Example 15

Asymmetric Synthesis of 2-methyl-2-phenyl-1-tetralone

An oven-dried Schlenk tube was charged with Pd₂(dba)₃ or Pd(OAc)₂ (10–20 mol % Pd), (S)-(−)-BINAP (12–24 mol %, 1.2 L/Pd), and sodium t-butoxide (96 mg, 1.0 mmol). The tube was purged with argon and toluene (6 mL) was added. The mixture was stirred at room temperature for 1 minute. The aryl halide (1.0 mmol) and an internal standard (dodecane, 0.115 mL, 0.5 mmol) were added and the mixture was stirred at room temperature for 1 minute. 2-methyl-1-tetralone (0.075 mL, 0.5 mmol) and additional toluene (3 mL) were added and the reaction mixture was heated to 100° C. with stirring until the ketone had been consumed as judged by GC or TLC analysis. The reaction mixture was cooled to room temperature, quenched with saturated aqueous ammonium chloride (5 mL) and diluted with ether (10 mL) and THF (1 mL). Hydrogen peroxide (30% aqueous) was added and the mixture was stirred at room temperature for 5 min (in order to oxidize the phosphine). The mixture was then poured into a separatory funnel and the aqueous layer was separated. The ether layer was washed with distilled water (10 mL) and saturated aqueous $FeSO_4$ (20 mL) (CAUTION: The reaction between $H_2O_2$ and $FeSO_4$ is vigorously exothermic, and both the washing of the organic layer with aqueous $FeSO_4$ and the mixing of the aqueous washes should be done with care). The aqueous layers were combined and allowed to cool to room temperature and then were extracted with ether (3×20 mL). The combined organic extracts were washed with saturated brine (20 mL), dried over anhydrous magnesium sulfate, filtered, and concentrated. The crude product was then purified by flash chromatography on silica gel to give 80 mg (68%) of a yellow oil. The ee was determined to be 72% by chiral HPLC analysis (Chiralpak OT(+), 2% isopropanol/hexane, 0.5 mL/min). $[\alpha]^{24°}=-220°$ (c 1.01, $CHCl_3$). $^1H$ NMR ($CDCl_3$, 300 MHz) δ 8.16 (d, J=7.8 Hz, 1H), 7.41 (t, J=7.3 Hz, 1H), 7.33–7.17 (m, 6H), 7.11 (d, J=7.2 Hz, 1H), 2.85–2.80 (m, 2H), 2.59 (dt, 6.6 Hz, 16.8 Hz, 1H), 2.34–2.21 (m, 1H), 1.53 (s, 3H); $^{13}C$ NMR ($CDCl_3$, 500 MHz) δ 201.3, 143.5, 142.0, 133.1, 132.7, 128.6, 128.5, 127.9, 126.6, 126.5, 126.3, 50.5, 36.2, 27.0, 26.1; IR (neat, $cm^{-1}$) 1683. Anal Calcd for $C_{17}H_{16}O$: C, 86.41; H, 6.82. Found: C, 86.69; H, 6.99.

Example 16
Asymmetric Synthesis of 2-methyl-2-(4-cyanophenyl)-1-tetralone

The procedure described in Example 15 using 5 equiv (2.5 mmol) halide, 5 equiv (2.5 mmol) NaOtBu, a reaction temperature of 70° C. gave 46 mg (35%) of a yellow oil. The ee was determined to be 62% by chiral HPLC analysis (Chiralpak OT(+), 10% isopropanol/hexane, 1.2 mL/min). $[\alpha]^{24°}=-124°$ (c 0.98, $CHCl_3$). $^1H$ NMR ($CDCl_3$, 300 MHz) δ 8.13 (d, J=8.0 Hz, 1H), 7.57 (d, J=8.3 Hz, 2H), 7.46 (t, J=7.3 Hz, 1H), 7.35–7.30 (m, 3H), 7.14; (d, J=7.3 Hz, 1H), 2.92–2.71 (m, 2H), 2.60 (dt, J=4.2 Hz, 14.2 Hz, 1H), 2.33–2.24 (m, 1H), 1.54 (s, 3H); $^{13}C$ NMR ($CDCl_3$, 500 MHz) δ 200.0, 148.0, 143.1, 133.6, 132.3, 132.1, 128.7, 128.0, 127.3, 126.8, 118.6, 110.6, 50.7, 35.9, 26.2, 25.8; IR (neat, $cm^{-1}$) 2231, 1683. Anal Calcd for $C_{18}H_{15}NO$: C, 82.73; H, 5.79. Found: C, 82.53; H, 5.86.

Example 17
Asymmetric Synthesis of 2-methyl-2-(4-t-butylphenyl)-1-tetralone

The procedure described in Example 15 gave 107 mg (73%) of a pale yellow oil which solidified upon standing to give a pale yellow solid, mp 64–68° C. This material contained 4% of 2-methyl-2-phenyl-1-tetralone and 3% of a regioisomer (2% of a regioisomer was found in the starting aryl halide by GC, GC/MS, and $^1H$ NMR analysis). The ee was determined to be 87% by chiral HPLC analysis (Chiralcel OJ, 0.7% isopropanol/hexane, 1.0 mL/min). $[\alpha]^{24°}=-171°$ (c 1.00, $CHCl_3$). $^1H$ NMR ($CDCl_3$, 300 MHz) δ 8.15 (d, J=6.7 Hz, 1H), 7.39 (dt, J=1.5 Hz, 7.34 Hz, 1H), 7.32–7.24 (m, 4H), 7.14–7.10 (m, 2H), 2.89–2.78 (m, 2H), 2.63–2.58 (m, 1H), 2.31–2.19 (m, 1H), 1.51 (s, 3H), 1.26 (s, 9H); $^{13}C$ NMR ($CDCl_3$, 500 MHz) δ 201.3, 149.2, 143.7, 138.8, 133.0, 132.7, 128.6, 127.9, 126.5, 125.9, 125.4, 50.0, 36.2, 34.3, 31.2, 27.1, 26.1; IR (KBr, $cm^{-1}$) 1679. A small amount of this material was recrystallized from hexane to give a product which was >99% pure as judged by GC analysis. The ee of this material was determined to be 83%.

This sample was submitted for elemental analysis. Anal Calcd for $C_{21}H_{24}O$: C, 86.26; H, 8.27. Found: C, 86.26; H, 8.49.

Example 18
Asymmetric Synthesis of 2-methyl-2-[3-(2-dioxolane)phenyl]-1-tetralone An oven-dried Schlenk tube was charged with $Pd_2(dba)_3$ or $Pd(OAc)_2$ (10–20 mol % Pd), (S)-(−)-BINAP (12–24 mol %, 1.2 L/Pd), and sodium 1-butoxide (96 mg, 1.0 mmol). The tube was purged with argon and toluene (6 mL) was added. The mixture was stirred at room temperature for 1 minute. The aryl halide (1.0 mmol) and an internal standard (dodecane, 0.115 mL,; 0.5 mmol) were added and the mixture was stirred at room temperature for 1 minute. 2-methyl-1-tetralone (0.075 mL, 0.5 mmol) and additional toluene (3 mL) were added and the reaction mixture was heated to 100° C. with stirring until the ketone had been consumed as judged by GC or TLC analysis. The reaction mixture was cooled to room temperature, quenched with saturated aqueous ammonium chloride (~5 mL) and diluted with ether (~10 mL). The layers were separated and the aqueous portion was extracted with ether (~20 mL), and the combined organic layers were washed with saturated brine (~10 mL), dried over anhydrous magnesium sulfate, filtered, and concentrated in vacuo. The crude product was purified by flash chromatography on silica gel to give 113 mg (73%) of a pale yellow oil. The ee was determined to be 84% by chiral HPLC analysis (Chiralpak OT(+), 10% isopropanol/hexane, 1.2 mL/min). $[\alpha]^{24°}=-178°$ (c 1.00, $CHCl_3$). $^1H$ NMR ($CDCl_3$, 300 MHz) 8:8.14 (d, 1=8.0 Hz, 1H), 7.42–7.22 (m, 5H), 7.16 (dt, J=1.6 Hz, 7.5 Hz, 1H), 7.10 (d, J=7.5 Hz, 1H), 5.74 (s, 1H), 4.15–3.96 (m, 4H), 2.89–2.80 (m, 2H), 2.64 (dt, 1=0.1 Hz, 14.0 Hz, 1H), 2.31–2.21 (m, 1H), 1.52 (s, 3H); $^{13}C$ NMR ($CDCl_3$, 500 MHz) δ 201.0, 143.4, 142.1, 138.1, 133.0, 132.5, 128.6, 128.5, 127.8, 127.3, 126.5, 124.7, 124.3, 103.6, 65.2, 65.1, 50.3, .0, 27.0, 26.0; IR (neat, $cm^{-1}$) 1679. Anal Calcd for $C_{20}H_{20}O_3$: C, 77.90; H, 6.54. Found: C, 78.18; H, 6.47.

Example 19
Asymmetric Synthesis of 6-methoxy-2-methyl-2-(4-t-butylphenyl)-1-tetralone The procedure described in Example 18 gave 89 mg (55%) of a pale yellow oil which solidified upon standing to give a pale yellow solid, mp 82–85° C. This material contained 3% of a regioisomer (2% of a regioisomer was found in the starting aryl bromide by GC, GC/MS, and $^1H$ NMR analysis). The ee was determined to be 76% by chiral HPLC analysis (Chiralpak OT(+), 12% isopropanol/hexane, 0.1 mL/min). $[\alpha]^{24°}=-132°$ (c 1.02, $CHCl_3$). $^1H$ NMR ($CDCl_3$, 300 MHz) δ 8.13 (d, J=8.8 Hz, 1H), 7.28–7.24 (m, 2H), 7.13 (d, J=6.7 Hz, 2H), 6.82 (dd, 1–2.9 Hz, 9.1 Hz, 1H), 6.51 (d, J=2.6 Hz, 1H), 3.81 (s, 3H), 2.88–2.65 (m, 2H), 2.60–2.50 (m, 1H), 2.28–2.17 (m, 1H), 1.51 (s, 3H), 1.26 (s, 9H); $^{13}C$ NMR ($CDCl_3$, 500 MHz) δ 200.1, 163.2, 149.1, 146.2, 139.3, 130.3, 126.3, 125.9, 125.3, 113.2, 112.2, 55.3, 49.8, 36.5, 34.3, 31.3, 27.0, 26.6; IR (KBr, $cm^{-1}$) 1679. Anal Calcd for $C_{22}H_{26}O_2$: C, 81.95; H, 8.13. Found: C, 82.05; H, 8.16.

Example 20
Asymmetric Synthesis of 2-methyl-2-[3-(2-dioxolane)phenyl]-1-indanone (3)

The procedure described in Example 18 using ketone 1, halide 2, 5 mol % $Pd(OAc)_2$ and 12 mol % (S)-(−)-BINAP) (water was used to quench the reaction instead of saturated aqueous ammonium chloride) gave 112 mg (76% yield) of ketone 3 as a yellow oil. The ee was determined to be 69% by chiral HPLC analysis (Chiralpak OT(+), 5% isopropanol/hexane, 1.0 mL/min). [α]$^{24°}$=+18° (c 3.0, CHCl$_3$). $^1$H NMR (CDCl$_3$, 300 MHz) δ 7.81 (d, 1–7.8 Hz, 1H), 7.60–7.66 (m, 1H), 7.29–7.49 (m, 6H), 5.77 (s, 1H), 3.98–4.12 (m, 4H), 3.59 (d, J=17.4 Hz, 1H), 3.30 (d, J=117.4 Hz, 1H), 1.66 (s, 3H); $^{13}$C NMR (CDCl$_3$, 500 MHz) δ 208.4, 152.4, 144.0, 138.0, 135.5, 135.1, 128.6, 127.7, 127.1, 126.3, 124.8, 124.7, 124.2, 103.6, 65.2, 53.1, 44.7, 24.8; IR (neat, cm$^{-1}$) 1710, 1606. Anal Calcd for C$_{19}$H$_{18}$O$_3$: C, 77.53; H, 6.16. Found: C, 77.64; H, 6.07.

Example 21

Asymmetric Synthesis of 4-benzylidene-2-methyl-2-[3-(2-dioxolane)phenyl]-cyclopentanone An oven dried Schlenk tube was charged with ketone 5b (0.5 mmol, 93 mg), Pd$_2$(dba)$_3$ (45.8 mg, 0.05 mmol, 20 mol % Pd), (S)-BINAP (80 mg, 0.12 mmol) and the tube was purged with Ar for 10 min. Toluene (3 mL) was added followed by NaHMDS (1.67 mL of a 0.6 M solution in toluene, 1 mmol), 2-(3-bromophenyl) 1,3-dioxolane (154 μL, 1 mmol), an internal standard (dodecane, 115 μL, 0.5 mmol), and toluene (5 mL). The resultant mixture was stirred under Ar at ambient temperature for 10 min and then at 100° C. until all of the ketone had been consumed as judged by GC and TLC analysis (usually 1 h). The mixture was allowed to cool to room temperature and was diluted with diethyl ether (30 mL), and washed once with pH 7 phosphate buffer (20 mL). The mixture was poured into a separatory funnel and the layers were separated. The organic phase was dried over MgSO$_4$ followed by filtration and concentration in vacuo. Flash chromatography on silica gel (hexane:ethyl acetate 10:1–>6:1) furnished ketone 6a 140 mg (80%) as a pale yellow oil. The ee was determined to be 95% by chiral HPLC analysis (Chiralcel OD, 10% isopropanol/hexane, 1 mL/min). [α]$^{22}$=+34° (c 1.03, CHCl$_3$). $^1$H NMR (CDCl$_3$, 300 MHz) δ 7.50 (m, 4H), 7.36 (m, 6H), 5.79 (s, 1H), 4.08 (m, 4H), 2.95 (m, 1H), 2.82 (dtd, J=2.6, 7.3, 13.1 Hz, 1H), 2.65 (ddd, 4.0, 7.3, 13.1 Hz, 1H) 2.02 (td, J=7.9, 13.1 Hz, 1H), 1.50 (s, 3H); $^{13}$C NMR (CDCl$_3$, MHz) δ 208.4, 142.7, 138.1, 135.5, 135.4, 133.9, 130.5, 129.3, 128.6, 128.6, 127.5, 124.8, 124.4, 103.7, 65.2, 65.2, 52.9, 35.5, 26.2, 25.2; IR (neat, cm$^{-1}$) 1710, 1625. Anal Calcd for C$_{22}$H$_{22}$O$_3$: C, 79.02; H, 6.63. Found: C, 79.32; H, 6.53.

Example 22

Asymmetric Synthesis of 4-benzylidene-2-methyl-2-(3-methylphenyl)-cyclopentanone (6b)

An oven dried Schlenk tube was charged with ketone 5b (93 mg, 0.5 mmol), Pd(OAc)$_2$ (22.4 mg, 0.10 mmol, 20 mol % Pd), (S)-BINAP (80 mg, 0.12 mmol) and NaOt-Bu (96 mg, 1 mmol) and the tube was purged with Ar for 10 min. Toluene (3 mL) was added followed by 1-bromo-3-methylbenzene (154 μL, 1 mmol), an internal standard (dodecane, 115 mL, 0.5 mmol), and toluene (5 mL). The resultant mixture was stirred under Ar at ambient temperature for 10 min and then at 100° C. until all of the ketone had been consumed as judged by GC and TLC analysis (usually 1 h). The mixture was allowed to cool to room temperature and was diluted with diethyl ether (30 mL) and washed once with pH7 phosphate buffer (20 mL). The mixture was poured into a separatory funnel and the layers were separated. The organic phase was dried over MgSO$_4$ followed by filtration and concentration in vacuo. Flash chromatography on silica gel (hexane:ethyl acetate 50:1) furnished ketone 6a 110 mg (80%) as a pale yellow oil. The ee was determined to be 94% by chiral HPLC analysis (Chiralcel OJ, 10% isopropanol/hexane, 1 ml/min). [α]$^{22}$=+71° (c 1.03, CHCl$_3$). $^1$H NMR (CDCl$_3$, 500 MHz) δ 7.56–7.19 (m, 9H), 7.06 (d, J=7.3 Hz, 1H), 2.97 (m, 1H), 2.82 (dtd, J=2.9, 8.4, 16.9 Hz, 1H), 2.67 (ddd, J=3.9, 7.8, 12.7 Hz, 1H) 2.36 (s, 3H), 2.02 (td, J=8.6, 13.2H, 1H), 1.51 (s, 3H); $^{13}$C NMR (CDCl$_3$, 500 MHz)3208.8, 142.4, 138.1, 135.7, 135.5, 133.7, 130.5, 129.3, 128.6, 128.4, 127.5, 127.2, 123.4, 52.9, 35.6, 26.3, 25.1, 21.6 IR (neat, cm$^{-1}$) 1710, 1625. Anal Calcd for C$_{20}$H$_{20}$O: C, 86.92; H, 7.29. Found: C, 87.16; H, 7.19.

Example 23

Asymmetric Synthesis of 4-benzylidene-2-methyl-2-(4-t-butylphenyl)-cyclopentanone (6c)

Using the procedure described in Example 22, but using 1-bromo-4-t-butylbenzene, 126 mg (79%) of 6c was obtained as a pale yellow solid, mp 140–143° C. The product contained 2.2% of a regioisomer (2% of a regioisomer was found in the starting aryl halide by GC, GC/MS, and $^1$H NMR analysis). The ee was determined to be 98.5% by chiral HPLC analysis (Chiralcel OJ, 3% isopropanol/hexane, 0.5 mL/min) [α]$^{22}$=+111° (c 1.00, CHCl$_3$). $^1$H NMR (CDCl$_3$, 300 MHz) δ 7.56–7.23 (m, 10H), 3.03–2.77 (m, 2H), 2.64 (ddd, 4.0, 7.8, 13.1 Hz, 1H), 2.02 (td, J=8.4, 13.1 Hz, 1H), 1.53 (s, 3H), 1.30 (s, 9H); $^{13}$C NMR (CDCl$_3$, 500 MHz) δ 208.9, 149.4, 139.3, 135.8, 135.6, 133.7, 130.6, 129.3, 128.6, 126.1, 125.5, 52.6, 35.5, 34.3,;31.3, 26.3, 25.1 IR (neat, cm$^{-1}$) 1706, 1621. Anal Calcd for C$_{23}$H$_{26}$O: C, 86.75; H, 8.23. Found: C, 86.71; H, 8.18.

Example 24

Synthesis of 2-methyl-2-(4-t-butylphenyl)-1-tetralone

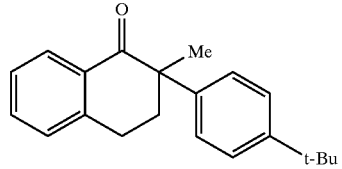

An oven dried Schlenk tube equipped with a rubber septum was cooled under an argon purge. The septum was removed, and the tube was charged with palladium acetate (2.2 mg, 0.01 mmol, 2 mol %) and (S)-BINAP (18.7 mg, 0.03 mmol, 6 mol %). The tube was capped with the septum, purged with argon, and toluene (3 mL) was added through the septum. The mixture was stirred at room temperature and dodecane (0.115 mL), 1-bromo-4-t-butylbenzne (0.17 mL, 1.0 mmol) and 2-methyl t-tetralone (0.075 ml, 0.5 mmol) were added through the septum. The septum was removed and sodium t-butoxide (96 mg, 1.0 mmol) was added. The tube was capped with the septum and purged with argon. Additional toluene (6 mL) was added, and the mixture was heated to 100° C. with stirring until the starting ketone had been consumed, as judged by GC analysis (4 h). The mixture was cooled to room temperature and quenched with saturated aqueous ammonium chloride (5 mL). Hydrogen peroxide (30% aqueous, 2 mL) was added, and the mixture was stirred at room temperature for 5 min. The mixture was diluted with ether (20 mL), and poured into a separatory funnel. The layers were separated and the organic layer was washed with water (10 mL), and saturated aqueous Fe$_2$(SO)$_4$. The combined aqueous layers were extracted with ether (20 mL), and the combined organic layers were washed with brine (20 mL), dried over anhydrous magnesium sulfate, filtered, and concentrated in vacuo. The crude material was purified by flash chromatography on silica gel to afford 109 mg (75%) of the title compound. The ec was determined to be 87% by chiral HPLC analysis.

Example 25
Synthesis of 2-methyl-2-[3-(2-dioxolane)phenyl]-1-tetralone

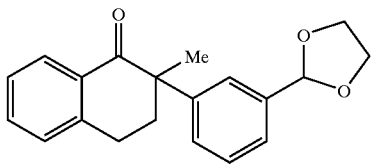

An oven dried Schlenk tube equipped with a rubber septum was purged with argon. The septum was removed, and the tube was charged with palladium acetate (2.2 mg, 0.01 mmol, 2 mol %) and (S)-BINAP (18.7 mg, 0.03 mmol, 6 mol %). The tube was capped with the septum, purged with argon, and toluene (3 mL) was added through the septum. The mixture was stirred at room temperature and dodecane (0.115 mL), 2-(3-bromophenyl)-1,3-dioxolane (0.15 mL, 1.0 mmol) and 2-methyl 1-tetralone (0.075 mL, 0.5 mmol) were added through the septum. The septum was removed and sodium 1-butoxide (96 mg, 1.0 mmol) was added. The tube was capped with the septum and purged with argon. Additional toluene (6 mL) was added, and the mixture was heated to 100° C. with stirring until the starting ketone had been consumed as judged by GC analysis (4 h). The mixture was cooled to room temperature and quenched with saturated aqueous ammonium chloride (5 mL). The mixture was diluted with ether (20 mL), and poured into a separatory funnel. The layers were separated and the aqueous layer was extracted with ether (20 mL). The combined organic layers were washed with brine (20 mL), dried over anhydrous magnesium sulfate, filtered, and concentrated in vacuo. The crude material was purified by flash chromatograpy on silica gel to afford 118 mg (77%) of the title compound. The ee was determined to be 84% by chiral HPLC analysis.

Example 26
Synthesis of 2-methyl-2-(p-biphenyl)-γ-butyrolactone

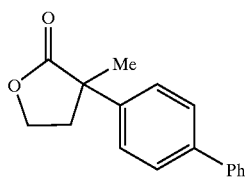

An oven dried Schlenk tube was charged with sodium bis(trimethylsilyl)amide in a nitrogen-filled glovebox. The tube was capped with a rubber septum and removed from the glovebox. The septum was removed and 4-bromobiphenyl (233 mg, 1.0 mmol), palladium acetate (22.4 mg, 0.1 mmol, 20 mol %), and (S)-BINAP (76 mg, 0.12 mmol, 24 mol %) were added under a stream of argon. The tube was capped with the septum and purged with argon. THF (6 mL) was added, and the mixture was stirred at room temperature for 2 min. 2-methyl-γ-butyrolactone (47 μL, 0.5 mmol) was added through the septum, followed by additional THF (3 mL). The mixture was heated to 70° C. with stirring until the lactone had been consumed as judged by GC analysis. The mixture was cooled to room temperature, quenched with saturated aqueous ammonium chloride (5 mL), and diluted with ether (20 mL). The mixture was poured into a separatory funnel and the layers were separated. The aqueous layer was extracted with ether (20 mL), and the combined organic layers were dried over anhydrous magnesium sulfate. The mixture was filtered, and concentrated in vacuo. The crude material was purified by flash chromatography on slilica gel to afford 69 mg (51%) of the title compound. The ee was determined to be 67% by chiral HPLC analysis.

Example 27
Synthesis of 2-methyl-2-[3-(2-dioxolane)phenyl]-γ-butyrolactone

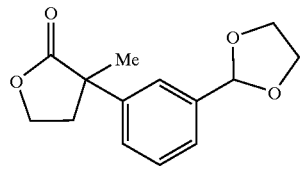

An oven dried Schlenk tube was charged with sodium bis(trimethylsilyl)amide in a nitrogen-filled glovebox. The tube was capped with a rubber septum and removed from the glovebox. The septum was removed and palladium acetate (22.4 mg, 0.1 mmol, 20 mol %) and (S)-BINAP (76 mg, 0.12 mmol, 24 mol %) were added under a stream of argon. The tube was capped with the septum and purged with argon. Toluene (6 mL) was added, and the mixture was stirred at room temperature for 1 min. 2-(3-bromophenyl)1,3-dioxolane (0.15 mL, 1.0 mmol) was added through the septum, and the mixture was stirred at room temperature for 1 min. 2-methyl-γ-butyrolactone (47 μL, 0.5 mmol) was added through the septum, followed by additional Toluene (3 mL). The mixture was heated to 100° C. with stirring until the lactone had been consumed as judged by GC analysis. The mixture was cooled to room temperature, quenched with saturated aqueous ammonium chloride (5 mL), and diluted with ether (20 mL). The mixture was poured into a separatory funnel and the layers were separated. The aqueous layer was extracted with ether (20 mL), and the combined organic layers were dried over anhydrous magnesium sulfate. The mixture was filtered, and concentrated in vacuo. The crude material was purified by flash chromatography on silica gel to afford 42 mg (34%) of the title compound. The ee was determined to be 40% by chiral HPLC analysis.

Example 28
Synthesis of 2-methyl-2-[3-2-dioxolane)phenyl]-1-tetralone (BINAP Ligand)

An oven dried Schlenk tube equipped with a rubber septum was cooled under an argon purge. The septum was removed, and the tube was charged with sodium t-butoxide (96 mg, 1.0 mmol), palladium acetate (5.6 mg, 0.025 mmol, 5 mol % Pd), and (S)-BINAP (18.7 mg, 0.03 mmol, 6 mol %). The tube was capped with the septum, and purged with argon. Toluene (6 mL) was added, and the mixture was stirred at room temperature for 1 min. 2-(3-bromophenyl)-1,3-dioxolane (0.15 mL, 1.0 mmol) was added through the septum, and the mixture was stirred at room temperature for 1 min. 2-methyl-1-tetralone (87 mg), and additional toluene (3 mL) were added through the septum, and the mixture was heated to 100° C. with stirring until the starting ketone had been completely consumed as judged by GC analysis. The mixture was cooled to room temperature, quenched with saturated aqueous ammonium chloride (5 mL), and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on slilica gel to afford 107 mg (69%) of the title compound. The ee was determined to be 84% by chiral HPLC analysis.

Example 29
Synthesis of 2-methyl-2-[3-(2-dioxolane)phenyl]-1-tetralone (BIPHEMP ligand)

An oven dried Schlenk tube equipped with a rubber septum was cooled under an argon purge. The septum was removed, and the tube was charged with sodium t-butoxide (96 mg, 1.0 mmol), palladium acetate (5.6 mg, 0.025 mmol, 5 mol % Pd), and (S)-BIPHEMP (16.5 mg, 0.03 mmol, 6 mol %). The tube was capped with the septum, and purged with argon. Toluene (6 mL) was added, and the mixture was stirred at room temperature for 1 min. 2-(3-bromophenyl)-1,3-dioxolane (0.15 mL, 1.0 mmol) was added through the septum, and the mixture was stirred at room temperature for 1 min. 2-methyl-1-tetralone (87 mg), and additional toluene (3 mL) were added through the septum, and the mixture was heated to 100° C. with stirring until the starting ketone had been completely consumed as judged by GC analysis. The mixture was cooled to room temperature, quenched with saturated aqueous ammonium chloride (5 mL), and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 60 mg (39%) of the title compound. The ee was determined to be 82% by chiral HPLC analysis.

Example 30
Synthesis of 2-methyl-2-[3-(2-dioxolane)phenyl]-1-tetralone (MeO-BIPHEP ligand)

An oven dried Schlenk tube equipped with a rubber septum was cooled under an argon purge. The septum was removed, and the tube was charged with sodium t-butoxide (96 mg, 1.0 mmol), palladium acetate (5.6 mg, 0.025 mmol, 5 mol % Pd), and (R)-MeO-BIPHEP (17.5 mg, 0.03 mmol, 6 mol %). The tube was capped with the septum, and purged with argon. Toluene (6 mL) was added, and the mixture was stirred at room temperature for 1 min. 2-(3-bromophenyl)-1,3-dioxolane (0.15 mL, 1.0 mmol) was added through the septum, and the mixture was stirred at room temperature for 1 min. 2-methyl-1-tetralone (87 mg), and additional toluene (3 mL) were added through the septum, and the mixture was heated to 100° C. with stirring until the starting ketone had been completely consumed as judged by GC analysis. The mixture was cooled to room temperature, quenched with saturated aqueous ammonium chloride (5 mL), and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 91 mg (59%) of the title compound. The ee was determined to be 85% by chiral HPLC analysis.

Example 31
Synthesis of 2-methyl-2-[3-(2-dioxolane)phenyl]-1-tetralone (QUINAP Ligand)

An oven dried Schlenk tube equipped with a rubber septum was cooled under an argon purge. The septum was removed, and the tube was charged with sodium 1-butoxide (96 mg, 1.0 mmol), palladium acetate (5.6 mg, 0.025 mmol, 5 mol % Pd), and (R)-QUINAP (13.2 mg, 0.03 mmol, 6 mol %). The tube was capped with the septum, and purged with argon. Toluene (6 mL) was added, and the mixture was stirred at room temperature for 1 min. 2-(3-bromophenyl)-1,3-dioxolane (0.15 mL, 1.0 mmol) was added through the septum, and the mixture was stirred at room temperature for 1 min. 2-methyl-1-tetralone (87 mg), and additional toluene (3 mL) were added through the septum, and the mixture was heated to 100° C. with stirring until the starting ketone had been completely consumed as judged by GC analysis. The mixture was cooled to room temperature, quenched with saturated aqueous ammonium chloride (5 mL), and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 66 mg (43%) of the title compound. The ee was determined to be 81% by chiral HPLC analysis.

Example 32
Synthesis of 2-methyl-2-[3-(2-dioxolane)phenyl]-1-tetralone (NORPHOS Ligand)

An oven dried Schlenk tube equipped with a rubber septum was cooled under an argon purge. The septum was removed, and the tube was charged with sodium t-butoxide (96 mg, 1.0 mmol), palladium acetate (5.6 mg, 0.025 mmol, 5 mol % Pd), and (R,R)—NORPHOS (13.9 mg, 0.03 mmol, 6 mol %). The tube was capped with the septum, and purged with argon. Toluene (6 mL) was added, and the mixture was stirred at room temperature for 1 min. 2-(3-bromophenyl)-1,3-dioxolane (0.15 mL, 1.0 mmol) was added through the septum, and the mixture was stirred at room temperature for 1 min. 2-methyl-1-tetralone (87 mg), and additional toluene (3 mL) were added through the septum, and the mixture was heated to 100° C. with stirring until the starting ketone had been completely consumed as judged by GC analysis. The mixture was cooled to room temperature, quenched with saturated aqueous ammonium chloride (5 mL), and diluted with ether (20 mL). The mixture was poured into a separatory funnel and the layers were separated. The aqueous layer was extracted with ether (20 mL); and the combined organic layers were washed with brine (20 mL), dried over anhydrous magnesium sulfate, filtered, and concentrated in vacuo. The crude material was purified by flash chromatography on silica gel to afford 58 mg (38%) of the title compound. The ee was determined to be 40% by chiral HPLC analysis.

Example 33
Synthesis of 2-ethyl-2-[3-(2-dioxolane)phenyl]-1-tetralone

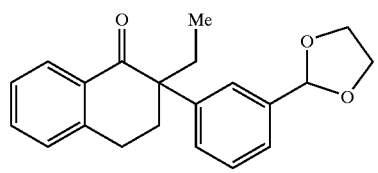

An oven dried Schlenk tube equipped with a rubber septum was cooled under an argon purge. The septum was removed, and the tube was charged with sodium t-butoxide (96 mg, 1.0 mmol), palladium acetate (22.4 mg, 0.1 mmol, 20 mol % Pd), and (S)-QUINAP (52.8 mg, 0.12 mmol, 24 mol %). The tube was capped with the septum, and purged with argon. Toluene (6 mL) was added, and the mixture was stirred at room temperature for 1 min. 2-(3-bromophenyl)-1,3-dioxolane (0.15 mL, 1.0 mmol) was added through the septum, and the mixture was stirred at room temperature for 1 min. 2-ethyl-1-tetralone (87 mg), and additional toluene (3 mL) were added through the septum, and the mixture was heated to 100° C. with stirring until the reaction had stopped progressing as judged by GC and TLC analysis. The mixture was cooled to room temperature, quenched with saturated aqueous ammonium chloride (5 mL), and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 43 mg (27%) of the title compound. The ee was determined to be 92% by chiral HPLC analysis.

Example 34

Synthesis of 2-(4-t-butylphenyl)-2-methyl-5-(N-methyl-anilinomethylene)-cyclopentanone

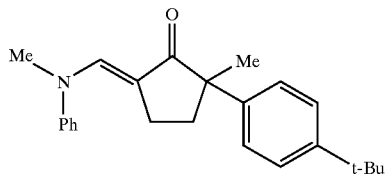

An oven dried Schlenk tube equipped with a rubber septum was cooled under an argon purge. The septum was removed and the tube was charged with palladium acetate (5.6 mg, 0.025 mmol, 5 mol % Pd), (S)-BINAP (23.3 mg, 0.0375 mmol, 7.5 mol %) and 2-methyl-5-(N-methyl-anilinomethylene)-cyclopentanone (108 mg, 0.5 mmol). Toluene (2 mL) was added and the mixture was stirred for 1 min at room temperature. 4-t-Butylbromobenzene (0.17 mL, 1.0 mmol) and sodium t-butoxide (96 mg, 1.0 mmol) were added to the tube, the tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 122 mg (70%) of the title compound. The ee was determined to be 89% by chiral HPLC analysis.

Example 35

Synthesis of 2-(4-t-butylphenyl)-2-methyl-5-(N-methyl-anilinomethylene)-cyclopentanone

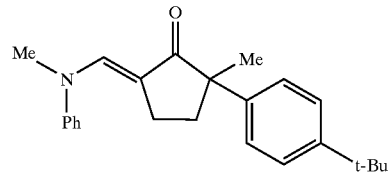

An oven dried Schlenk tube equipped with a rubber septum was cooled under an argon urge. The septum was removed and the tube was charged with palladium acetate (5.6 mg, 0.025 mmol, 5 mol % Pd), (±)-BINAP (23.3 mg, 0.0375 mmol, 7.5 mol %) and 2-methyl-5-(N-methyl-anilinomethylene)-cyclopentanone (108 mg, 0.5 mmol). Toluene (2 mL) was added and the mixture was stirred for 1 min at 40° C. 4-t-Butylbromobenzene (0.17 mL, 1.0 mmol) and sodium t-butoxide (96 mg, 1.0 mmol) were added to the tube, the tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 116 mg (67%) of the title compound.

Example 36

Synthesis of 2-(4-t-butylphenyl)-2-methyl-5-(N-methyl-anilinomethylene)-cyclopentanone

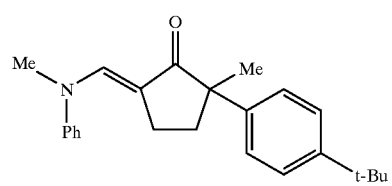

An oven dried Schlenk tube equipped with a rubber septum was cooled under an argon purge. The septum was removed and the tube was charged with palladium acetate (5.6 mg, 0.025 mmol, 5 mol % Pd), (−)-2-(dicyclohexylphosphino)-2'-(dimethylamino)-1,1'-binaphthyl (18.5 mg, 0.038 mmol, 7.5 mol %) and 2-methyl-5-(N-methyl-anilinomethylene) cyclopentanone (108 mg, 0.5 mmol). Toluene (2 mL) was added and the mixture was stirred for 1 min at room temperature. 4-t-Butylbromobenzene (0.17 mL, 1.0 mmol) and sodium t-butoxide (96 mg, 1.0 mmol) were added to the tube, the tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 173 mg (99%) of the title compound. The ee was determined to be 67% by chiral HPLC analysis.

Example 37

Synthesis of 2-(3-Methoxyphenyl)-2-methyl-5-(N-methyl-anilinomethylene)-cyclopentanone

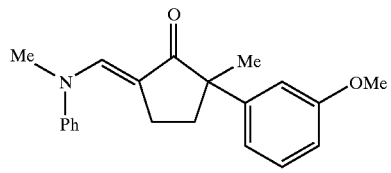

An oven dried Schlenk tube equipped with a rubber septum was cooled under an argon purge. The septum was removed and the tube was charged with tris (dibenzylideneacetone)dipalladium (0) (23 mg, 0.025 mmol, 10 mol % Pd), (S)-BINAP (46.7 mg, 0.075 mmol, 15 mol %) and 2-methyl-5-(N-methyl-anilinomethylene) cyclopentanone (108 mg, 0.5 mmol). Toluene (2 mL) was added and the mixture was stirred for 1 min at room temperature. 3-Bromoanisole (187 mg, 1.0 mmol) and sodium t-butoxide (96 mg, 1.0 mmol) were added to the tube. The tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL), and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 140 mg (87%) of the title compound. The ee was determined to be 85% by chiral HPLC analysis.

Example 38

Synthesis of 2-(4-Methoxyphenyl)$_2$-methyl-5-(N-methyl-anilinomethylene)-cyclopentanone

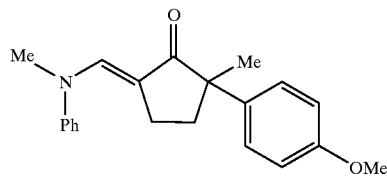

An oven dried Schlenk tube equipped with a rubber septum was cooled under an argon purge. The septum was removed and the tube was charged with tris (dibenzylideneacetone)dipalladium (0) (11.5 mg, 0.025 mmol, 5 mol % Pd), (S)-BINAP (31.4 mg, 0.05 mmol, 10 mol %) and 2-methyl-5-(N-methyl-anilinomethylene) cyclopentanone (108 mg, 0.5 mmol). Toluene (2 mL) was added and the mixture was stirred for 1 min at room temperature. 4-Bromoanisole (187 mg, 1.0 mmol) and sodium 1-butoxide (96 mg, 1.0 mmol) were added to the tube. The tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 88 mg (55%) of the title compound. The ee was determined to be 62% by chiral HPLC analysis.

Example 39

2-[3-(2-Dioxolane)phenyl]-2-methyl-5-(N-methyl-anilinomethylene)cyclopentanone

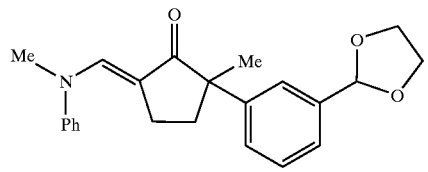

An oven dried Schlenk tube equipped with a rubber septum was cooled under an argon purge. The septum was removed and the tube was charged with tris (dibenzylideneacetone)dipalladium (0) (23 mg, 0.025 mmol, 10 mol % Pd), (S)-BINAP (46.7 mg, 0.075 mmol, 15 mol %) and 2-methyl-5-(N-methyl-anilinomethylene) cyclopentanone (108 mg, 0.5 mmol). Toluene (2 mL) was added and the mixture was stirred for 1 min at room temperature. 2-(3-bromophenyl)-1,3-dioxolane (229 mg, 1.0 mmol) and sodium t-butoxide (96 mg, 1.0 mmol) were added to the tube. The tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 174 mg (96%) of the title compound. The ee was determined to be 86% by chiral HPLC analysis.

Example 40

Synthesis of 2-(4-Tolyl)-2-methyl-5 (N-methyl-anilinomethylene)-cyclopentanone

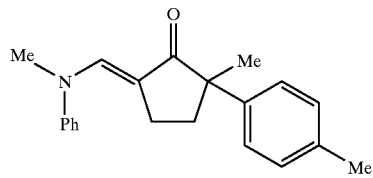

An oven dried Schlenk tube equipped with a rubber septum was cooled under an argon purge. The septum was removed and the tube was charged with palladium acetate (5.6 mg, 0.025 mmol, 5 mol % Pd), (−)-1 (18.5 mg, 0.038 mmol, 7.5 mol %) and 2-methyl-5-(N-methyl-anilinomethylene)cyclopentanone (108 mg, 0.5 mmol). Toluene (2 mL) was added and the mixture was stirred for 1 min at room temperature. 4-Bromotoluene (171 mg, 1.0 mmol) and sodium t-butoxide (96 mg, 1.0 mmol) were added to the tube. The tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 135 mg (88%) of the title compound. The ee was determined to be 75% by chiral HPLC analysis.

Example 41

Synthesis of 2-(3-Tolyl)-2-methyl-5-(N-methyl-anilinomethylene)cyclopentanone

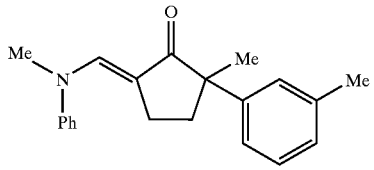

An oven dried Schlenk tube equipped with a rubber septum was cooled under an argon purge. The septum was removed and the tube was charged with tris(dibenzylideneacetone)dipalladium (0) (1.5 mg, 0.0125 mmol, 5 mol % Pd), (S)-BINAP (31.4 mg, 0.05 mmol, 10 mol %) and 2-methyl-5-(N-methyl-anilinomethylene)cyclopentanone (108 mg, 0.5 mmol). Toluene (2 mL) was added and the mixture was stirred for 1 min at room temperature. 3-Bromotoluene (171 mg, 1.0 mmol) and sodium t-butoxide (96 mg, 1.0 mmol) were added to the tube. The tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material; was purified by flash chromatography on silica gel to afford 118 mg (77%) of the title compound. The ee was determined to be 80% by chiral HPLC analysis.

Example 42

Synthesis of 2-(2-Tolyl)-2-methyl-5-(N-methyl-anilinomethylene)-cyclopentanone

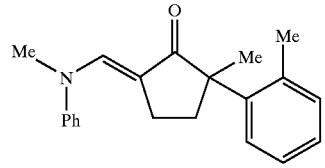

An oven dried Schlenk tube equipped with a rubber septum was cooled under an argon purge. The septum was removed and the tube was charged with tris(dibenzylideneacetone)dipalladium (0) (11.5 mg, 0.0125 mmol, 5 mol % Pd), (S)-BINAP (31.4 mg, 0.05 mmol, 10 mol %) and 2-methyl-5-(N-methyl-anilinomethylene)cyclopentanone (108 mg, 0.5 mmol). Toluene (2 mL) was added and the mixture was stirred for 1 min at room temperature. 3-Bromotoluene (171 mg, 1.0 mmol) and sodium t-butoxide (96 mg, 1.0 mmol) were added to the tube. The tube was capped with the septum, purged with argon, and additional toluene (4 mL) was added through the septum. The mixture was heated to 100° C. with stirring until the starting ketone had been completely consumed, as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 79 mg (52%) of the title compound. The ee was determined to be 8% by chiral HPLC analysis.

Example 43

2-(4-Trifluoromethylphenyl)-2-methyl-5-(N-methyl-anilinomethylene)-cyclopentanone

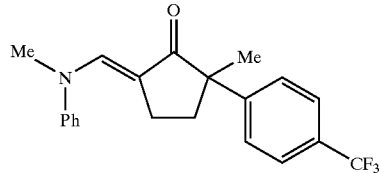

An oven dried Schlenk tube equipped with a rubber septum was cooled under an argon purge. The septum was removed and the tube was charged with tris(dibenzylideneacetone)dipalladium (0) (23 mg, 0.025 mmol, 10 mol % Pd), (S)-BINAP (46 mg, 0.075 mmol, 15 mol %) and 2-methyl-5-(N-methyl-anilinomethylene)cyclopentanone (108 mg, 0.5 mmol). Toluene (2 mL) was added and the mixture was stirred for1 min at room temperature. 4-bromobenzotrifluoride (225 mg, 1.0 mmol) and sodium t-butoxide (96 mg, 1.0 mmol) were added to the tube. The tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 167 mg (93%) of the title compound. The ee was determined to be 53% by chiral HPLC analysis.

Example 44

2-(3-Trifluoromethylphenyl)-2-methyl-5-(N-methyl-anilinomethylene)cyclopentanone

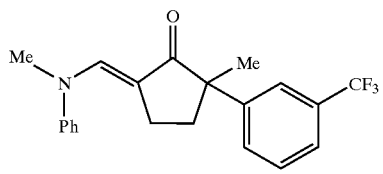

An oven dried Schlenk tube equipped with a rubber septum was cooled under an argon purge. The septum was removed and the tube was charged with tris(dibenzylideneacetone)dipalladium (0) (11.5 mg, 0.0125 mmol, 5 mol % Pd), (S)-BINAP (31.4 mg, 0.05 mmol, 10 mol %) and 2-methyl-5-(N-methyl-anilinomethylene)cyclopentanone (108 mg, 0.5 mmol). Toluene (2 mL) was added and the mixture was stirred for 1 min at room temperature. 3-bromobenzotrifluoride (225 mg, 1.0 mmol) and sodium t-butoxide (96 mg, 1.0 mmol) were added to the tube. The tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 108 mg (60%) of the title compound. The ee was determined to be 75% by chiral HPLC analysis.

Example 45

2-(4-cyanophenyl)-2-methyl-5-(N-methyl-anilinomethylene)-cyclopentanone

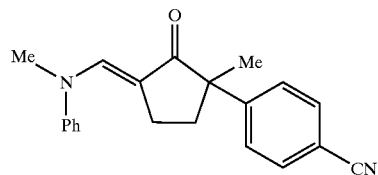

An oven dried Schlenk tube equipped with a rubber septum was cooled under an argon purge. The septum was removed and the tube was charged with palladium acetate (5.6 mg, 0.025 mmol, 5 mol % Pd), (−)-2-(dicyclohexylphosphino)-2'-(dimethylamino)-1,1'-binaphthyl (10.5 mg, 0.038 mmol, 7.5 mol %) and 2-methyl-5-(N-methyl-anilinomethylene)cyclopentanone (108 mg, 0.5 mmol). Toluene (2 mL) was added and the mixture was stirred for 1 min at room temperature. 4-Bromobenzonitrile (182 mg, 1.0 mmol) and sodium t-butoxide (96 mg, 1.0 mmol) were added to the tube. The tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 80 mg (51%) of the title compound. The ee was determined to be 80% by chiral HPLC analysis.

Example 46

2-(3-cyanophenyl)-2-methyl-5-(N-methyl-anilinomethylene)-cyclopentanone

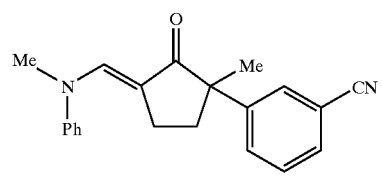

An oven dried Schlenk tube equipped with a rubber septum was cooled under an argon purge. The septum was removed and the tube was charged with palladium acetate (11.2 mg, 0.05 mmol, 10 mol % Pd), (S)-BINAP (46.6 mg, 0.075 mmol, 15 mol %) and 2-methyl-5-(N-methyl-anilinomethylene)-cyclopentanone (108 mg, 0.5 mmol). Toluene (2 mL) was added and the mixture was stirred for 1 min at room temperature. 3-Bromobenzonitrile (182 mg, 1.0 mmol) and sodium t-butoxide (96 mg, 1.0 mmol) were added to the tube. The tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 78 mg (50%) of the title compound. The ee was determined to be 60% by chiral HPLC analysis.

Example 47
2-Phenyl-2-pentyl-5-(N-methyl-anilinomethylene)-cyclopentanone

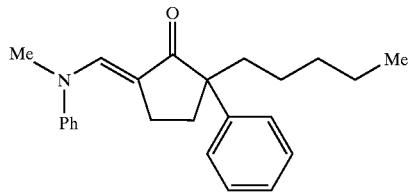

An oven dried Schlenk tube equipped with a rubber septum was cooled under an argon purge. The septum was removed and the tube was charged with tris(dibenzylideneacetone)dipalladium (0) (23 mg, 0.025 mmol, 10 mol % Pd), (S)-BINAP (46 mg, 0.075 mmol, 15 mol %) and 2-pentyl-5-(N-methyl-anilinomethylene)-cyclopentanone (136 mg, 0.5 mmol). Toluene (2 mL) was added and the mixture was stirred for 1 min at room temperature. Bromobenzene (157 mg, 1.0 mmol) and sodium t-butoxide (96 mg, 1.0 mmol) were added to the tube. The tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), the combined organic layers were washed with brine (20 mL), dried over anhydrous magnesium sulfate, filtered, and concentrated in vacuo. The crude material was purified by flash chromatography on silica gel to afford 146 mg (84%) of the title compound. The ee was determined to be 93% by chiral HPLC analysis.

Example 48
2-(4-Trifluoromethylphenyl)-2-pentyl-5-(N-methyl-anilinomethylene)-cyclopentanone

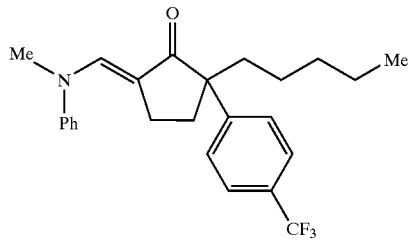

An oven dried Schlenk tube equipped with a rubber septum was cooled under an argon purge. The septum was removed and the tube was charged with tris(dibenzylideneacetone)dipalladium (0) (23 mg, 0.025 mmol, 10 mol % Pd), (S)-BINAP (46 mg, 0.075 mmol, 15 mol %) and 2-pentyl-5-(N-methyl-anilinomethylene) cyclopentanone (136 mg, 0.5 mmol). Toluene (2 mL) was added and the mixture was stirred for 1 min at room temperature. 4-bromobenzotrifluoride (225 mg, 1.0 mmol) and sodium t-butoxide (96 mg, 1.0 mmol) were added to the tube. The tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 148 mg (71%) of the title compound. The ee was determined to be 90% by chiral HPLC analysis.

Example 49
Synthesis of 2-(3-Tolyl)$_2$-pentyl-5-(N-methyl-anilinomethylene)-cyclopentanone

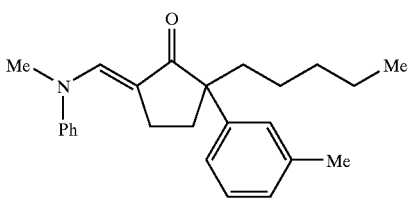

An oven dried Schlenk tube equipped with a rubber septum was cooled under an argon purge. The septum was removed and the tube was charged with palladium acetate (11.2 mg, 0.05 mmol, 10 mol % Pd), (S)-BINAP (46 mg, 0.075 mmol, 15 mol %) and 2-pentyl-5-(N-methyl-anilinomethylene)-cyclopentanone (136 mg, 0.5 mmol). Toluene (2 mL) was added and the mixture was stirred for 1 min at room temperature. Bromobenzene (157 mg, 1.0 mmol) and sodium t-butoxide (96 mg, 1.0 mmol) were added to the tube. The tube was capped with the septum, purged with argon, and additional toluene (4 mL) was added through the septum. The mixture was heated to 100° C. with stirring until the starting ketone had been completely consumed as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), and the combined organic layers were washed with brine (20 mL), dried over anhydrous magnesium sulfate, filtered, and concentrated in vacuo. The crude material was purified by flash chromatography on silica gel to afford 127 mg (70%) of the title compound. The ee was determined to be 99% by chiral HPLC analysis.

Example 50
Synthesis of 2-methyl-2-vinyl-5-(N-methyl-anilinomethylene)cyclopentanone

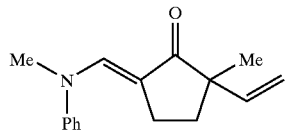

An oven dried Schlenk tube equipped with a rubber septum was purged with argon. The septum was removed, and the tube was charged with palladium acetate (2.2 mg, 0.01 mmol, 2 mol %) and (+)-2-(dicyclohexylphosphino)-2'-(dimethylamino)-1,1'-binaphthyl (10.9 mg, 0.011 mmol 2.2 mol %). The tube was capped with the septum, purged with argon, and toluene (2 mL) and triethylamine (5 mg, 0.05 mmol) were added through the septum. The mixture was stirred at room temperature for 3 min, then vinyl bromide (1.0 mL 1.0 mmol) was added through septum. The septum was removed and 2-methyl-5-(N-methyl-anilinomethylene)cyclopentanone (108 mg, 0.5 mmol) and sodium t-butoxide (96 mg, 1.0 mmol) were added. The tube was capped with the septum and purged with argon. Additional toluene (4 mL) was added and the mixture was stirred at room temperature for 2 h. The mixture was quenched with saturated aqueous ammonium chloride (5 mL), diluted with ether (20 mL) and poured into a separatory funnel. The layers were separated and the aqueous layer was extracted with ether (20 mL). The combined organic layers were washed with brine (20 mL), dried over anhydrous magnesium sulfate, filtered, and concentrated in vacuo. The crude material was purified by flash chromatography on silica gel to afford 113 mg (94%) of the title compound. The ee was determined to be 85% by chiral HPLC analysis.

Example 51

Synthesis of 2-pentyl-2-vinyl-5-(N-methyl-anilinomethylene)cyclopentanone

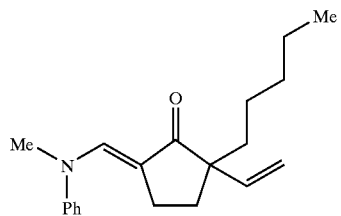

An oven dried Schlenk tube equipped with a rubber septum was purged with argon. The septum was removed, and the tube was charged with tris(dibenzylideneacetone) dipalladium (0) (11.4 mg, 0.013 mmol, 5 mol % Pd) and (+)-2-(dicyclohexylphosphino)$_2$'-(dimethylamino)-1,1'-binaphthyl (13.6 mg, 0.028 mmol 6 mol %). The tube was capped with the septum, purged with argon, and toluene (2 mL) and triethylamine (5 mg, 0.05 mmol) were added through the septum. The mixture was stirred at room temperature for 3 min, then vinyl bromide (1.0 mL 1.0 mmol) was added through septum. The septum was removed and 2-pentyl-5-(N-methyl-anilinomethylene)cyclopentanone (136 mg, 0.5 mmol) and sodium t-butoxide (96 mg, 1.0 mmol) were added. The tube was capped with the septum and purged with argon. Additional toluene (4 mL) was added and the mixture was stirred at room temperature for 18 h. The mixture was quenched with saturated aqueous ammonium chloride (5 mL), diluted with ether (20 mL) and poured into a separatory funnel. The layers were separated and the aqueous layer was extracted with ether (20 mL). The combined organic layers were washed with brine (20 mL), dried over anhydrous magnesium sulfate, filtered, and concentrated in vacuo. The crude material was purified by flash chromatography on silica gel to afford 134 mg (90%) of the title compound. The ee was determined to be 80% by chiral HPLC analysis.

Example 52

2-pentyl-2-vinyl-5-(N-methyl-anilinomethylene) cyclopentanone (Racemic Ligand)

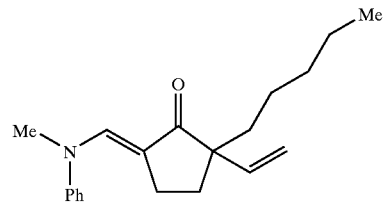

An oven dried Schlenk tube equipped with a rubber septum was purged with argon. The septum was removed, and the tube was charged with tris(dibenzylideneacetone) dipalladium (0) (11.4 mg, 0.013 mmol, 5 mol %) and (±)-2-(dicyclohexylphosphino)-2'-(dimethylamino)-1,1'-binaphthyl (13.6 mg, 0.028 mmol 6 mol %). The tube was capped with the septum, purged with argon, and toluene (2 mL) and triethylamine (5 mg, 0.05 mmol) were added through the septum. The mixture was stirred at room temperature for 3 min, and vinyl bromide (1.0 mL 1.0 mmol) was added through septum. The septum was removed and 2-pentyl-5-(N-methyl-anilinomethylene)cyclopentanone (136 mg, 0.5 mmol) and sodium t-butoxide (96 mg, 1.0 mmol) were added. The tube was capped with the septum and purged with argon. Additional toluene (4 mL) was added and the mixture was stirred at room temperature for 18 h. The mixture was quenched with saturated aqueous ammonium chloride (5 mL), diluted with ether (20 mL) and poured into a separatory funnel. The layers were separated and the aqueous layer was extracted with ether (20 mL). The combined organic layers were washed with brine (20 mL), dried over anhydrous magnesium sulfate, filtered, and concentrated in vacuo. The crude material was purified by flash chromatography on silica gel to afford 139 mg (93%) of title compound.

Example 53

Synthesis of 2-methyl-2-vinyl-1-tetralone

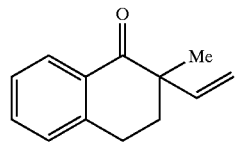

An oven dried Schlenk tube equipped with a rubber septum was purged with argon. The septum was removed, and the tube was charged with palladium acetate (5.6 mg, 0.025 mmol, 5 mol %) and (−)-2-(dicyclohexylphosphino)-2'-(dimethylamino)-1,1'-binaphthyl (13.6 mg, 0.028 mmol 5.5 mol %). The tube was capped with the septum, purged with argon, and toluene (2 mL) and triethylamine (5 mg, 0.05 mmol) were added through the septum. The mixture was stirred at room temperature for 3 min, then vinyl bromide (1.0 mL 1.0 mmol) and 2-methyl-1-tetralone (81 mg, 0.5 mmol) were added through the septum. The septum was removed and sodium t-butoxide (96 mg, 1.0 mmol) was added. The tube was capped with the septum and purged with argon. Additional toluene (4 mL) was added and the mixture was stirred at room temperature for 2 h. The mixture was quenched with saturated aqueous ammonium chloride (5 mL), diluted with ether (20 mL), and poured into a separatory funnel. The layers were separated and the aqueous layer was extracted with ether (20 mL). The combined organic layers were washed with brine (20 mL), dried over anhydrous magnesium sulfate, filtered, and concentrated in vacuo. The crude material was purified by flash chromatography on silica gel to afford 83 mg (88%) of title compound. The ee was 9 determined to be 79% by chiral HPLC analysis.

Example 54
2-methyl-2-(1-propenyl-5-(N-methyl-anilinomethylene)cyclopentanone

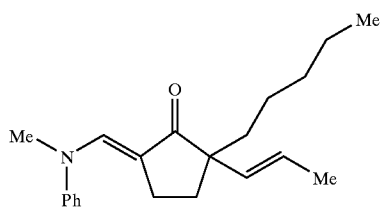

An oven dried Schlenk tube equipped with a rubber septum was purged with argon. The septum was removed, and the tube was charged with palladium acetate (5.6 mg, 0.025 mmol, 5 mol %) and (−)-2-(dicyclohexylphosphino)-2'-dimethylamino)-1,1'-binaphthyl (13.5 mg, 0.028 mmol 5.5 mol %). The tube was capped with the septum, purged with argon, and toluene (2 mL) and triethylamine (5 mg, 0.05 mmol) were added through the septum. The mixture was stirred at room temperature for 3 min, then trans-1-bromo-1-propene (121 mg 1.0 mmol) was added through the septum. The septum was removed and 2-methyl-5-(N-methyl-anilinomethylene)cyclopentanone (108 mg, 0.5 mmol) and sodium 1-butoxide (96 mg, 1.0 mmol) were added. The tube was capped with the septum and purged with argon. Additional toluene (4 mL) was added and the mixture was stirred at room temperature for 18 h. The mixture was quenched with saturated aqueous ammonium chloride (5 mL), diluted with ether (20 mL),; and poured into a separatory funnel. The layers were separated and the aqueous layer was extracted with ether (20 mL). The combined organic layers were washed with brine (20 mL), dried over anhydrous magnesium sulfate, filtered, and concentrated in vacuo. The crude material was purified by flash chromatography on silica gel to afford 115 mg (95%) of title compound. The ee was determined to be 85% by chiral HPLC analysis.

Example 55
2-methyl-2-(1-propenyl)$_{54}$N-methyl-anilinomethylene)cyclopentanone

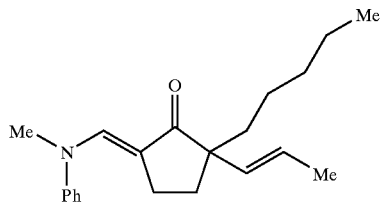

An oven dried Schlenk tube equipped with a rubber septum was purged with argon. The septum was removed, and the tube was charged with trisdibenzylideneacetone dipalladium (6.9 mg, 0.0075 mmol, 3 mol %) and (−)-2-(diisopropylphosphino)$_2$'-(dimethylamino)-1,1'-binaphthyl (7.0 mg, 0.017 mmol 3.3 mol %). The tube was capped with the septum, purged with argon, and toluene (2 mL) was added through the septum. The mixture was stirred at room temperature for 3 min, then trans-1-bromo-1-propene (121 mg 1.0 mmol) was added through the septum. The septum was removed and 2-methyl-5N-methyl-anilinomethylene)cyclopentanone (108 mg, 0.5 mmol) and sodium t-butoxide (96 mg, 1.0 mmol) were added. The tube was capped with the septum and purged with argon. Additional toluene (4 mL) was added and the mixture was stirred at room temperature for 18 h. The mixture was quenched with saturated aqueous ammonium chloride (5 mL), diluted with ether (20 mL) and poured into a separatory funnel. The layers were separated and the aqueous layer was extracted with ether (20 mL). The combined organic layers were washed with brine (20 mL), dried over anhydrous magnesium sulfate, filtered, and concentrated in vacuo. The crude material was purified by flash chromatography on silica gel to afford 124 mg (97%) of the title compound. The ee was determined to be 85% by chiral HPLC analysis.

Example 56
2-methyl-2-(2'-methyl-1'-propenyl)-5-(N-methyl-anilinomethylene)cyclopentanone

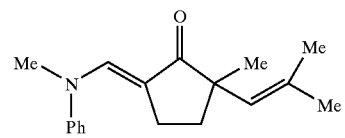

An oven dried Schlenk tube equipped with a rubber septum was purged with argon. The septum was removed, and the tube was charged with palladium acetate (5.6 mg, 0.025 mmol, 5 mol %) and (−)-2-(dicyclohexylphosphino)-2'-(dimethylamino)-1,1'-binaphthyl (13.5 mg, 0.028; mmol 5.5 mol %). The tube was capped with the septum, purged with argon, and toluene (2 mL) and triethylamine (5 mg, 0.05 mmol) were added through the septum. The mixture was stirred at room temperature for 3 min, then trans-1-bromo-2-methyl-1-propene (135 mg, 1.0 mmol) was added through the septum. The septum was removed and 2-methyl-5-(N-methyl-anilinomethylene)cyclopentanone (108 mg, 0.5 mmol) and sodium t-butoxide (96 mg, 1.0 mmol) were added. The tube was capped with the septum and purged with argon. Additional toluene (4 mL) was added and the mixture was stirred at room temperature for 2 h. The mixture was quenched with saturated aqueous ammonium chloride (5 mL), diluted with ether (20 mL) and poured into a separatory funnel. The layers were separated and the aqueous layer was extracted with ether (20 mL). The combined organic layers were washed with brine (20 mL), dried over anhydrous magnesium sulfate, filtered, and concentrated in vacuo. The crude material was purified by flash chromatography on silica gel to afford 128 mg (95%) of title compound. The ee was determined to be 69% by chiral HPLC analysis.

5-(4-chlorophenyl)-3-ethoxy-2-cyclohexen-1-one

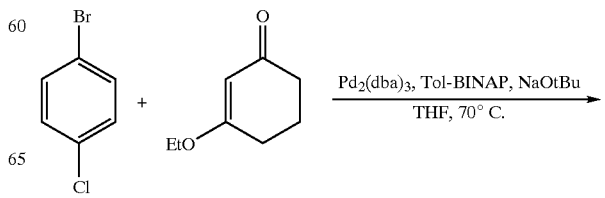

-continued

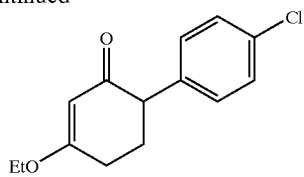

An oven dried Schlenk tube was purged with argon and charged with Pd$_2$(dba)$_3$ (6.9 mg, 0.0075 mmol, 3 mol % Pd), Tol-BINAP (12.2 mg, 0.018 mmol, 3.6 mol %). The tube was taken into a nitrogen-filled glovebox and charged with NaOtBu (66 mg, 0.65 mmol). The tube was capped with a rubber septum and removed from the glovebox. THF (3 mL), 4-bromochlorobenzene (95.7 mg, 0.5 mmol), and 3-ethoxy-cyclohexen-1-one (87 μL, 0.6 mmol) were added to the tube. The mixture was heated to 70° C. with stirring until the starting material had been completely consumed as judged by GC analysis. The mixture was cooled to room temperature, and diethyl ether (25 mL) and H$_2$O (25 mL) were added. The aqueous layer was separated and extracted with diethyl ether (25 mL). The organic layers were combined, washed with brine (40 mL), dried over MgSO$_4$, filtered, and concentrated. The crude product was then purified by flash chromatography on silica gel to afford 40.5 mg (32%) of the title compound. This material was <95% pure by $^1$H NMR analysis, but was determined to consist mainly of the title compound.

Example 58

Arylation of Imine 4

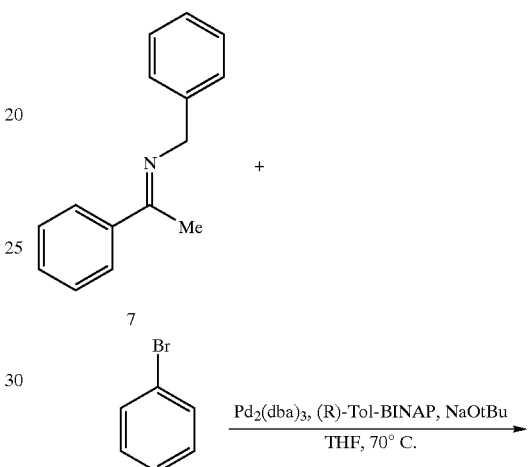

An oven dried Schlenk tube was purged with argon and charged with Pd$_2$(dba)$_3$ (6.9 mg, 0.0075 mmol, 3 mol % Pd), (R)-Tol-BINAP (12.2 mg, 0.018 mmol, 3.6 mol %), and NaOtBu (66 mg, 0.65 mmol). The tube was taken into a nitrogen-filled glovebox and charged with 4 (66 mg, 0.65 mmol). The tube was capped with a rubber septum and removed from the glovebox THF (3 mL), and 4-bromo-t-butylbenzne (87 μL, 0.5 mmol) were added, and the mixture was heated to 70° C. with stirring until the starting material had been completely consumed as judged by GC analysis. GC/MS analysis showed that two products were formed; 5 and its imine isomer 6.

Example 59

Arylation of Imine 7

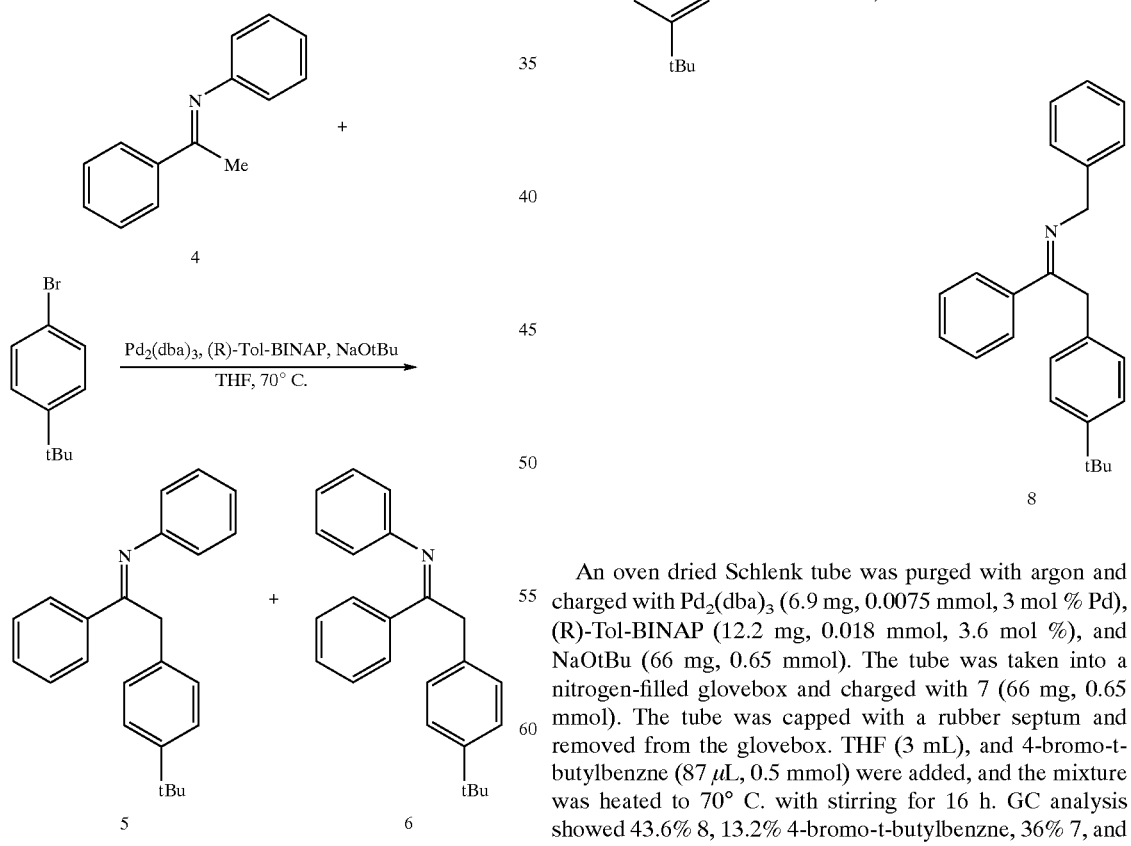

An oven dried Schlenk tube was purged with argon and charged with Pd$_2$(dba)$_3$ (6.9 mg, 0.0075 mmol, 3 mol % Pd), (R)-Tol-BINAP (12.2 mg, 0.018 mmol, 3.6 mol %), and NaOtBu (66 mg, 0.65 mmol). The tube was taken into a nitrogen-filled glovebox and charged with 7 (66 mg, 0.65 mmol). The tube was capped with a rubber septum and removed from the glovebox. THF (3 mL), and 4-bromo-t-butylbenzne (87 μL, 0.5 mmol) were added, and the mixture was heated to 70° C. with stirring for 16 h. GC analysis showed 43.6% 8, 13.2% 4-bromo-t-butylbenzne, 36% 7, and 1.2% t-butylbenzene (numbers are uncorrected GC areas; the identies of the products were confirmed by GC/MS analysis).

Example 60
Arylation of N-Benzylvalerolactam

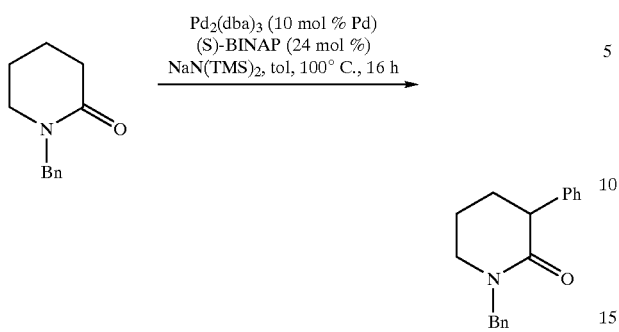

A solution of N-benzyl δ-valerolactam (70 mg, 0.37 mmol) in toluene (3.5 mL) was added via cannula to an oven-dried flask containing Pd$_2$(dba)$_3$ (17 mg, 0.019 mmol) and (S)-BINAP (55 mg, 0.088 mmol). Bromobenzene (47 mL, 0.45 mmol) and a solution of NaN(TMS)$_2$ in toluene (0.6 M, 0.92 mL, 0.55 mmol) were added sequentially via syringe. A water condenser was affixed to the flask, and the reaction mixture was heated in an oil bath at 100° C. for 12 h, whereupon GC analysis revealed that the bromobenzene was completely consumed. The product mixture was analyzed by GC and GC/MS, and shown to contain N-benzyl d-valerolactam (17%), triphenylamine (11%), as well as the title compound (40%).

Example 60
Synthesis of 2-(4-tert-butylphenyl)propiophenone

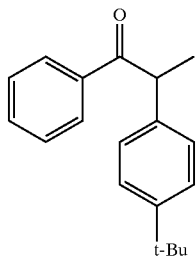

An oven dried Schlenk tube equipped with a rubber septum was cooled under an argon purge. The septum was removed and the tube was charged with tris (dibenzylideneacetone)dipalladium (0) (13.8 mg, 0.015 mmol) and sodium t-butoxide (125 mg, 1.3 mmol). The tube was capped with the septum, and purged with argon. Toluene (2 mL) was added and the mixture stirred for 1 min at room temperature. 4-$^t$Butylbromobenzene (0.17 mL, 1.0 mmol) and propiophenone (0.16 mL, 1.2 mmol) were added to the tube. The mixture was heated to 80° C. and stirred until the starting halide had been completely consumed, as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), the combined organic layers were washed with brine (20 mL), dried over anhydrous magnesium sulfate filtered and concentrated in vacuo. The crude material was purified by flash chromatography on silica gel to afford 145 mg (55%) of α-(4-$^t$butylphenyl)propiophenone. $^1$H NMR (CDCl$_3$, 300 MHz) 7.93–7.89 (m, 2H), 7.43–7.14 (m, 7H), 4.61 (q, 1H, J=6.9 Hz), 1.46 (d, 3H, J=6.9 Hz), 1.20 (s, 9H) ppm.

Example 61
Synthesis of 2-(3-methoxyphenyl)propiophenone (using Pd$_2$(dba)$_3$)

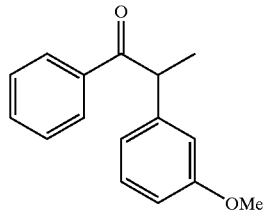

An oven dried Schlenk tube equipped with a rubber septum was cooled under an argon purge. The septum was removed and the tube was charged with tris (dibenzylideneacetone)dipalladium (0) (13.8 mg, 0.015 mmol) and sodium t-butoxide (125 mg, 1.3 mmol). The tube was capped with the septum, and purged with argon. Toluene (2 mL) was added and the mixture stirred for 1 min at room temperature. 3-Bromoanisole (0.125 mL, 1.0 mmol) and propiophenone (0.16 mL, 1.2 mmol) were added to the tube. The mixture was heated to 80° C. and stirred until the starting halide had been completely consumed, as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), the combined organic layers were washed with brine (20 mL), dried over anhydrous magnesium sulfate filtered and concentrated in vacuo. The crude material was purified by flash chromatography on silica gel to afford 130 mg (54%) of α-(3-methoxyphenyl)propiophenone. $^1$H NMR (CDCl$_3$, 300 MHz) 7.93–7.90 (m, 2H), 7.45–7.14 (m, 4H), 6.85–6.68 (m, 3H), 4.61 (q, J=6.9 Hz, 1H), 3.72 (s, 3H), 1.49 (d, J=6.9 Hz, 3H) ppm.

Example 62
Synthesis of 2-(3-methoxyphenyl)propiophenone (Using Pd(OAc)$_2$)

An oven dried Schlenk tube equipped with a rubber septum was cooled under an argon purge. The septum was removed and the tube was charged with palladium acetate (2.3 mg, 0.01 mmol) and sodium t-butoxide (125 mg, 1.3 mmol). The tube was capped with the septum, purged with argon. Toluene (2 mL) was added and the mixture stirred for 1 min at room temperature. 3-Bromoanisole (0.125 mL, 1.0 mmol) and propiophenone (0.16 mL, 1.2 mmol) were added to the tube. The mixture was heated to 80° C. and stirred until the starting halide had been completely consumed, as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), the combined organic layers were washed with brine (20 mL), dried over anhydrous magnesium sulfate filtered and concentrated in vacuo. The crude material was purified by flash chromatography on silica gel to afford 190 mg (79%) of α-(3-methoxyphenyl)propiophenone. $^1$H NMR (CDCl$_3$, 300 MHz) 7.93–7.90 (m, 2H), 7.45–7.14 (m, 4H), 6.85–6.68 (m, 3H), 4.61 (q, 3=6.9 Hz, 1H), 3.72 (s, 3H), 1.49 (d, 3H, J=6.9 Hz) ppm.

Example 63

Synthesis of 2-(2-methoxyphenyl)propiophenone

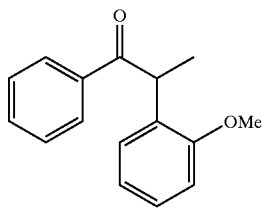

An oven dried Schlenk tube equipped with a rubber septum was cooled under an argon purge. The septum was removed and the tube was charged with palladium acetate (2.3 mg, 0.01 mmol) and sodium t-butoxide (125 mg, 1.3 mmol). The tube was capped with the septum, purged with argon. Toluene (2 mL) was added and the mixture stirred for 1 min at room temperature. 3-Bromotoluene (0.120 mL, 1.0 mmol) and propiophenone (0.16 mL, 1.2 mmol) were added to the tube. The mixture was heated to 80° C. and stirred until the starting halide had been completely consumed, as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), the combined organic layers were washed with brine (20 mL), dried over anhydrous magnesium sulfate filtered and concentrated in vacuo. The crude material was purified by flash chromatography on silica gel to afford 103 mg (46%) of α-(2-Methylphenyl)propiophenone. $^1$H NMR (CDCl$_3$, 300 MHz) 7.81–7.84 (m, 2H), 7.47–6.99 (m, 7l), 4.75 (q, 3=6.9 Hz, 1H), 2.49 (s, 3H), 1.46 (d, J=6.9 Hz, 3H) ppm.

Example 64

Synthesis of 1-(3-methoxyphenyl)-3,3-dimethyl-2-butanone (using Pd$_2$(dba)$_2$)

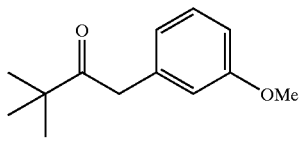

An oven dried Schlenk tube equipped with a rubber septum was cooled under an argon purge. The septum was removed and the tube was charged with tris(dibenzylideneacetone)dipalladium (0) and sodium t-butoxide (125 mg, 1.3 mmol). The tube was capped with the septum, purged with argon. Toluene (2 mL) was added and the mixture stirred for 1 min at room temperature. 3-Bromoanisole (0.125 mL, 1.0 mmol) and pinacolone (0.15 mL, 1.2 mmol) were added to the tube. The mixture was heated to 80° C. and stirred until the starting halide had been completely consumed, as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), the combined organic layers were washed with brine (20 mL), dried over anhydrous magnesium sulfate filtered and concentrated in vacuo. The crude material was purified by flash chromatography on silica gel to afford 99 mg (48%) of α-(3-methoxyphenyl) pinacolone. $^1$H NMR (CDCl$_3$, 300 MHz) 7.22–7.16 (m, 1H), 6.77–6.70 (m, 3H), 3.76 (s, 3H), 3.74 (s, 2H), 1.16 (s, 9H) ppm.

Example 65

Synthesis of 1-(3-methoxyphenyl)-3,3-dimethyl-2-butanone (Using Pd(OAc)

An oven dried Schlenk tube equipped with a rubber septum was cooled under an argon purge. The septum was removed and the tube was charged with palladium acetate (2.3 mg, 0.01 mmol) and sodium t-butoxide (125 mg, 1.3 mmol). The tube was capped with the septum, purged with argon. Toluene (2 mL) was added and the mixture stirred for 1 min at room temperature. 3-Bromoanisole (0.125 mL, 1.0 mmol) and pinacolone (0.15 mL, 1.2 mmol) were added to the tube. The mixture was heated to 80° C. and stirred until the starting halide had been completely consumed, as judged by GC analysis. The mixture was cooled to room temperature, quenched with saturated aqueous ammonium chloride (10 mL) and diluted with ether (20 mL). The mixture was poured into a separatory funnel and the layers were separated. The aqueous layer was extracted with ether (20 mL), the combined organic layers were washed with brine (20 mL), dried over anhydrous magnesium sulfate filtered and concentrated in vacuo. The crude material was purified by flash chromatography on silica gel to afford 146 mg (71%) of α-(3-methoxyphenyl)pinacolone. $^1$H NMR (CDCl$_3$, 300 MHz) 7.22–7.16 (m, 1H), 6.77–6.70 (m, 3H), 3.76 (s, 3H), 3.74 (s, 2H), 1.16 (s, 9H) ppm.

Example 66

Synthesis of 2-(4-methoxyphenyl)propiophenone

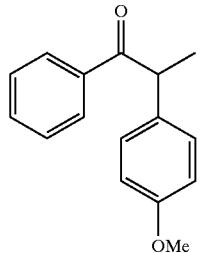

A dry Schlenk tube was charged with Pd(OAc)$_2$ (2.2 mg, 0.01 mmol) and sodium tert-butoxide (125 mg, 1.3 mmol). The tube was then evacuated and filled with argon. Toluene (1 mL), 4-bromoanisole (187 mg, 0.125 mL, 1.0 mmol) and propiophenone (161 mg, 0.160 mL, 1.2 mmol) were sequentially added with a syringe, and the tube was sealed and heated in an oil bath at 80° C. for 14 h. The mixture was cooled, and partitioned between ether and water. The aqueous layer was extracted twice with ether, and the combined organics were dried over Na$_2$SO$_4$, filtered and concentrated. Chromatography on silica gel (12:1 hexane:ethyl acetate was the eluent) gave 0.189 g (79%) of α-(4-methoxyphenyl) propiophenone, a white solid. $^1$H NMR (CDCl$_3$, 300 MHz) a 7.96 (m, 2H); 7.48 (m, 1H); 7.39 (m, 2H); 7.21 (d, 2H, J=8.7 Hz); 6.84 (d; 2H, 8.7 Hz); 4.66 (q, 1H, J=6.9 Hz); 3.76 (s, 3H); 1.52 (d, 3H, J=6.9).

Example 67
Synthesis of 2-(3,5-dimethylphenyl)propiophenone (Using Pd(OAc)₂)

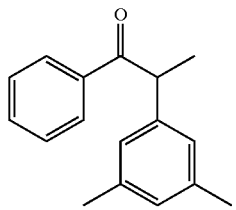

A dry Schlenk tube was charged with Pd(OAc)₂ (2.2 mg, 0.01 mmol) and sodium tert-butoxide (125 mg, 1.3 mmol). The tube was then evacuated and filled with argon. Toluene (1 mL), 5-bromo-m-xylene (185 mg, 0.136 mL, 1.0 mmol) and propiophenone (161 mg, 0.160 mL, 1.2 mmol) were sequentially added with a syringe, and the tube was sealed and heated in an oil bath at 80° C. for 2 h 20 min. The mixture was cooled, and partitioned between ether and water. The aqueous layer was extracted twice with ether, and the combined organics were dried over Na₂SO₄, filtered and concentrated. Chromatography on silica gel, eluting first with hexane, then 4:1 toluene: hexane, gave 0.198 g (83%) of α-(3,5-dimethylphenyl)propiophenone, a clear oil. ¹H NMR (CDCl₃, 300 MHz) δ 7.96 (m, 2H); 7.48 (m, 1H); 7.38 (m, 2H); 6.89 (s, 2H); 6.83 (s, 2H); 4.60 (q, 1H, J=6.9 Hz); 2.26 (s, 6H); 1.50 (d, 3H, J=6.9 Hz).

Example 68
Synthesis of 2-(3,5-dimethylphenyl)propiophenone (Using Pd₂(dba)₃)

A dry Schlenk tube was charged with Pd₂ (DBA)₃ (4.6 mg, 0.005 mmol) and sodium tert-butoxide (125 mg, 1.3 mmol). The tube was then evacuated and filled with argon. Toluene (1 mL), 5-bromo-m-xylene (185 mg, 0.136 mL, 1.0 mmol) and propiophenone (161 mg, 0.160 mL, 1.2 mmol) were sequentially added with a syringe, and the tube was sealed and heated in an, oil bath at 80° C. for 12 h. The mixture was cooled, and partitioned between ether and water. The aqueous layer was extracted twice with ether, and the combined organics were dried over Na₂SO₄, filtered and concentrated. Chromatography on silica gel, eluting first with hexane, then 4:1 toluene:hexane, gave 0.185 g (79%) of α-(3,5-dimethylphenyl)propiophenone, a clear oil. ¹H NMR (CDCl₃, 300 MHz) δ 7.96 (m, 2H); 7.48 (m, 1H); 7.38 (m, 214); 6.89 (s, 2H); 6.83 (s, 2H); 4.60 (q, 1H, J=6.9 Hz); 2.26 (s, 6H); 1.50 (d, 3H, J=6.9 Hz).

Example 69
Synthesis of 1-(4-methylphenyl)-2-(2,5-dimethylphenyl)-1-ethanone

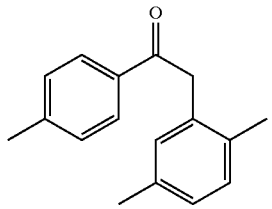

A dry Schlenk tube was charged with Pd(OAc)₂ (2.2 mg, 0.01 mmol) and sodium tert-butoxide (125 mg, 1.3 mmol). The tube was then evacuated and filled with argon. Toluene (1 mL), 2-bromo-pxylene (185 mg, 0.138 mL, 1.0 mmol) and 4-methylacetophenone (161 mg, 0.160 mL, 1.2 mmol) were sequentially added with a syringe, and the tube was sealed and heated in an oil bath at 80° C. for 13 h 45 min. The mixture was cooled, and partitioned between ether and water. The aqueous layer was extracted twice with ether, and the combined organics were dried over Na₂SO₄, filtered and concentrated. Chromatography on silica gel, eluting first with hexane, then 4:1 toluene: hexane, gave 0.152 g (64%) of α-(2,5-dimethylphenyl)₄-methylacetophenone, a clear oil. ¹H NMR (CDCl₃, 300 MHz) δ 7.92 (d, 2H, J=8.4 Hz); 7.27 (d, 2H, J=8.2 Hz); 7.09 (d, 1H, J=7.8 Hz); 6.99 (d, 1H, J=7.8 Hz);

6.94 (s, 1H); 4.24 (s, 2H); 2.42 (s, 3H); 2.28 (s, 3H), 2.21 (s, 3H).

All of the publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method represented by Scheme 1:

Scheme 1

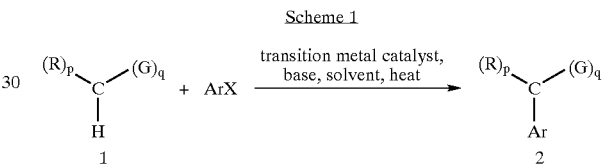

wherein

G represents, independently for each occurrence, an electron withdrawing group selected from the group consisting of formyl, acyl, —C(O)OR, —C(O)NR₂, nitro, nitroso, —S(O)₂R, —SO₃R, —S(O)₂NR₂, —C(NR)—R, —C(NOR)R, and —C(NNR₂)—R;

R represents, independently for each occurrence, hydrogen, alkyl, aryl, heteroalkyl, heteroaryl, halogen, alkylamino, arylamino, alkylthio, arylthio, alkoxy, aryloxy, or —(CH₂)ₘ—R₈;

Ar represents an aromatic or heteroaromatic moiety,

X represents halogen, —OTf, —ONf, —OTs, —OMs, (alkyl)S(O)₂O—, or (aryl)S(O)₂O—;

the transition metal catalyst consists essentially of palladium and one to four inclusive monodentate ligands selected from the group consisting of OAc, Cl, CH₃CN, triphenylphosphine, tri(o-tolyl)phosphine, trimethylphosphine, triethylphosphine, tripropylphosphine, triisopropylphosphine, tributylphosphine, tricyclohexylphosphine, trimethyl phosphite, triethyl phosphite, tripropyl phosphite, triisopropyl phosphite, tributyl phosphite and tricyclohexyl phosphite;

base represents a Bronsted base;

R₈ represents independently for each occurrence a substituted or unsubstituted aryl, cycloalkyl, cycloalkenyl, heterocycle or polycycle;

m, independently for each occurrence, is an integer selected from the range 0 to 8 inclusive;

q is an integer selected from the range 1 to 3 inclusive; and p is an integer equal to (3-q).

2. The method of claim 1, wherein said at least one monodentate ligand is an asymmetric ligand; and the reaction produces a non-racemic mixture of a chiral compound 2.

3. The method of claim 1, wherein R represents, independently for each occurrence, hydrogen, alkyl, aryl, heteroalkyl, heteroaryl, or —(CH$_2$)$_m$—R$_8$.

4. The method of claim 1, wherein X represents Br, I, —OTf, —ONf, —OTs, or —OMs.

5. The method of claim 1, 2, 3, or 4, wherein X represents Br, L —OTf, or —ONf.

6. The method of claim 5, wherein the base is an alkoxide, carbonate, or an amide.

7. The method of claim 6, wherein the base is a salt of tert-butoxide, dialkylamide, or bis(trialkylsilyl)amide.

8. The method of claim 7, wherein the base is lithium, sodium, or potassium tert-butoxide.

9. The method of claim 8, wherein the base is sodium tert-butoxide.

10. The method of claim 5, wherein the solvent is a non-polar, aprotic solvent.

11. The method of claim 9, wherein the solvent is a non-polar, aprotic solvent.

12. The method of claim 10, wherein the solvent is a hydrocarbon.

13. The method of claim 11, wherein the solvent is a hydrocarbon.

14. The method of claim 12, wherein the solvent is an aromatic hydrocarbon.

15. The method of claim 13, wherein the solvent is an aromatic hydrocarbon.

16. The method of claim 14, wherein the solvent is toluene.

17. The method of claim 15, wherein the solvent is toluene.

18. The method of claim 1, wherein q equals 1.

19. The method of claim 17, wherein q equals 1.

20. The method of claim 1, 2, 3, or 4, wherein G represents, independently for each occurrence, acyl, formyl, —C(O)OR, —C(O)NR$_2$, —S(O)$_2$R, —SO$_3$R, —S(O)$_2$NR$_2$, —C(NR)R, —C(NOR)—R, or —C(NNR$_2$)—R.

21. The method of claim 1, 2, 3, or 4, wherein G represents, independently for each occurrence, acyl, —C(O) OR, —C(NR)R, —C(NOR)—R, or —C(NNR$_2$)—R.

22. The method of claim 1, 2, 3, or 4, wherein G represents acyl.

23. The method of claim 1, 2, 3, or 4, wherein the method is practiced between about 70 and 110° C.

24. The method of claim 1, 2, 3, or 4, wherein the method is practiced at about 100° C.

25. The method of claim 1, 2, 3, or 4, wherein the method is practiced at about 70° C.

26. The method of claim 1, 2, 3, or 4, wherein the method is practiced at about 25° C.

27. The method of claim 1, 2, 3, or 4, wherein the product has an ee of greater than or equal to 50%.

28. The method of claim 1, 2, 3, or 4, wherein the product has an ee of greater than or equal to 70%.

29. The method of claim 1, 2, 3, or 4, wherein the product has an ee of greater than or equal to 80%.

30. The method of claim 1, 2, 3, or 4, wherein the product has an ee of greater than or equal to 90%.

* * * * *

UNITED STATES PATENT AND TRADEMARK OFFICE
CERTIFICATE OF CORRECTION

| | | |
|---|---|---|
| PATENT NO. | : 6,867,310 B1 | Page 1 of 1 |
| APPLICATION NO. | : 09/239024 | |
| DATED | : March 15, 2005 | |
| INVENTOR(S) | : Stephen L. Buchwald et al. | |

It is certified that error appears in the above-identified patent and that said Letters Patent is hereby corrected as shown below:

In column 1, lines 13-16, replace:

"The present invention was made in part with support provided by the National Science Foundation and the National Institutes of Health; the government, therefore, has certain rights in the invention."

with

--This invention was made with government support under grant number R01 GM034917 awarded by the National Institutes of Health and grant number CHE9421982 awarded by the National Science Foundation. The government has certain rights in this invention.--

Signed and Sealed this
Twelfth Day of July, 2011

David J. Kappos
*Director of the United States Patent and Trademark Office*